(12) United States Patent
Ji et al.

(10) Patent No.: US 9,187,430 B2
(45) Date of Patent: Nov. 17, 2015

(54) POLY (ADP-RIBOSE) POLYMERASE INHIBITOR

(71) Applicant: CHENGDU DI'AO PHARMACEUTICAL GROUP CO., LTD., Chengdu (CN)

(72) Inventors: Jianxin Ji, Chengdu (CN); Na Guo, Chengdu (CN); Ting Xue, Chengdu (CN); Bingqiang Kang, Chengdu (CN); Xinfa Ye, Chengdu (CN); Xin Chen, Chengdu (CN); Tao Zhang, Chengdu (CN)

(73) Assignee: CHENGDU DI'AO PHARMACEUTICAL GROUP CO., LTD., High-Tech Devlopment Zone, Chengdu (CN)

( * ) Notice: Subject to any disclaimer, the term of this patent is extended or adjusted under 35 U.S.C. 154(b) by 0 days.

(21) Appl. No.: 14/361,698

(22) PCT Filed: Dec. 3, 2012

(86) PCT No.: PCT/CN2012/001611
§ 371 (c)(1),
(2) Date: May 29, 2014

(87) PCT Pub. No.: WO2013/078771
PCT Pub. Date: Jun. 6, 2013

(65) Prior Publication Data
US 2015/0051211 A1 Feb. 19, 2015

(30) Foreign Application Priority Data
Nov. 30, 2011 (CN) .......................... 2011 1 0390364

(51) Int. Cl.
*C07D 237/32* (2006.01)
*C07D 401/14* (2006.01)
*C07D 413/14* (2006.01)
*A61K 31/502* (2006.01)
*A61K 31/5025* (2006.01)
*C07D 401/12* (2006.01)
*C07D 407/14* (2006.01)
*C07D 409/14* (2006.01)
*C07D 417/14* (2006.01)

(52) U.S. Cl.
CPC ............ *C07D 237/32* (2013.01); *A61K 31/502* (2013.01); *A61K 31/5025* (2013.01); *C07D 401/12* (2013.01); *C07D 401/14* (2013.01); *C07D 407/14* (2013.01); *C07D 409/14* (2013.01); *C07D 413/14* (2013.01); *C07D 417/14* (2013.01)

(58) Field of Classification Search
CPC ....................................................... A01N 43/58
USPC .......................................... 544/237; 514/248
See application file for complete search history.

(56) References Cited

U.S. PATENT DOCUMENTS

| | | |
|---|---|---|
| 5,177,075 A | 1/1993 | Suto et al. |
| 6,903,098 B1 | 6/2005 | Lubisch et al. |
| 2002/0183325 A1 | 12/2002 | Martin et al. |
| 2004/0248931 A1 | 12/2004 | Fujio et al. |
| 2005/0059663 A1 | 3/2005 | Martin et al. |
| 2006/0063926 A1 | 3/2006 | Ma et al. |
| 2007/0093489 A1 | 4/2007 | Javaid et al. |
| 2008/0200469 A1 | 8/2008 | Martin et al. |

FOREIGN PATENT DOCUMENTS

| | | |
|---|---|---|
| CN | 1399573 A | 2/2003 |
| CN | 101048399 A | 10/2007 |
| CN | 101925595 A | 12/2010 |
| CN | 1905864 B | 4/2011 |
| CN | 102485721 A | 6/2012 |
| CN | 102107008 B | 4/2013 |
| JP | 2003-502286 A | 1/2003 |
| JP | 2004-513121 A | 4/2004 |
| JP | 2006-519827 A | 8/2006 |
| WO | 99/11645 A1 | 3/1999 |
| WO | 00/32579 A1 | 6/2000 |
| WO | 02/36576 A1 | 5/2002 |
| WO | 02/36599 A1 | 5/2002 |
| WO | 03/063874 A1 | 8/2003 |
| WO | 03/103666 A2 | 12/2003 |
| WO | 2004/080976 A1 | 9/2004 |
| WO | 2004/096779 A1 | 11/2004 |
| WO | 2005/023246 A1 | 3/2005 |
| WO | 2005/053662 A1 | 6/2005 |
| WO | 2005/054210 A1 | 6/2005 |
| WO | 2006/003148 A1 | 1/2006 |
| WO | 2006/021801 A1 | 3/2006 |
| WO | 2007/138355 A1 | 12/2007 |
| WO | 2008/017883 A2 | 2/2008 |
| WO | 2009/093032 A1 | 7/2009 |
| WO | 2011/130478 A1 | 10/2011 |
| WO | 2012/014221 A1 | 2/2012 |
| WO | 2012/072033 A1 | 6/2012 |

OTHER PUBLICATIONS

Pinedo et al (2000).*
McMahon et al. (2000).*
Vippagunta et al. (2001).*
"International Search Report for PCT/CN2012/001611".
(Continued)

*Primary Examiner* — Paul V Ward
(74) *Attorney, Agent, or Firm* — Jun He Law Offices P.C.; James J. Zhu

(57) ABSTRACT

Disclosed are a phthalic hydrazide (phthalazine ketone) compound, and a pharmaceutical composition comprising the same. As a DNA repair enzyme poly (ADP-ribozyme) polymerase inhibitor, the compound and the pharmaceutical composition can effectively treat diseases involving PARP enzymatic activity, including cancer, neural degenerative diseases, inflammation and the like.

2 Claims, 1 Drawing Sheet

(56) References Cited

OTHER PUBLICATIONS

International Preliminary Report on Patentability for PCT/CN2012/001611.
Tentori et al., "Combined treatment with temozolomide and poly(ADP-ribose) polymerase inhibitor enhances survival of mice bearing hematologic malignancy at the central nervous system site", Blood 2002, vol. 99: 2241-2244.
Delaney et al., "Potentiation of Temozolomide and Topotecan Growth Inhibition and Cytotoxicity by Novel Poly (adenosine Diphosphoribose) Polymerase Inhibitors in a Panel of Human Tumor Cell Lines" Clin Cancer Res 2000, vol. 6: 2860-2867.
Calabrese et al., "Anticancer Chemosensitization and Radiosensitization by the Novel Poly(ADP-ribose) Polymerase-1 Inhibitor AG14361" J Natl Cancer Inst 2004, vol. 96: 56-67.
Miknyoczki et al., "Chemopotentiation of Temozolomide, Irinotecan, and Cisplatin Activity by CEP-6800, a Poly(ADP-Ribose) Polymerase Inhibitor" Mol Cancer Ther 2003, vol. 2: 371-382.
Tokime et al., "Enhanced Poly(ADP-ribosyl)ation After Focal Ischemia in Rat Brain" J Cereb Blood Flow Metab 1998, vol. 18: 991-997.
Zhang et al., "Nitric Oxide Activation of Poly(ADP-Ribose) Synthetase in Neurotoxicity" Science 1994, vol. 263: 687-689.
Eliasson et al., "Poly(ADP-ribose) polymerase gene disruption renders mice resistant to cerebral ischemia" Nature Med 1997, vol. 3: 1089-1096.
Takahashi et al., "Post-treatment with an inhibitor of polyADP-ribose. polymerase attenuates cerebral damage in focal ischemia" Brain Res 1997, vol. 829: 46-54.
Endres et al., "Ischemic Brain Injury is Mediated by the Activation of Poly(ADP-Ribose )Polymerase" J Cereb Blood Flow Metab 1997, vol. 17: 1143-1151.
Lo et al., "Inhibition of Poly(ADP-Ribose) Polymerase: Reduction of Ischemic Injury and Attenuation of N-Methyl-d-Aspartate-Induced Neurotransmitter Dysregulation" Stroke 1998, vol. 29: 830-836.
Wang, "Mice lacking ADPRT and poly(ADP-ribosyl)ation develop normally but are susceptible to skin disease" Genes Dev 1995, vol. 9: 509-520.
Whalen et al., "Reduction of Cognitive and Motor Deficits After Traumatic Brain Injury in Mice Deficient in Poly(ADP-Ribose) Ribose) Polymerase" J Cereb Blood Flow Metab 1999, vol. 19: 835-842.
Scott et al., "Peroxynitrite Production and Activation of Poly(Adenosine Diphosphate-Ribose) Synthetase in Spinal Cord Injury" Ann Neurol 1999, vol. 45: 120-124.
Thiemermann et al., "Inhibition of the activity of poly(ADP ribose) synthetase reduces ischemia—reperfusion injury in the heart and skeletal muscle" Proc Nat Acad Sci 1997, vol. 94: 679-683.
Zingarelli et al., "Protection against myocardial ischemia and reperfusion injury by 3-aminobenzamide, an inhibitor of poly (ADP-ribose) synthetase" Cardiovascular Research 1997, vol. 36: 205-215.
Gilad et al., "Protection by Inhibition of Poly(ADP-ribose) Synthetase Against Oxidant Injury in Cardiac Myoblasts in Vitro" J Mol Cell Cardiol 1997, vol. 29: 2585-2597.
Yang et al., "Effect of Genetic Disruption of Poly (ADP-Ribose) Synthetase on Delayed Ptoduction of Inflammatory Mediators and Delayed Necrosis During Myocardial Ischemia-reperfusion Injury" Shock 2000, vol. 13: 60-66.
Cuzzocrea et al., "Protective effects of 3-aminobenzamide, an inhibitor of poly(ADP-ribose) synthase in a carrageenan-induced model of local inflammation" Eur J Pharmacology 1998, vol. 342: 67-76.
Heller et al., "Inactivation of the Poly(ADP-ribose) Polymerase Gene Affects Oxygen Radical and Nitric Oxide Toxicity in Islet Cells" J Biol Chem 1995, vol. 270: 11176-11180.
Jagtap et al., "Poly(ADP-Ribose) Polymerase and the Therapeutic Effects of its Inhibitors" Nature 2005, vol. 4: 421-440.
Hattori et al., "Rational Approaches to Discovery of Orally Active and Brain-Penetrable Quinazolinone Inhibitors of Poly (ADP-ribose)polymerase" J Med Chem 2004, vol. 47: 4151-4154.
Menear et al., "4-[3-(4-Cyclopropanecarbonylpiperazine-1-carbonyl)-4-fluorobenzyl]-2H-phthalazin-1-one: A Novel Bioavailable Inhibitor of Poly(ADP-ribose) Polymerase-1" J Med Chem 2008, vol. 51: 6581-6591.

* cited by examiner

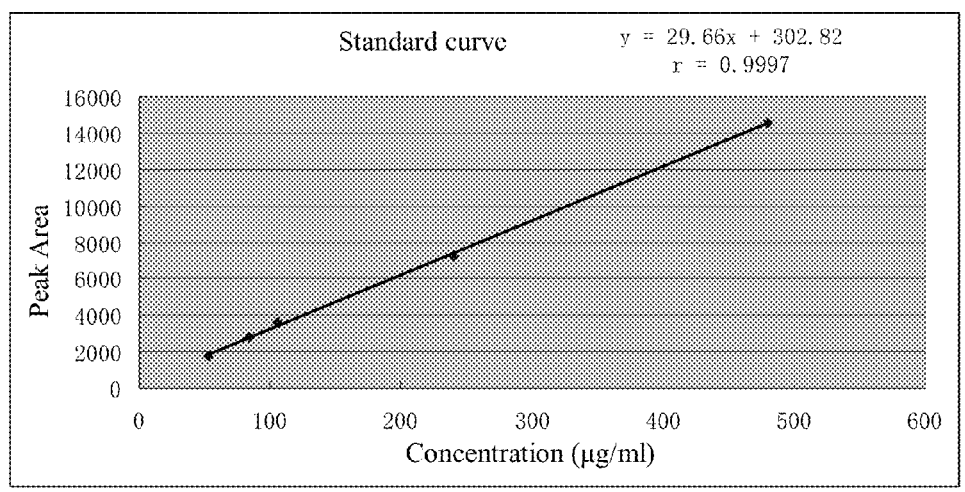

POLY (ADP-RIBOSE) POLYMERASE INHIBITOR

FIELD OF THE INVENTION

The present invention relates to poly (ADP-ribose) polymerase inhibitors comprising phthalic hydrazide (phthalazine ketone) compounds, compositions thereof, and use in the manufacture of medicaments for treating PARP enzyme activity associated diseases.

BACKGROUND OF THE INVENTION

Poly (ADP-ribose) polymerase (PARP) is a nuclear enzyme that catalyzes poly (ADP-ribosyl)ation, which is one of the important post-translational modifications in eukaryotic cells. Since its discovery over 40 years, PARP has attracted many scholars' attention due to its importance in repair of DNA damage and maintenance of genomic stability. In particular, encouraging progress has been made in the relationship between PARP and tumorigenesis and the improvement of tumor therapy by regulating PARP.

Recent studies have revealed that the PARP family comprises at least subtypes including PARP-1, PARP-2, PARP-3, PARP-4/VPARP, tankyrases (TANK-1, TANK-2 and TANK-3). In human genome, a total of 16 different genes encode PARP superfamily members, all of which have a highly conservative PARP catalytic domain consisting of 50 amino acid residues. Except the conservative PARP catalytic domain, the PARP superfamily members have different primary structures, intracellular locations and specific substrates, indicating that poly (ADP-ribose) is a post-transcriptional regulation protein with different biological functions.

PARP-1 is a polypeptide consisting of 1014 amino acid residues with a molecular weight of 113 kDa and an isoelectric point of 8.0~9.8. It is the first PARP family member discovered and is best characterized in the family. The PARP-1 polypeptide comprises 3 functional domains. (1) An N-terminal DNA binding domain (DBD, 46 kDa) that ranges from amino acid residues 1~372 comprises a nuclear localization sequence (NLS) and two Zn finger motifs. These two Zn finger motifs participate in the DNA gap recognition. The first Zn finger motif recognizes DNA single and double-strand breaks, and its mutation will greatly reduce the activation of PARP; the second Zn finger motif only participates in the recognition of DNA single-strand breaks. (2) An automodification domain (22 kDa) that ranges from amino acid residues 374-525, through which PARP-1 binds to ADP ribose and becomes self-glycosylated. The automodification domain may also lead to dimerization of PARP-1. (3) A C-terminal catalytic domain (54 kDa) that ranges from amino acid residues 524-1014 provides the basis to convert NAD into an ADP ribose. The sequence of the catalytic domain is highly conservative, especially the segment of amino acid residues 859-908, which is 100% conservative in vertebrate. The catalytic domain consists of two parts, wherein amino acid residues 662-784 form six α-helixes of A, B, C, D, E, F, which is a unique structure of PARP. The helix region binds to the active region, namely the NAD binding site through F α-helix, which probably relates to the transduction of activation signals. In addition, studies have found that PARP also comprises a leucine zipper structure, which is presumed to play a role in the homodimerization or heterodimerization of PARP.

PARP-1 participates in the DNA gap recognition. After the DNA gap recognition, activated PARP-1 forms homodimers and catalyzes the cleavage process of $NAD^+$, which converts into nicotinamide and ADP ribose, the later was used as the substrate for poly-(ADP-ribosyl)ation of nuclear receptor proteins. The activation of PARP-1 is positively correlated with the degree of DNA damage. PARP-1 activity may also be regulated through a negative feedback by self-repair during the poly (ADP-ribosyl)ation induced by DNA damage, forming a DNA damage-stimulated PARP-1 active cycle. Studies on PARP-1 inhibition and knock-out mice confirmed that PARP-1 plays a critical role in the maintenance of genomic stability.

PARP is abundant in human cells, especially in the immune cells and germ cells. Poly (ADP-ribosyl)ation occurs in many physiological processes. The multiple roles of PARP comprise chromatin degradation, DNA replication, DNA repair, gene expression, cell division, differentiation, and apoptosis.

Upon DNA damage, the PARP-1 enzyme is activated and binds to the DNA to catalyze the ribosylation of poly adenosine diphosphate, and thus initiates the process of DNA damage control and repair. On the other hand, overreaction of PARP-1 could lead to the depletion of $NAD^+$/ATP and eventually lead to cell necrosis. The apparently contradictory dual role of PARP-1 has attracted the broad interest of biologists and pharmaceutical chemists. As a result, small molecule inhibitors of PARP-1 have been widely investigated for anti-tumor therapy, nerve injury inhibition and inflammation injury. It is of great significance to discover and seek PARP-1 inhibitors.

At the molecular level, the strategies for most cancer therapies, e.g. radiotherapy and chemotherapy, kill the tumor cells by damaging the cancer cells' DNA. Accordingly, targeted therapies involved in the recognition, reaction and repair of DNA damage have been the research hotspot in recent years. PARP-1 plays an important role in DNA repair, cell death, proliferation and differentiation. It is hypothesized that the inhibition of PARP-1 activity may result in the inhibition of PARP-1-mediated repair of DNA damage, enhancing the damage of radiotherapy and chemotherapy to tumor cell DNA. Therefore, PARP-1 is of potential therapeutic value in tumor therapy.

Currently, a variety of PARP-1 inhibitors, for example, BSI-201, AZD-2281, ABT-888, NU1025, GP115427, AG014699, CEP-6800, AG14361 and INO1001, etc. have entered clinical trials. Among these PARP-1 inhibitors, AZD-2281 (olaparib/KU-59436) developed by AstraZeneca is an oral small molecule inhibitor of PARP-1, mainly used to treat ovarian cancer, breast cancer and solid tumors. In April 2009, AstraZeneca reported that AZD-2281 alone showed significant inhibitory activity for gastric cancer with good tolerance in Phase I clinical trial. At present, the research of AZD-2281 in combination with cisplatin, carboplatin, paclitaxel for solid tumors treatment is in Phase II clinical trial stage, and the clinical study mainly targeting hereditary breast and ovarian cancer has entered Phase III clinical trials. In addition, a novel PARP-1 inhibitor AG014699 developed by Pfizer is a promising malignant melanoma drug in combination with alkylating agent TMZ, and this compound has entered Phase II clinical trials.

The PARP-1 inhibitors, used alone or in combination with other chemotherapy or radiotherapy, have made important progress in the therapeutic studies in molecular, cellular and organism level in chemotherapy. Many studies have found that PARP-1 inhibitors can strengthen the effects of various antineoplastic drugs (e.g. alkylating agents, topoisomerase inhibitors). Tentori et al. (Blood 2002, vol. 99: 2241) found that NU1025 can prolong the survival of the mice bearing brain lymphoma. Delaney et al. (Clin Cancer Res 2000, vol. 6: 2860) used 12 human tumor cell lines (representing lung, colon, ovarian and breast tumor, each comprising 3 cell lines) and found that the combination of PARP-1 inhibitors NU1025 or NU10285 with antineoplastic drugs alkylating agent (temozolomide, TMZ) or camptothecin (topotecan, TP) can enhance their inhibition of tumor cell growth. The tumor-inhibition enhancement effect of NU1025 and NU10285 correlates to their strength of PARP-1 inhibition. The PARP-1 inhibitor GPI15427 developed by Guilford Inc. can enhance the effect of TMZ and significantly prolong the survival of the mice bearing glioblastoma multiforme, cerebral lymphoma or intracranial malignant melanoma. Studying on the mice subcutaneously transplanted with colon cancer cells, Calabrese et al. (J Natl Cancer Inst 2004, vol. 96: 56) found that AG14361 enhanced the antineoplastic effect of TMZ. Miknyoczki et al. (Mol Cancer Ther 2003, vol. 2: 371) treated the xenograft models corresponding to clinically obtained tumor (i.e. U251MG human glioblastoma, HT29 human colon adenocarcinoma and Calu-6 non-small cell lung cancer) with PARP-1 inhibitor CEP-6800 combined with TMZ, CPT-11 (camptothecin) or cisplatin, showing that CEP-6800 can increase the time and/or percentage of the G2/M phase arrest of the tumor cells treated with TMZ, CPT-11 or cisplatin, and enhance the therapeutic effects of TMZ, CPT-11 and cisplatin on the tumor-bearing nude mice.

Although the studies on the combination of PARP-1 inhibitors and chemotherapy showed significant enhancement in anti-tumor effects, people still concerns about its safety and feasibility. Miknyoczki et al. has found that the therapeutic dose of CEP-6800 did not increase the damage of the three chemotherapy drugs to the isolated human intestinal epithelial and kidney cells, or increase the TMZ gastrointestinal toxicity and cisplatin nephrotoxicity to the living mice, which indicates that the combination of CEP-6800 and chemotherapy is valuable and feasible. Moreover, PARP-1 inhibitor GPI15427 can achieve effective concentration in target tissue by oral administration due to its long half-life and high bioavailability, and a combination treatment of GPI15427 and TMZ on models of central nervous system tumor could achieve good therapeutic efficacy.

Some reports demonstrated that the activation of PARP plays a role in cell death in a number of disease states, suggesting that PARP inhibitors would have therapeutic efficacy in those conditions. For example, enhanced poly(ADP-ribosyl)ation has been observed following focal cerebral ischemia in the stroke rat, it indicated that the PARP was activated (Tokime et al. J. Cereb. Blood Flow Metab. 1998, vol. 18, 991). A substantial body of published pharmacological and genetic data supports the hypothesis that PARP-1 inhibitors would be neuroprotective following cerebral ischemia, or stroke. Inhibitors of PARP-1 protected against NMDA- or NO-induced neurotoxicity in rat cerebral cortical cultures (Zhang et al., Science 1994, vol. 263, 687; Eliasson et al. Nature Med. 1997, 3, 1089). it was observed that a series of PARP-1 inhibitors have protective effect on the nerve.

Suto et al. (U.S. Pat. No. 5,177,075) found that the potent PARP-1 inhibitor DPQ (3,4-dihydro-5-[4-(1-piperidinyl)butoxy]-1(2H)-isoquinolinone) provided a 54% reduction in infarct volume in a rat model of focal cerebral ischemia (permanent MCAo and 90 min bilateral occlusion of the common carotid artery) following i.p. dosing (10 mg/kg) two hours prior to and two hours after the initiation of ischemia (Takahashi et al. Brain Res. 1997, vol. 829, 46). Intracerebroventricular administration of a less potent PARP-1 inhibitor, 3-aminobenzamide (3-AB), yielded a 47% decrease in infarct volume in mice following a two hour occlusion of the MCA by the suture thread method (Endres et al. J. Cereb. Blood Flow Metab. 1997, vol. 17, 1143). Treatment with 3-AB also enhanced functional recovery 24 hours after ischemia, attenuated the decrease in NAD levels in ischemic tissues, and decreased the synthesis of poly(ADP-ribose) polymers. Similarly, 3-AB (10 mg/kg) significantly reduced infarct volume in a suture occlusion model of focal ischemia in the rat (Lo et al. Stroke 1998, vol. 29, 830). The neuroprotective effect of 3-AB (3-30 mg/kg, i.c.v.) was also observed in a permanent middle cerebral artery occlusion model of ischemia in the rat (Tokime et al. J. Cereb. Blood Flow Metab. 1998, vol. 18, 991).

The availability of PARP knockout mice (Wang, Genes Dev. 1995, vol. 9, 509) has also helped to validate the role of PARP in neurodegeneration. In the mouse suture thread model of ischemia, an 80% reduction in infarct volume was observed in PARP$^{-/-}$ biallelic knockout mice, and a 65% reduction was noted in PARP monoallelic knockout mice (PARP$^{+/-}$ mice). Endres et al. (1997) found a 35% reduction in infarct volume in PARP$^{-/-}$ mice and a 31% reduction in PARP$^{+/-}$ animals. In addition to neuroprotection, PARP$^{-/-}$ mice demonstrated an improvement in neurological score and displayed increased NAD$^+$ levels following ischemia.

Activation of PARP has been implicated in the functional deficits that may result from traumatic brain injury and spinal cord injury. In a controlled cortical impact model of traumatic brain injury, PARP$^{-/-}$ mice displayed significantly improved motor and cognitive function compared to PARP$^{+/-}$ mice (Whalen et al. J. Cereb. Blood Flow Metab. 1999, vol. 19, 835). Peroxynitrite production and PARP activation have also been demonstrated in spinal cord-injured rats (Scott et al. Ann. Neurol. 1999, vol. 45, 120). These results suggest that PARP inhibitors could avoid the loss of function following head or spinal trauma.

The role of PARP as a mediator of cell death following ischemia and reperfusion may not be limited to the nervous system. In this connection, a recent publication reported that a variety of structurally distinct PARP inhibitors, including 3-AB and related compounds, reduce infarct size following cardiac ischemia and reperfusion in the rabbit (Thiemermann et al. Proc. Nat. Acad. Sci. 1997, 94, 679). In the isolated perfused rabbit heart model, inhibition of PARP reduced infarct volume and contractile dysfunction following global ischemia and reperfusion. Skeletal muscle necrosis following ischemia and reperfusion was also attenuated by PARP inhibitors. Similar cardioprotective effects of 3-AB in a rat myocardial ischemia/reperfusion model were reported by Zingarelli and co-workers (Zingarelli et al. Cardiovascular Research 1997, 36, 205). These in vivo results are further supported by data from experiments in cultured rat cardiac myocytes (Gilad et al. J. Mol. Cell Cardiol. 1997, 29, 2585). Inhibitors of PARP (3-AB and nicotinamide) protected the myocytes from the reductions in mitochondrial respiration observed following treatment with oxidants such as hydrogen peroxide, peroxynitrite, or nitric oxide donors. The genetic disruption of PARP in mice was recently demonstrated to provide protection for delayed cellular injury and production of inflammatory mediators following myocardial ischemia and reperfusion (Yang et al. Shock 2000, 13, 60). These data support the hypothesis that administration of a PARP inhibitor could contribute to a positive outcome following myocardial infarction.

The activity of PARP is also implicated in the cellular damage that occurs in a variety of inflammatory diseases. Activation of macrophages by pro-inflammatory stimuli may result in the production of nitric oxide and superoxide anion, which combine to generate peroxynitrite, resulting in formation of DNA single-strand breaks and activation of PARP. The role of PARP as a mediator of inflammatory disease is supported by experiments employing PARP inhibitors in a number of animal models. The PARP inhibitor 5-iodo-6-amino-1,2-benzopyrone reduced the incidence and severity of arthritis in these animals, decreasing the severity of necrosis and hyperplasia of the synovium. In the carrageenan-induced pleurisy model of acute local inflammation, 3-AB inhibited the histological injury, pleural exudate formation and mononuclear cell infiltration characteristic of the inflammatory process (Cuzzocrea et al., Eur. J. Pharmacology 1998, 342, 67).

Furthermore, PARP inhibitors appear to be useful for treating diabetes. In diabetic patients, the blood glucose concentration maintains at a high level for a long term, which disrupts the endothelial cell stability. For example, hyperglycemia will cause the release of the oxidation medium (e.g. NADH/NADPH oxidase) from the mitochondrial electron-transport chain, and enhance the iNOS expression level, leading to the excessive release of vascular endothelial iNOS. The peroxides and superoxides produced by these processes lead to DNA damage, which activates PARP and depletes cellular $NAD^+$, thus triggers a series of pathological processes that lead to the dysfunction of the entire cell and eventually cell death. Heller et al., "*Inactivation of the Poly (ADP-Ribose)Polymerase Gene Affects Oxygen Radical and Nitric Oxide Toxicity in Islet Cells,*" J. Biol. Chem., 270:19, 11176-80 (May 1995), discusses the tendency of PARP to deplete cellular $NAD^+$ and induce the death of insulin-producing islet cells. Heller et al. used cells from mice with inactivated PARP genes and found that these mutant cells did not show NAD+ depletion after exposure to DNA-damaging radicals. The mutant cells were also found to be more resistant to the toxicity of NO.

Recent comprehensive review of the prior art has been published by Jagtap and Szabo in Nature 2005, vol 4: 421. Various PARP inhibitors have been reported in the following references, Hattori et al., J Med Chem 2004, vol. 47: 4151 and Menear et al., J Med Chem 2008, vol. 51: 6581. "PARP inhibitor" has also become as the key words for a number of patents including: WO 99/11645, WO 00/32579, WO 02/36599, WO 02/36599, WO 03/103666, WO 03/063874, WO 2004/096779, WO 2005/023246, WO 2005/054210, WO 2006/003148, WO 2007/138355, WO 2008/017883, US 2004/0248931, US 2006/0063926 and US 2007/0093489, etc.

DETAILED DESCRIPTION OF THE INVENTION

An objective of the present invention is to provide phthalic hydrazide (phthalazine ketone) compounds, pharmaceutically acceptable salts, hydrates, solvates or stereoisomers thereof as novel poly (ADP-ribose) polymerase inhibitors.

Another objective of the present invention is to provide pharmaceutical compositions comprising the compounds, pharmaceutically acceptable salts, hydrates, solvates or stereoisomers thereof of the present invention.

Yet another objective of the present invention is to provide use of the compounds of the present invention in the manufacture of medicaments for treating diseases associated with PARP enzyme activity, including cancers, neurodegenerative diseases, cardiovascular diseases, diabetes and inflammation.

A further objective of the present invention is to provide methods for treating diseases associated with PARP enzyme activity by using the compounds, pharmaceutically acceptable salts, hydrates, solvates or stereoisomers thereof of the present invention.

Therefore, according to one aspect of the present invention, a compound represented by Formula (I):

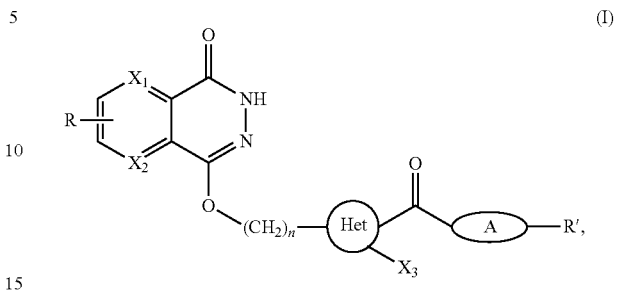

pharmaceutically acceptable salts, hydrates, solvates or stereoisomers thereof are provided, wherein:

R is selected from hydrogen, chloro, fluoro, bromo, iodo, nitro, hydroxy, amino, branched or straight-chain $C_1$-$C_6$ alkyl, haloalkyl, $CF_3$, CN, $NR^{11}R^{12}$, NH—CO—$R^{13}$ and O—$C_1$-$C_4$ alkyl, wherein $R^{11}$ and $R^{12}$ are each independently hydrogen or $C_1$-$C_4$ alkyl, $R^{13}$ is hydrogen, $C_1$-$C_4$ alkyl, $C_1$-$C_4$ alkyl-phenyl or benzene;

$X_1$, $X_2$ are each independently selected from —CH or —N, but they are not —N simultaneously;

$X_3$ is selected from hydrogen, chloro, fluoro, bromo and iodo;

Het is:

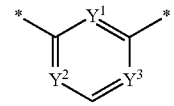

wherein $Y^1$ is selected from CH and N, $Y^2$ is selected from CH and N, and $Y^3$ is selected from CH, CF and N; wherein $Y^1$, $Y^2$, $Y^3$ may be N simultaneously, or only one or two are N;

A ring is 4~9-membered saturated or unsaturated monocyclic heterocyclic ring;

R' is selected from —C(O)$R_1$, —C(O)$NR_1$, —$CO_2R_1$, alkyl, cycloalkyl, cycloalkenyl, alkoxy, alkenyloxy, saturated or unsaturated monocyclic heterocyclic ring, aryl and heteroaryl;

R1 is selected from alkyl, cycloalkyl, cycloalkenyl, alkoxy, alkenyloxy, saturated or unsaturated monocyclic heterocyclic ring, aryl, heteroaryl and tert-butyl;

n is selected from 0~12;

each alkyl, aryl, cycloalkyl, heteroaryl, saturated or unsaturated monocyclic heterocyclic ring and tert-butyl present in the compound structure can be optionally substituted with one or more halogen, hydroxy, cyano, amino, imino, ether, nitro, nitroso, sulfydryl, thioether, sulfoxide, sulfonyl, thioamido, sulfonamido, carboxylic acid, aryl, heteroaryl, $C_{1-20}$ straight or branched chain alkyl, $C_{1-20}$ straight or branched chain alkenyl, acyl, acyloxy, amide, acylamide, ureido, alkylamino, ester, phenoxy, benzyloxy, $C_{3-20}$ cycloalkyl, $C_{5-20}$ cycloalkenyl, $C_{1-20}$ alkoxy, $C_{1-20}$ alkenyloxy, $C_{1-20}$ alkylthiol or $C_{1-20}$ haloalkyl;

and a heteroatom of the aforementioned heteroaryl and saturated or unsaturated monocyclic heterocyclic ring comprises N, O and S.

According to another aspect of the present invention, a compound, pharmaceutically acceptable salts, hydrates, solvates or stereoisomers thereof are provided, wherein the compound is represented by Formula (I):

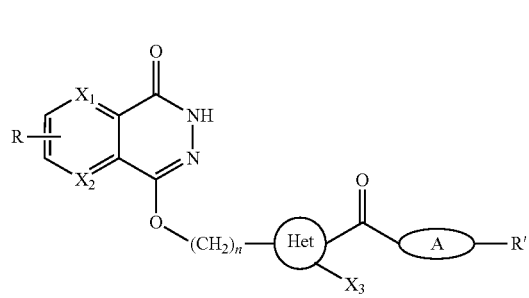

(I)

wherein:

R is selected from the group consisting of hydrogen, chloro, fluoro, bromo, iodo, nitro, hydroxy, amino, branched or straight-chain $C_1$-$C_6$ alkyl, haloalkyl, $CF_3$, CN, $NR^{11}R^{12}$, NH—CO—$R^{13}$ and O—$C_1$-$C_4$ alkyl, wherein $R^{11}$ and $R^{12}$ are each independently hydrogen or $C_1$-$C_4$ alkyl, $R^{13}$ is hydrogen, $C_1$-$C_4$ alkyl, $C_1$-$C_4$ alkyl-phenyl or benzene;

$X_1$, $X_2$ are each independently selected from —CH or —N, but they are not —N simultaneously;

$X_3$ is selected from hydrogen, chloro, fluoro, bromo and iodo;

H ring is:

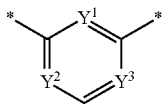

wherein $Y^1$ is selected from CH and N, $Y^2$ is selected from CH and N, and $Y^3$ is selected from CH, CF and N;

A ring is 4~9-membered saturated or unsaturated monocyclic heterocyclic ring;

R' is selected from the group consisting of —H, —C(O)$R_1$, —C(O)$NR_1$, —$CO_2R_1$, alkyl, cycloalkyl, cycloalkenyl, alkoxy, alkenyloxy, saturated or unsaturated monocyclic heterocyclic ring, aryl and heteroaryl;

R1 is selected from the group consisting of alkyl, cycloalkyl, cycloalkenyl, alkoxy, alkenyloxy, saturated or unsaturated monocyclic heterocyclic ring, aryl and heteroaryl;

n is an integer selected from 0~12;

any one of the alkyl, aryl, cycloalkyl, heteroaryl, saturated or unsaturated monocyclic heterocyclic ring and tert-butyl is optionally substituted with one or more substituents selected from the group consisting of halogen, hydroxy, cyano, amino, imino, ether, nitro, nitroso, sulfydryl, thioether, sulfoxide, sulfonyl, thioamido, sulfonamido, carboxylic acid, aryl, heteroaryl, $C_{1-20}$ straight or branched chain alkyl, $C_{1-20}$ straight or branched chain alkenyl, acyl, acyloxy, amide, acyl amide, ureido, alkylamino, ester, phenoxy, benzyloxy, $C_{3-20}$ cycloalkyl, $C_{5-20}$ cycloalkenyl, $C_{1-20}$ alkoxy, $C_{1-20}$ alkenyloxy, $C_{1-20}$ alkylthiol and $C_{1-20}$ haloalkyl; and a heteroatom of the aforementioned heteroaryl and saturated/or unsaturated monocyclic heterocyclic ring is selected from N, O and S.

For the aforementioned substituents comprising amino such as C(O)$NR_1$, alkylamino, etc., the substitution of N with $R_1$ or alkyl may be monosubstitution or double substitution, and the two substituents in the double substitution may be the same or different.

According to a preferred embodiment of the present invention, H ring is:

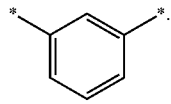

In that case, the preferred A ring is substituted or unsubstituted 4-9-membered saturated or unsaturated monocyclic heterocyclic ring comprising 1-3 heteroatoms selected from N, O and S; and R' is selected from the group consisting of —H, —C(O)$R_1$, —C(O)$NR_1$, —$CO_2R_1$, substituted or unsubstituted $C_{1-10}$ alkyl, substituted or unsubstituted $C_{2-10}$ alkenyl, substituted or unsubstituted $C_{3-10}$ cycloalkyl, substituted or unsubstituted $C_{5-10}$ cycloalkenyl, substituted or unsubstituted $C_{1-10}$ alkoxy, substituted or unsubstituted $C_{1-10}$ alkenyloxy, substituted or unsubstituted 3-10-membered saturated or unsaturated monocyclic heterocyclic ring comprising 1-3 heteroatoms selected from N, O and S, substituted or unsubstituted $C_{6-10}$ aryl and substituted or unsubstituted $C_{5-10}$ heteroaryl comprising 1-3 heteroatoms selected from N, O and S. And wherein $R_1$ is selected from the group consisting of substituted or unsubstituted $C_{1-10}$ alkyl, substituted or unsubstituted $C_{2-10}$ alkenyl, substituted or unsubstituted $C_{3-10}$ cycloalkyl, substituted or unsubstituted $C_{5-10}$ cycloalkenyl, substituted or unsubstituted $C_{1-10}$ alkoxy, substituted or unsubstituted $C_{2-10}$ alkenyloxy, substituted or unsubstituted 3-10-membered saturated or unsaturated monocyclic heterocyclic ring comprising 1-3 heteroatoms selected from N, O and S, substituted or unsubstituted $C_{6-10}$ aryl and substituted or unsubstituted $C_{5-10}$ heteroaryl comprising 1-3 heteroatoms selected from N, O and S. Wherein the substitution refers to substitution by at least one group selected from the group consisting of halogen, hydroxy, cyano, amino, carboxyl, $C_{2-10}$ hydrocarbyl ether, nitro, $C_{1-10}$ hydrocarbyl sulfonyl, $C_{1-10}$ hydrocarbyl sulfonamide, $C_{6-10}$ aryl, $C_{5-10}$ heteroaryl comprising 1-3 heteroatoms selected from N, O and S, $C_{1-10}$ straight or branched chain alkyl, $C_{1-10}$ straight or branched chain alkenyl, $C_{1-10}$ hydrocarbyl acyl, $C_{1-10}$ hydrocarbyl acyloxy, $C_{1-10}$ hydrocarbyl amide, $C_{1-10}$ hydrocarbyl acyl amide, ureido, ($C_{1-10}$ alky)$_{1-2}$ amino, $C_{1-10}$ hydrocarbyl ester, phenoxy, benzyloxy, $C_{3-10}$ cycloalkyl, $C_{5-10}$ cycloalkenyl, $C_{1-10}$ alkoxy, $C_{1-10}$ alkenyloxy, $C_{1-10}$ alkylthiol and $C_{1-10}$ haloalkyl.

According to a further preferred embodiment, A ring can be selected from the group consisting of piperazine, homopiperazine, piperidine, tetrahydropyridine, 4-hydroxypiperidine, 2-methylpiperazine and 3-methylpiperazine.

In that case, R' is selected from the group consisting of —H, —C(O)$R_1$, —C(O)$NR_1$, —$CO_2R_1$, substituted or unsubstituted $C_{1-10}$ alkyl, substituted or unsubstituted $C_{2-10}$ alkenyl, substituted or unsubstituted $C_{6-10}$ aryl and substituted or unsubstituted $C_{5-10}$ heteroaryl comprising 1-3 heteroatoms selected from N, O and S, and wherein $R_1$ is selected from the group consisting of substituted or unsubstituted $C_{1-10}$ alkyl, substituted or unsubstituted $C_{2-10}$ alkenyl, substituted or unsubstituted $C_{3-7}$ cycloalkyl, substituted or unsubstituted $C_{5-7}$ cycloalkenyl, substituted or unsubstituted $C_{1-10}$ alkoxy, substituted or unsubstituted 5-7-membered saturated or unsaturated monocyclic heterocyclic ring comprising 1-3 heteroatoms selected from N, O and S, substituted or unsubstituted $C_{6-10}$ aryl and substituted or unsubstituted $C_{5-10}$ heteroaryl comprising 1-3 heteroatoms selected from N, O and S, wherein the substitution refers to substitution by at least one group selected from the group consisting of halogen, hydroxy, cyano, amino, nitro, $C_{6-10}$ aryl, $C_{1-10}$ straight or branched chain alkyl, $C_{1-10}$ hydrocarbyl acyloxy, ($C_{1-10}$ alky)$_{1-2}$ amino, C$_{1-10}$ hydrocarbyl ester, phenoxy, benzyloxy, C$_{3-7}$ cycloalkyl, C$_{1-10}$ alkoxy and C$_{1-10}$ haloalkyl.

According to a more preferred embodiment, the compound is represented by Formula (II) or (III):

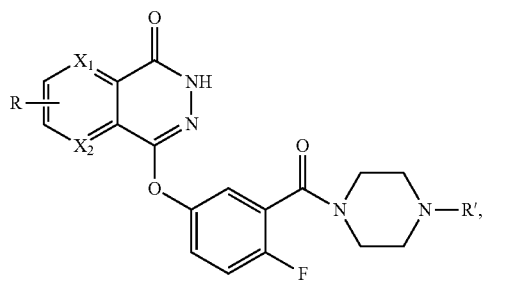

(II)

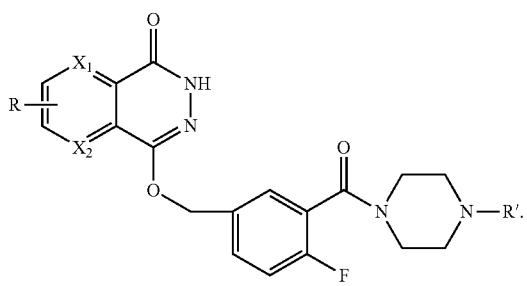

(III)

In the above Formula (II) or (III), R' is preferably —C(O)R$_1$, wherein R$_1$ is selected from the group consisting of substituted or unsubstituted C$_{3-6}$ alkyl, substituted or unsubstituted C$_{3-6}$ cycloalkyl, substituted or unsubstituted 5-6-membered saturated or unsaturated monocyclic heterocyclic ring comprising 1-2 heteroatoms selected from N, O and S, or substituted or unsubstituted phenyl, the substitution refers to substitution by at least one group selected from the group consisting of halogen, hydroxy, cyano, amino, nitro, phenyl, C$_{1-3}$ straight or branched chain alkyl, (C$_{1-3}$ alky)$_{1-2}$ amino.

In Formula (II) or (III), R is further preferably selected from the group consisting of hydrogen, fluoro, chloro, bromo, nitro and amino; and X$_1$, X$_2$ are CH, respectively.

R' is more further preferably selected from the group consisting of ethyl, propyl, butyl, pentyl, cyclopropyl, cyclobutyl, cyclohexyl, phenyl, pyrrolidinyl and piperidinyl optionally substituted by one or two substituents selected from fluoro, chloro, nitro, amino, methylamino, dimethylamino, methyl and phenyl.

The aforementioned propyl, butyl and pentyl may be straight or branched chain, and branched chain is more preferable. For example, propyl is preferably isopropyl, butyl is preferably tert-butyl, and phenyl is preferably 1-ethylpropyl.

Besides, unless otherwise specified, each of the alkyl, alkenyl and hydrocarbyl as used herein refer to straight or branched chain alkyl, alkenyl and hydrocarbyl.

In particular, the compound of Formula (I) of the present invention can be the following compounds 1-130:

| Compound No. | Structure and Nomenclature |
|---|---|
| 1 | 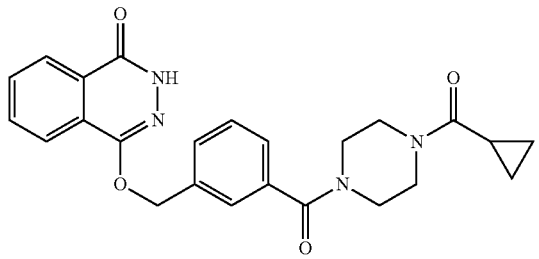 [SMILES: O=C(c1cccc(COc2n[nH]c(=O)c3ccccc23)c1)N1CCN(C(=O)C2CC2)CC1] <br> 4-(3-(4-(cyclopropanecarbonyl-piperazine-1-carbonyl)benzyloxy)-2H-phthalazin-1-one |
| 2 | 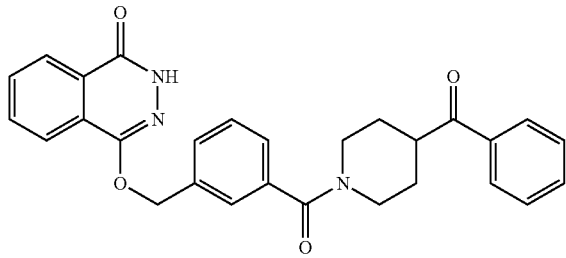 [SMILES: O=C(c1ccccc1)C1CCN(C(=O)c2cccc(COc3n[nH]c(=O)c4ccccc34)c2)CC1] <br> 4-(3-(4-benzoylpiperidine-1-carbonyl)benzyloxy)-2H-phthalazin-1-one |

| Compound No. | Structure and Nomenclature |
|---|---|
| 3 | 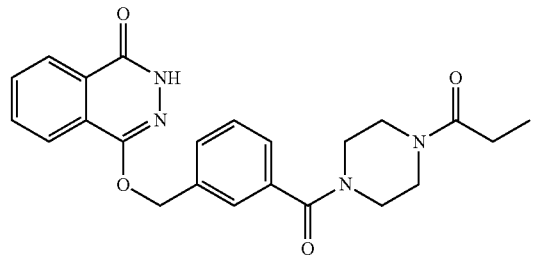 [SMILES: CCC(=O)N1CCN(C(=O)c2cccc(COc3n[nH]c(=O)c4ccccc34)c2)CC1]<br>4-(3-(4-propionylpiperazine-1-carbonyl)benzyloxy)-2H-phthalazin-1-one |
| 4 | 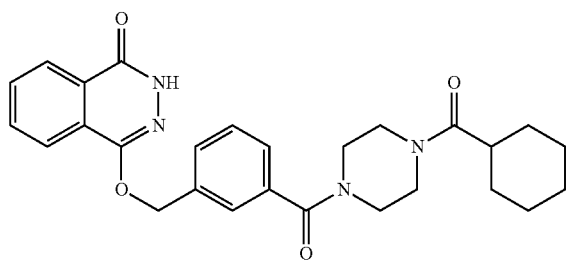 [SMILES: O=C(c1cccc(COc2n[nH]c(=O)c3ccccc23)c1)N1CCN(C(=O)C2CCCCC2)CC1]<br>4-(3-(4-(cyclohexanecarbonyl-piperazine-1-carbonyl)benzyloxy)-2H-phthalazin-1-one |
| 5 | 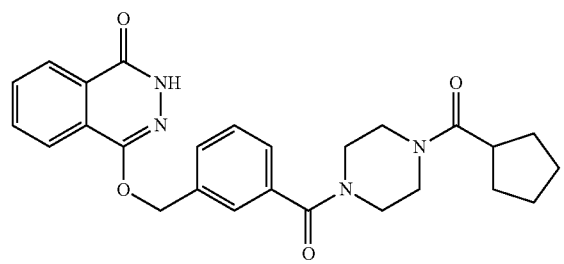 [SMILES: O=C(c1cccc(COc2n[nH]c(=O)c3ccccc23)c1)N1CCN(C(=O)C2CCCC2)CC1]<br>4-(3-(4-(cyclopentanecarbonyl-piperazine-1-carbonyl)benzyloxy)-2H-phthalazin-1-one |
| 6 | 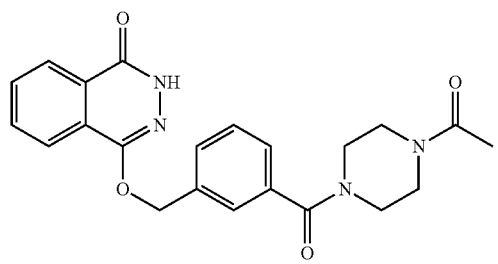 [SMILES: CC(=O)N1CCN(C(=O)c2cccc(COc3n[nH]c(=O)c4ccccc34)c2)CC1]<br>4-(3-(4-acetylpiperazine-1-carbonyl)benzyloxy)-2H-phthalazin-1-one |

| Compound No. | Structure and Nomenclature |
|---|---|
| 7 | 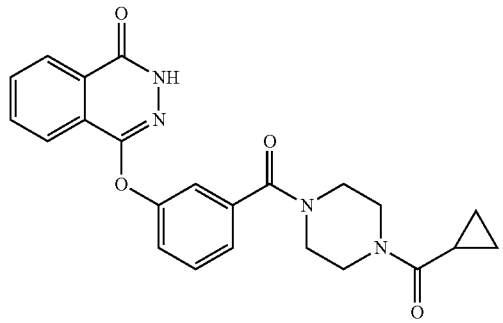 [SMILES: O=C(c1cccc(Oc2n[nH]c(=O)c3ccccc23)c1)N1CCN(C(=O)C2CC2)CC1]<br>4-(3-(4-(cyclopropanecarbonyl-piperazine-1-carbonyl)phenoxy)-2H-phthalazin-1-one |
| 8 | 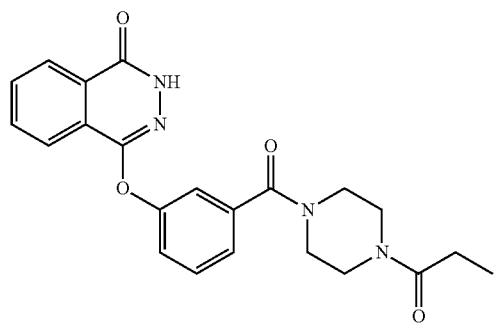 [SMILES: CCC(=O)N1CCN(C(=O)c2cccc(Oc3n[nH]c(=O)c4ccccc34)c2)CC1]<br>4-(3-(4-propionylpiperazine-1-carbonyl)phenoxy)-2H-phthalazin-1-one |
| 9 | 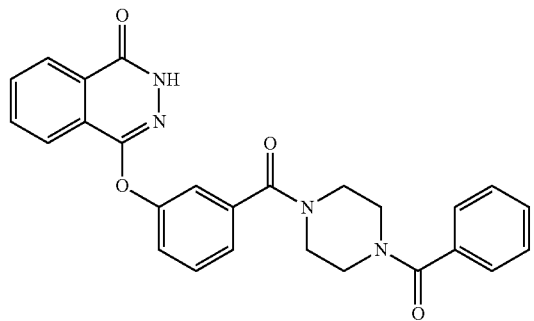 [SMILES: O=C(c1ccccc1)N1CCN(C(=O)c2cccc(Oc3n[nH]c(=O)c4ccccc34)c2)CC1]<br>4-(3-(4-benzoylpiperazine-1-carbonyl)phenoxy)-2H-phthalazin-1-one |
| 10 | 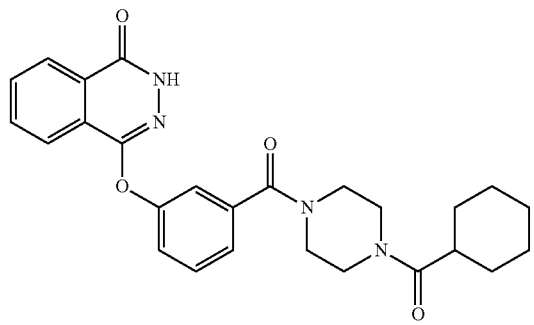 [SMILES: O=C(c1cccc(Oc2n[nH]c(=O)c3ccccc23)c1)N1CCN(C(=O)C2CCCCC2)CC1]<br>4-(3-(4-(cyclohexanecarbonyl-piperazine-1-carbonyl)phenoxy)-2H-phthalazin-1-one |

| Compound No. | Structure and Nomenclature |
|---|---|
| 11 | 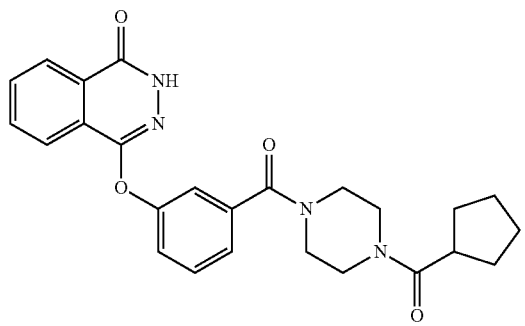 [SMILES: O=C(c1cccc(Oc2n[nH]c(=O)c3ccccc23)c1)N1CCN(C(=O)C2CCCC2)CC1]<br>4-(3-(4-(cyclopentanecarbonyl-piperazine-1-carbonyl)phenoxy)-2H-phthalazin-1-one |
| 12 | 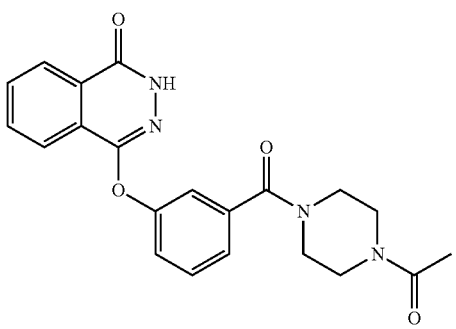 [SMILES: CC(=O)N1CCN(C(=O)c2cccc(Oc3n[nH]c(=O)c4ccccc34)c2)CC1]<br>4-(3-(4-acetylpiperazine-1-carbonyl)phenoxy)-2H-phthalazin-1-one |
| 13 | 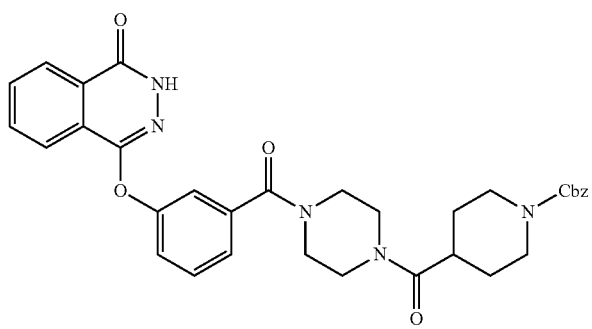 [SMILES: O=C(OCc1ccccc1)N1CCC(C(=O)N2CCN(C(=O)c3cccc(Oc4n[nH]c(=O)c5ccccc45)c3)CC2)CC1]<br>4-(3-(4-(1-benzyloxycarbonyl-piperidine)carbonylpiperazine-1-carbonyl)phenoxy)-2H-phthalazin-1-one |
| 14 | 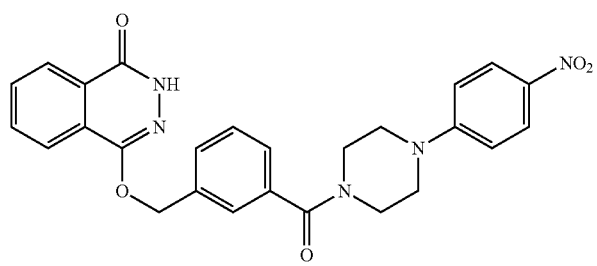 [SMILES: O=C(c1cccc(COc2n[nH]c(=O)c3ccccc23)c1)N1CCN(c2ccc([N+](=O)[O-])cc2)CC1]<br>4-(3-(4-paranitrophenylpiperazine-1-carbonyl)benzyloxy)-2H-phthalazin-1-one |

| Compound No. | Structure and Nomenclature |
|---|---|
| 15 | 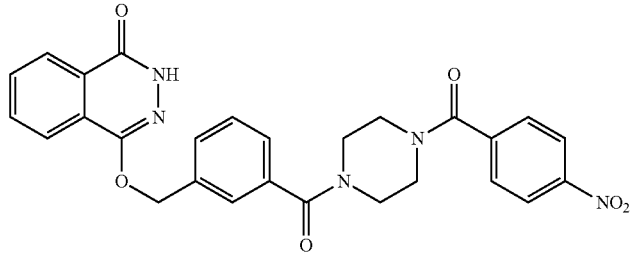 [SMILES: O=C(c1ccc([N+](=O)[O-])cc1)N1CCN(C(=O)c2cccc(COc3n[nH]c(=O)c4ccccc34)c2)CC1]<br>4-(3-(4-paranitrobenzoylpiperazine-1-carbonyl)benzyloxy)-2H-phthalazin-1-one |
| 16 | 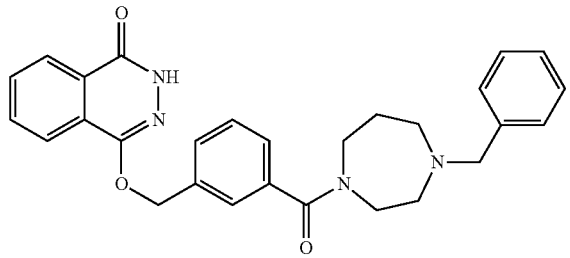 [SMILES: O=C(c1cccc(COc2n[nH]c(=O)c3ccccc23)c1)N1CCCN(Cc2ccccc2)CC1]<br>4-(3-(4-benzyl-1,4-diazacycloheptane-1-carbonyl)benzyloxy)-2H-phthalazin-1-one |
| 17 | 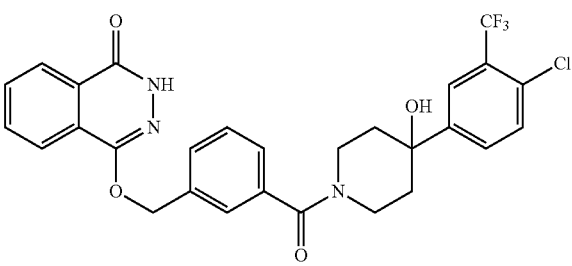 [SMILES: O=C(c1cccc(COc2n[nH]c(=O)c3ccccc23)c1)N1CCC(O)(c2ccc(Cl)c(C(F)(F)F)c2)CC1]<br>4-(3-(4-(3-chloro-4-trifluoromethyl-phenyl)-4-hydroxypiperidine-1-carbonyl)benzyloxy)-2H-phthalazin-1-one |
| 18 | 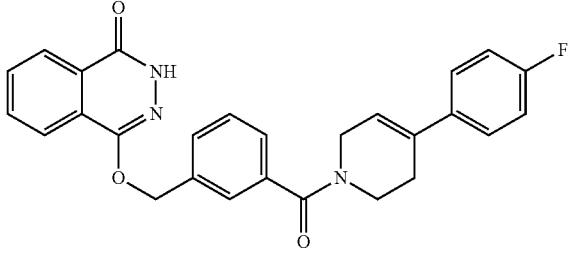 [SMILES: O=C(c1cccc(COc2n[nH]c(=O)c3ccccc23)c1)N1CC=C(c2ccc(F)cc2)CC1]<br>4-(3-(4-(4-fluorophenyl)-1,2,3,6-tetrahydropyridine-1-carbonyl)benzyloxy-2H-phthalazin-1-one |
| 19 | 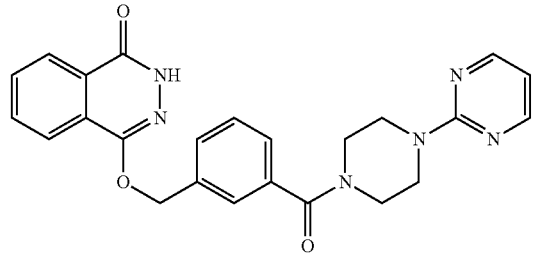 [SMILES: O=C(c1cccc(COc2n[nH]c(=O)c3ccccc23)c1)N1CCN(c2ncccn2)CC1]<br>4-(3-(4-(pyrimidine-2-yl)piperazine-1-carbonyl)benzyloxy)-2H-phthalazin-1-one |

| Compound No. | Structure and Nomenclature |
|---|---|
| 20 | 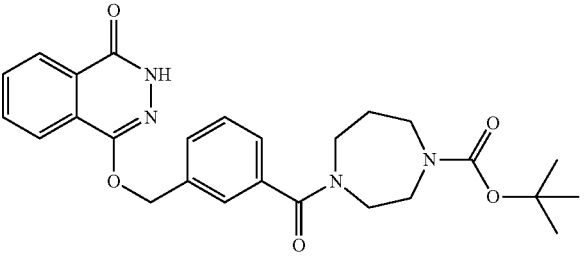 [SMILES: CC(C)(C)OC(=O)N1CCCN(C(=O)c2cccc(COc3n[nH]c(=O)c4ccccc34)c2)CC1]<br>4-(3-(4-tertbutoxycarbonyl-1,4-diazacycloheptane-1-carbonyl)benzyloxy)-2H-phthalazin-1-one |
| 21 | 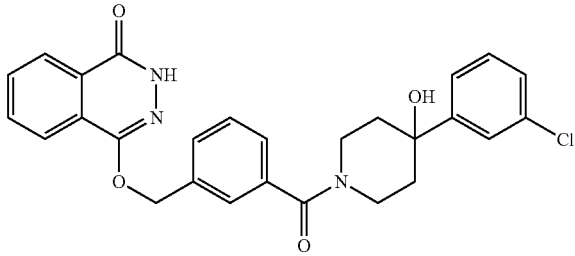 [SMILES: O=C(c1cccc(COc2n[nH]c(=O)c3ccccc23)c1)N1CCC(O)(c2cccc(Cl)c2)CC1]<br>4-(3-(4-(3-chloro-phenyl)-4-hydroxypiperidine-1-carbonyl)benzyloxy)-2H-phthalazin-1-one |
| 22 | 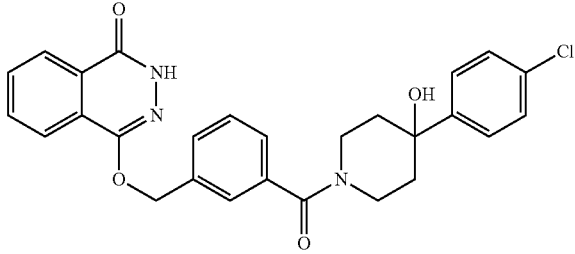 [SMILES: O=C(c1cccc(COc2n[nH]c(=O)c3ccccc23)c1)N1CCC(O)(c2ccc(Cl)cc2)CC1]<br>4-(3-(4-(4-chloro-phenyl)-4-hydroxypiperidine-1-carbonyl)benzyloxy)-2H-phthalazin-1-one |
| 23 | 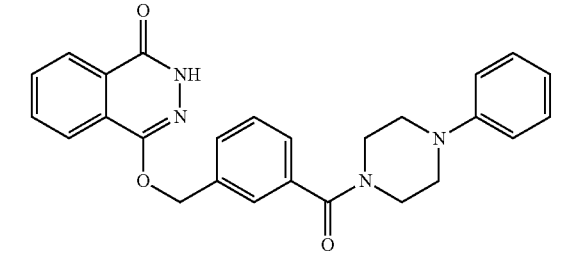 [SMILES: O=C(c1cccc(COc2n[nH]c(=O)c3ccccc23)c1)N1CCN(c2ccccc2)CC1]<br>4-(3-(4-phenylpiperazine-1-carbonyl)benzyloxy)-2H-phthalazin-1-one |
| 24 | 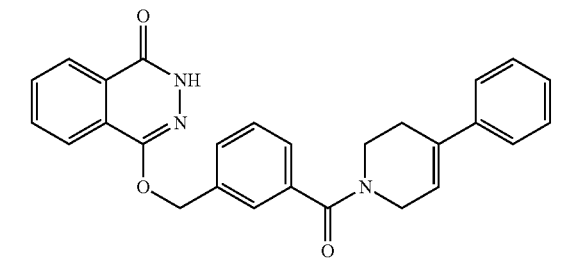 [SMILES: O=C(c1cccc(COc2n[nH]c(=O)c3ccccc23)c1)N1CC=C(c2ccccc2)CC1]<br>4-(3-(4-phenyl-1,2,3,6-tetrahydropyridine-1-carbonyl)benzyloxy)-2H-phthalazin-1-one |

| Compound No. | Structure and Nomenclature |
|---|---|
| 25 | 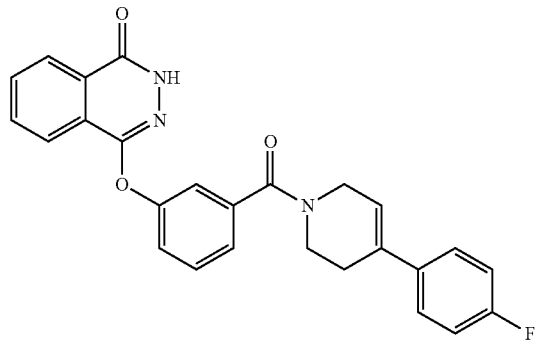 [SMILES: O=C(c1cccc(Oc2n[nH]c(=O)c3ccccc23)c1)N1CC=C(c2ccc(F)cc2)CC1]<br>4-(3-(4-(4-fluoro-phenyl)-1,2,3,6-tetrahydropyridine-1-carbonyl)phenoxy)-2H-phthalazin-1-one |
| 26 | 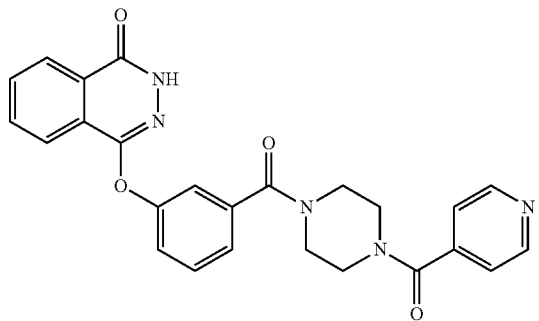 [SMILES: O=C(c1ccncc1)N1CCN(C(=O)c2cccc(Oc3n[nH]c(=O)c4ccccc34)c2)CC1]<br>4-(3-(4-isonicotinoylpiperazine-1-carbonyl)phenoxy)-2H-phthalazin-1-one |
| 27 | 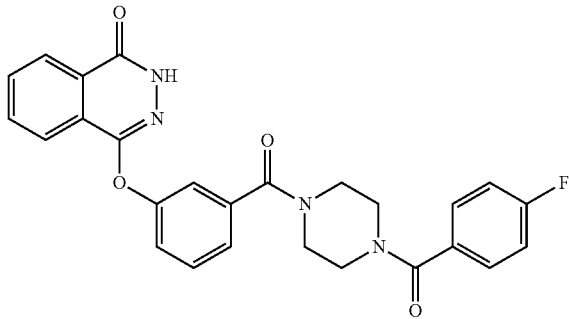 [SMILES: O=C(c1ccc(F)cc1)N1CCN(C(=O)c2cccc(Oc3n[nH]c(=O)c4ccccc34)c2)CC1]<br>4-(3-(4-(4-fluorobenzoyl)piperazine-1-carbonyl)phenoxy)-2H-phthalazin-1-one |
| 28 | 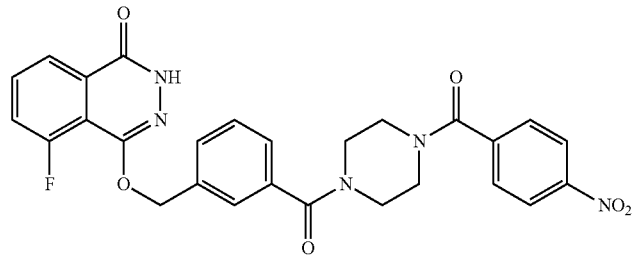 [SMILES: O=C(c1ccc([N+](=O)[O-])cc1)N1CCN(C(=O)c2cccc(COc3n[nH]c(=O)c4cccc(F)c34)c2)CC1]<br>5-fluoro-4-(3-(4-(4-nitrobenzoyl)piperazine-1-carbonyl)benzyloxy)-2H-phthalazin-1-one |

| Compound No. | Structure and Nomenclature |
|---|---|
| 29 | 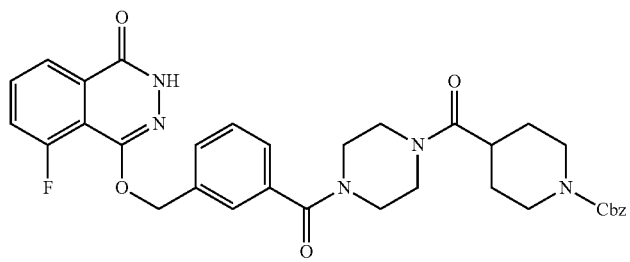 [SMILES: O=C(OCc1ccccc1)N1CCC(C(=O)N2CCN(C(=O)c3cccc(COc4n[nH]c(=O)c5cccc(F)c45)c3)CC2)CC1]<br>8-fluoro-4-(3-(4-(1-benzyloxycarbonyl-piperidine)carbonylpiperazine-1-carbonyl)phenoxy)-2H-phthalazin-1-one |
| 30 | 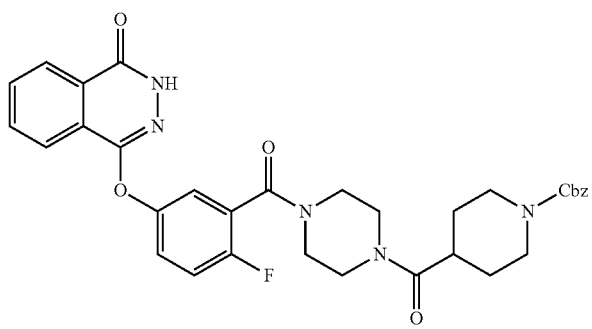 [SMILES: O=C(OCc1ccccc1)N1CCC(C(=O)N2CCN(C(=O)c3cc(Oc4n[nH]c(=O)c5ccccc45)ccc3F)CC2)CC1]<br>4-(2-fluoro-(4-(1-benzyloxycarbonyl-piperidine)carbonylpiperazine-1-carbonyl)phenoxy)-2H-phthalazin-1-one |
| 31 | 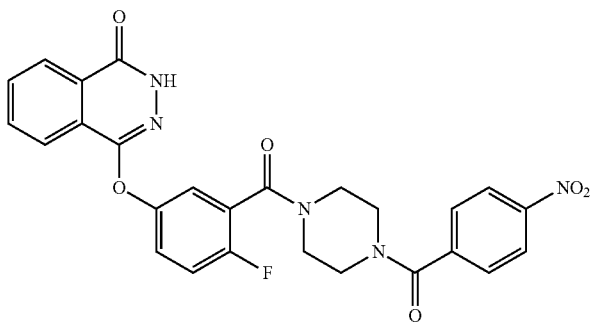 [SMILES: O=C(c1ccc([N+](=O)[O-])cc1)N1CCN(C(=O)c2cc(Oc3n[nH]c(=O)c4ccccc34)ccc2F)CC1]<br>4-(4-fluoro-3-(4-(4-nitrobenzoyl)piperazine-1-carbonyl)phenoxy)-2H-phthalazin-1-one |
| 32 | 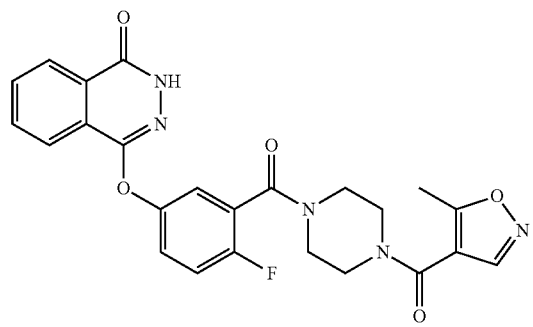 [SMILES: Cc1oncc1C(=O)N1CCN(C(=O)c2cc(Oc3n[nH]c(=O)c4ccccc34)ccc2F)CC1]<br>4-(4-fluoro-3-(4-(5-methylisoxazole-4-carbonyl)piperazine-1-carbonyl)phenoxy-2H-phthalazin-1-one |

| Compound No. | Structure and Nomenclature |
|---|---|
| 33 | 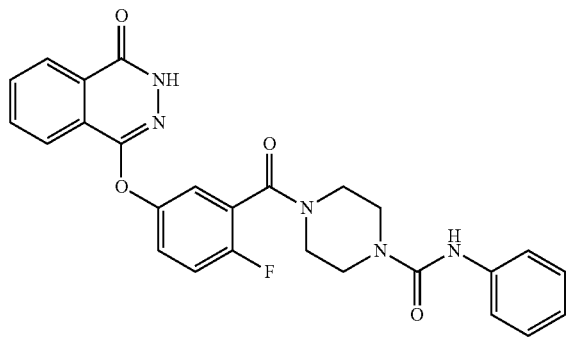 [SMILES: O=C(Nc1ccccc1)N1CCN(C(=O)c2cc(Oc3n[nH]c(=O)c4ccccc34)ccc2F)CC1]<br>4-(2-fluoro-5-(4-oxo-3,4-2H-phthalazine-1-yl-oxyl)benzoyl)-N-phenylpiperazine-1-formamide |
| 34 | 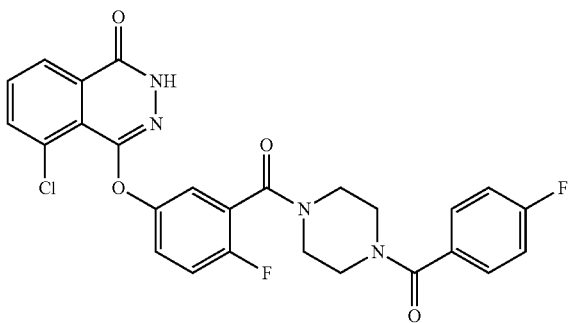 [SMILES: O=C(c1ccc(F)cc1)N1CCN(C(=O)c2cc(Oc3n[nH]c(=O)c4cccc(Cl)c34)ccc2F)CC1]<br>5-chloro-4-(4-fluoro-3-(4-(4-fluorobenzoyl)piperazine-1-carbonyl)phenoxy)-2H-phthalazin-1-one |
| 35 | 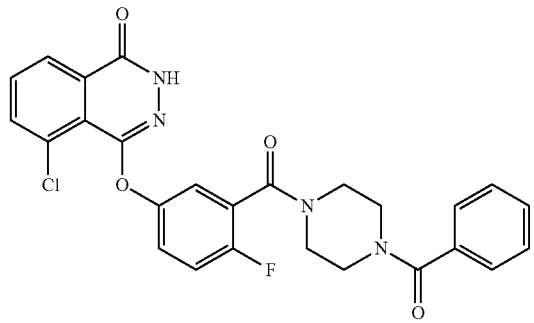 [SMILES: O=C(c1ccccc1)N1CCN(C(=O)c2cc(Oc3n[nH]c(=O)c4cccc(Cl)c34)ccc2F)CC1]<br>5-chloro-4-(4-fluoro-3-(4-benzoylpiperazine-1-carbonyl)phenoxy)-2H-phthalazin-1-one |
| 36 | 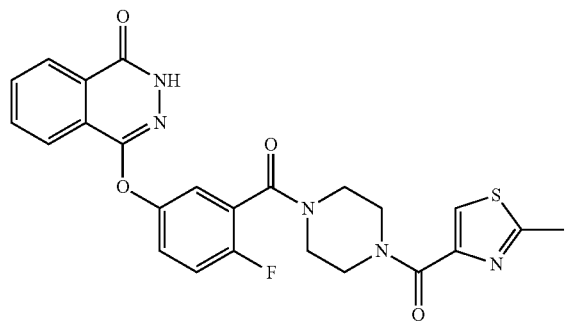 [SMILES: Cc1nc(C(=O)N2CCN(C(=O)c3cc(Oc4n[nH]c(=O)c5ccccc45)ccc3F)CC2)cs1]<br>4-(4-fluoro-3-(4-(2-methylthiazole-4-carbonyl)piperazine-1-carbonyl)phenoxy-2H-phthalazin-1-one |

| Compound No. | Structure and Nomenclature |
|---|---|
| 37 | 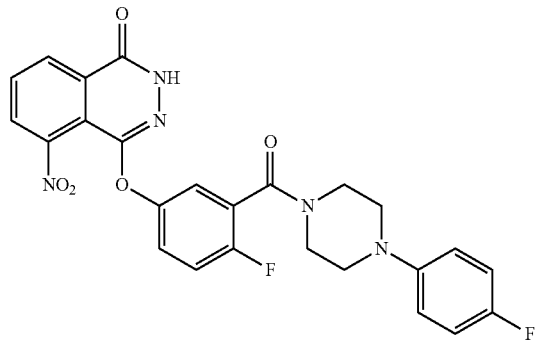 [SMILES: O=C(c1cc(Oc2n[nH]c(=O)c3cccc([N+](=O)[O-])c23)ccc1F)N1CCN(c2ccc(F)cc2)CC1]<br>4-(4-fluoro-3-(4-(4-fluorophenyl)piperazine-1-carbonyl)phenoxy)-5-nitro-2H-phthalazin-1-one |
| 38 | 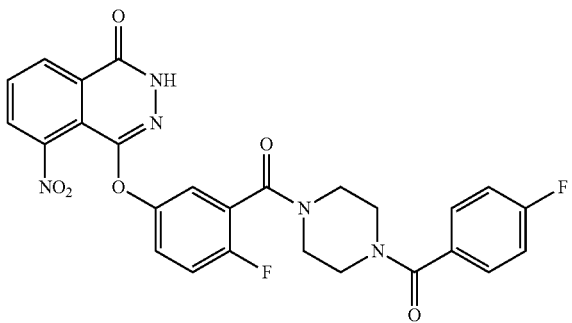 [SMILES: O=C(c1ccc(F)cc1)N1CCN(C(=O)c2cc(Oc3n[nH]c(=O)c4cccc([N+](=O)[O-])c34)ccc2F)CC1]<br>4-(4-fluoro-3-(4-(4-fluorobenzoyl)piperazine-1-carbonyl)phenoxy)-5-nitro-2H-phthalazin-1-one |
| 39 | 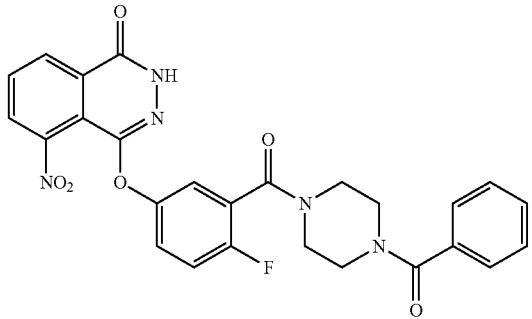 [SMILES: O=C(c1ccccc1)N1CCN(C(=O)c2cc(Oc3n[nH]c(=O)c4cccc([N+](=O)[O-])c34)ccc2F)CC1]<br>4-(4-fluoro-3-(4-benzoylpiperazine-1-carbonyl)phenoxy)-5-nitro-2H-phthalazin-1-one |
| 40 | 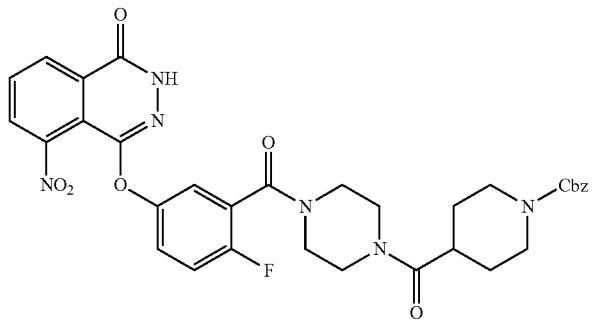 [SMILES: O=C(OCc1ccccc1)N1CCC(C(=O)N2CCN(C(=O)c3cc(Oc4n[nH]c(=O)c5cccc([N+](=O)[O-])c45)ccc3F)CC2)CC1]<br>8-nitro-4-(2-fluoro-(4-(1-benzyloxycarbonyl-piperidine)carbonylpiperazine-1-carbonyl)phenoxy)-2H-phthalazin-1-one |

| Compound No. | Structure and Nomenclature |
|---|---|
| 41 | 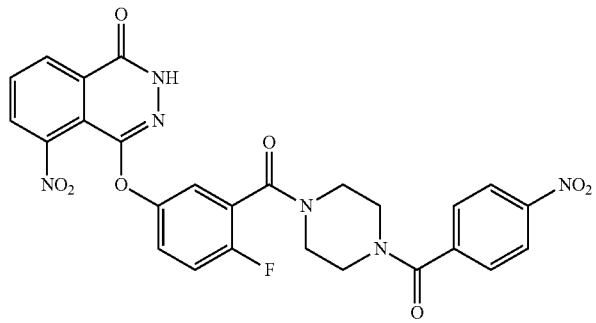<br>4-(4-fluoro-3-(4-(4-nitrobenzoyl)piperazine-1-carbonyl)phenoxy)-5-nitro-2H-phthalazin-1-one |
| 42 | 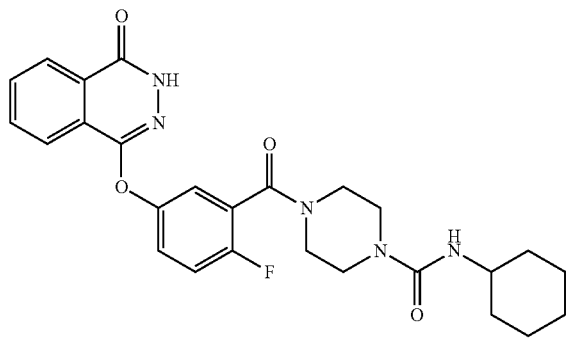 [SMILES: O=C(NC1CCCCC1)N1CCN(C(=O)c2cc(Oc3n[nH]c(=O)c4ccccc34)ccc2F)CC1]<br>N-cyclohexyl-4-(2-fluoro-5-(4-oxo-3,4-2H-phthalazine-1-yl-oxyl)benzoyl)piperazine-1-formamide |
| 43 | 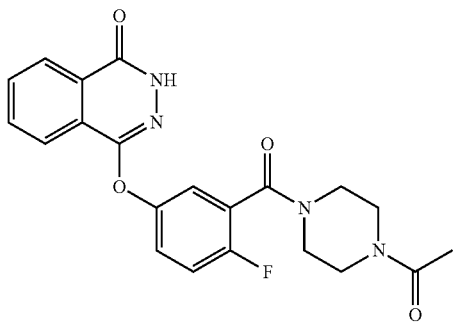 [SMILES: CC(=O)N1CCN(C(=O)c2cc(Oc3n[nH]c(=O)c4ccccc34)ccc2F)CC1]<br>4-(3-(4-acetylpiperazine-1-carbonyl)-4-fluorophenoxy)-2H-phthalazin-1-one |
| 44 | 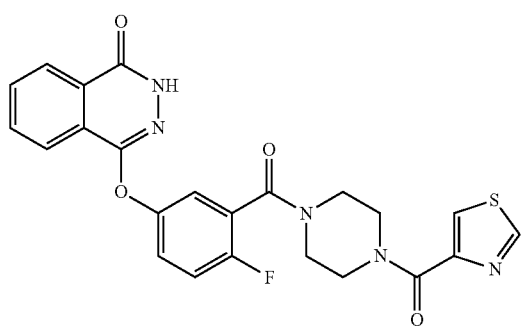<br>4-(4-fluoro-3-(4-(thiazole-4-carbonyl)piperazine-1-carbonyl)phenoxy)-2H-phthalazin-1-one |

| Compound No. | Structure and Nomenclature |
|---|---|
| 45 | 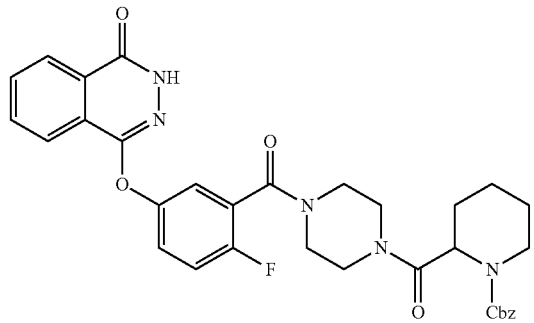 [SMILES: O=C(c1cc(Oc2n[nH]c(=O)c3ccccc23)ccc1F)N1CCN(C(=O)C2CCCCN2C(=O)OCc2ccccc2)CC1]<br>4-(2-fluoro-(4-(2-benzyloxycarbonyl-piperidine)carbonylpiperazine-1-carbonyl)phenoxy)-2H-phthalazin-1-one |
| 46 | 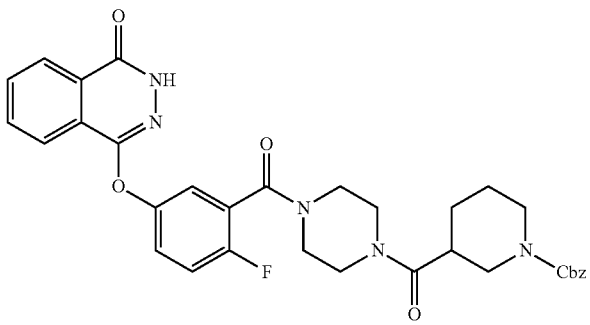 [SMILES: O=C(OCc1ccccc1)N1CCCC(C(=O)N2CCN(C(=O)c3cc(Oc4n[nH]c(=O)c5ccccc45)ccc3F)CC2)C1]<br>4-(2-fluoro-(4-(3-benzyloxycarbonyl-piperidine)carbonylpiperazine-1-carbonyl)phenoxy)-2H-phthalazin-1-one |
| 47 | 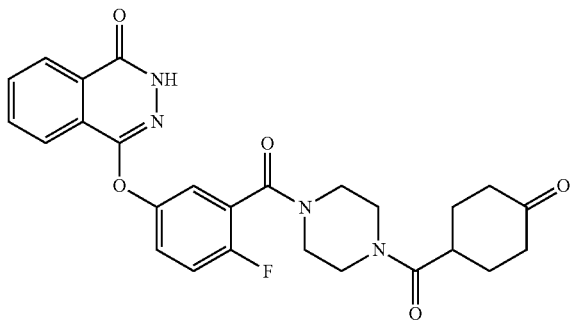 [SMILES: O=C1CCC(C(=O)N2CCN(C(=O)c3cc(Oc4n[nH]c(=O)c5ccccc45)ccc3F)CC2)CC1]<br>4-(4-fluoro-3-(4-(4-oxocyclohexanecarbonyl)piperazine-1-carbonyl)phenoxy)-2H-phthalazin-1-one |
| 48 | 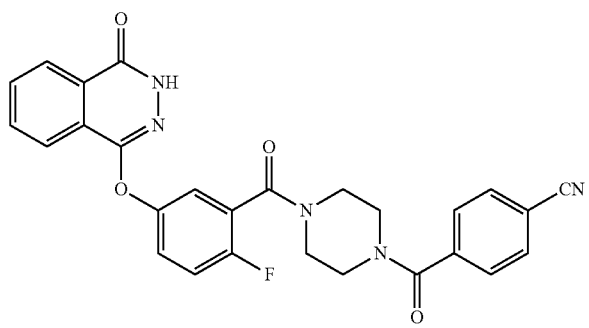 [SMILES: N#Cc1ccc(C(=O)N2CCN(C(=O)c3cc(Oc4n[nH]c(=O)c5ccccc45)ccc3F)CC2)cc1]<br>4-(4-fluoro-3-(4-(4-cyanobenzoyl)piperazine-1-carbonyl)phenoxy)-2H-phthalazin-1-one |

| Compound No. | Structure and Nomenclature |
|---|---|
| 49 | 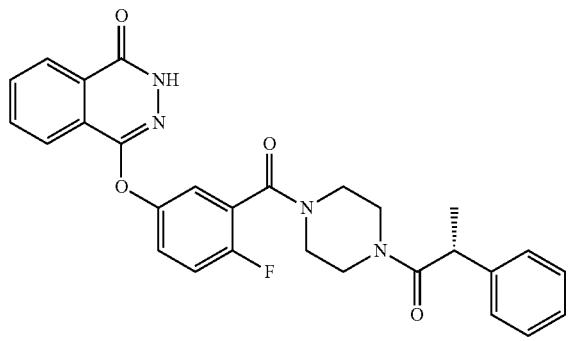 [SMILES: C[C@@H](C(=O)N1CCN(C(=O)c2cc(Oc3n[nH]c(=O)c4ccccc34)ccc2F)CC1)c1ccccc1]<br>(R)-4-(4-fluoro-3-(4-(2-phenylpropionyl)piperazine-1-carbonyl)phenoxy)-2H-phthalazin-1-one |
| 50 | 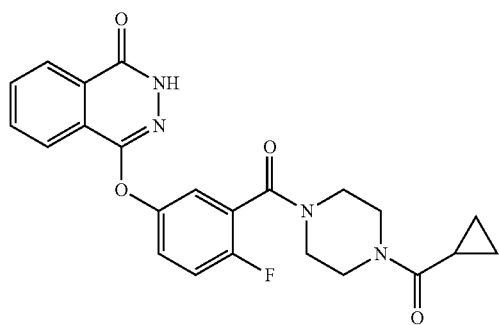 [SMILES: O=C(c1cc(Oc2n[nH]c(=O)c3ccccc23)ccc1F)N1CCN(C(=O)C2CC2)CC1]<br>4-(3-(4-(cyclopropanecarbonyl)piperazine-1-carbonyl)-4-fluorophenoxy)-2H-phthalazin-1-one |
| 51 | 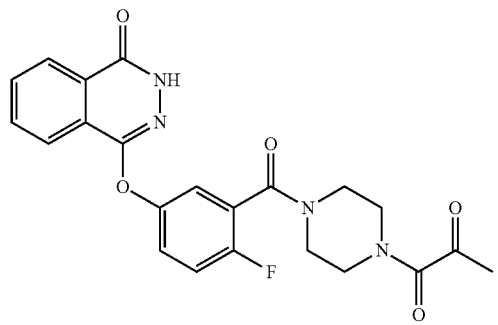 [SMILES: CC(=O)C(=O)N1CCN(C(=O)c2cc(Oc3n[nH]c(=O)c4ccccc34)ccc2F)CC1]<br>1-(4-(2-fluoro-5-(4-oxo-3-1,4-dihydronaphthyridin-1-yl-oxyl)benzoyl)piperazine-1-yl)propane-1,2-phthalazinedione |
| 52 | 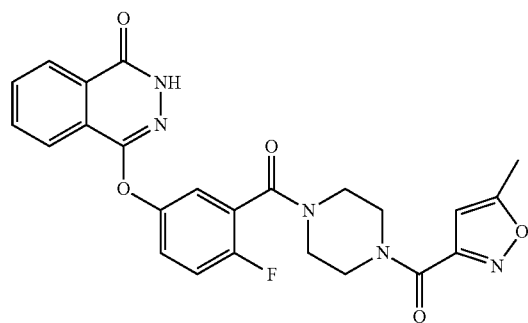 [SMILES: Cc1cc(C(=O)N2CCN(C(=O)c3cc(Oc4n[nH]c(=O)c5ccccc45)ccc3F)CC2)no1]<br>4-(4-fluoro-3-(4-(5-methylisoxazole-3-carbonyl)piperazine-1-carbonyl)phenoxy)-2H-phthalazin-1-one |

| Compound No. | Structure and Nomenclature |
|---|---|
| 53 | 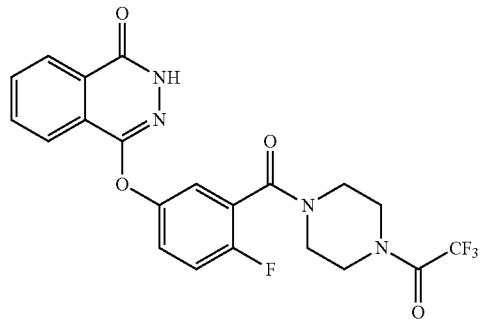 [SMILES: O=C(c1cc(Oc2n[nH]c(=O)c3ccccc23)ccc1F)N1CCN(C(=O)C(F)(F)F)CC1]<br>4-(4-fluoro-3-(4-(2,2,2-trifluoroacetyl)piperazine-1-carbonyl)phenoxy)-2H-phthalazin-1-one |
| 54 | 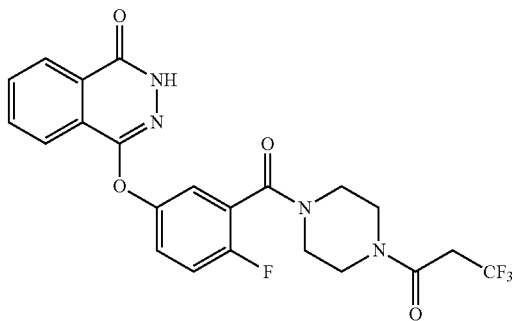 [SMILES: O=C(CC(F)(F)F)N1CCN(C(=O)c2cc(Oc3n[nH]c(=O)c4ccccc34)ccc2F)CC1]<br>4-(4-fluoro-3-(4-(3,3,3-trifluoropropionyl)piperazine-1-carbonyl)phenoxy)-2H-phthalazin-1-one |
| 55 | 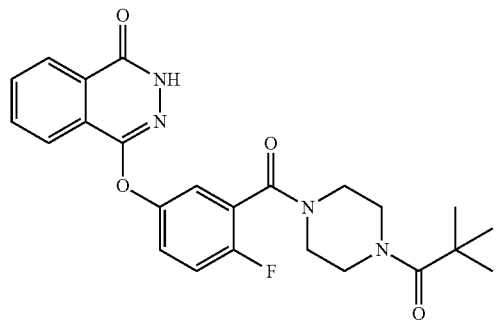 [SMILES: CC(C)(C)C(=O)N1CCN(C(=O)c2cc(Oc3n[nH]c(=O)c4ccccc34)ccc2F)CC1]<br>4-(4-fluoro-3-(4-pivaloylpiperazine-1-carbonyl)phenoxy)-2H-phthalazin-1-one |
| 56 | 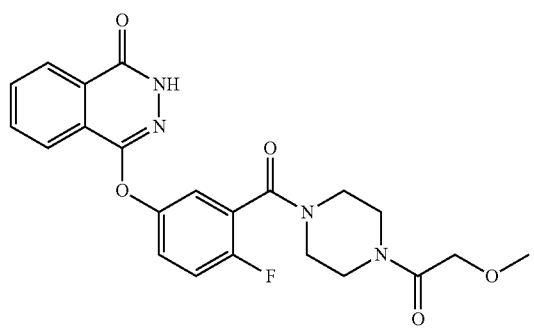 [SMILES: COCC(=O)N1CCN(C(=O)c2cc(Oc3n[nH]c(=O)c4ccccc34)ccc2F)CC1]<br>4-(4-fluoro-3-(4-(2-methoxyacetyl)piperazine-1-carbonyl)phenoxy-2H-phthalazin-1-one |

| Compound No. | Structure and Nomenclature |
|---|---|
| 57 | 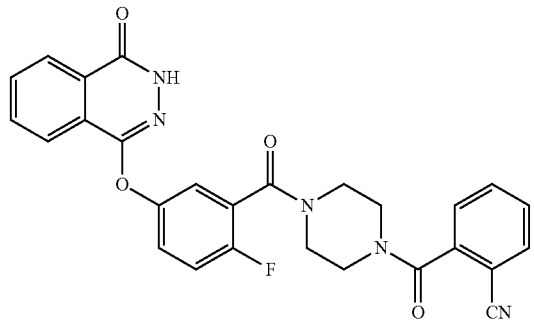 [SMILES: N#Cc1ccccc1C(=O)N1CCN(C(=O)c2cc(Oc3n[nH]c(=O)c4ccccc34)ccc2F)CC1]<br>4-(4-fluoro-3-(4-(2-cyanobenzoyl)piperazine-1-carbonyl)phenoxy)-2H-phthalazin-1-one |
| 58 | 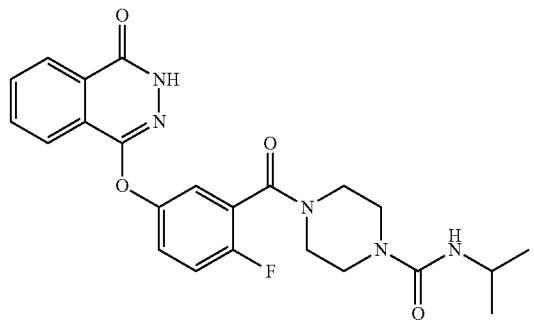 [SMILES: CC(C)NC(=O)N1CCN(C(=O)c2cc(Oc3n[nH]c(=O)c4ccccc34)ccc2F)CC1]<br>4-(2-fluoro-5-(4-oxo-3,4-2H-phthalazin-1-yl-oxyl)benzoyl)-N-isopropyl-1-formamide |
| 59 | 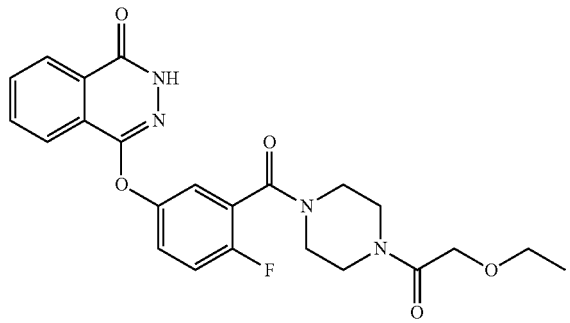 [SMILES: CCOCC(=O)N1CCN(C(=O)c2cc(Oc3n[nH]c(=O)c4ccccc34)ccc2F)CC1]<br>4-(3-(4-(2-ethoxyacetyl)piperazine-1-carbonyl)-4-fluorophenoxy)-2H-phthalazin-1-one |
| 60 | 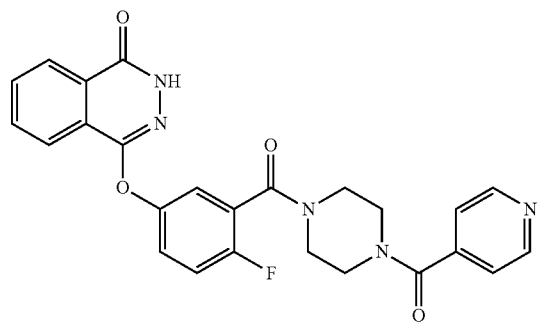 [SMILES: O=C(c1ccncc1)N1CCN(C(=O)c2cc(Oc3n[nH]c(=O)c4ccccc34)ccc2F)CC1]<br>4-(4-fluoro-3-(4-isonicotinoylpiperazine-1-carbonyl)phenoxy)-2H-phthalazin-1-one |

| Compound No. | Structure and Nomenclature |
|---|---|
| 61 | 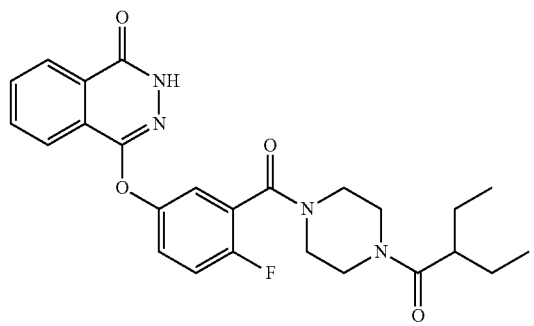 [SMILES: CCC(CC)C(=O)N1CCN(C(=O)c2cc(Oc3n[nH]c(=O)c4ccccc34)ccc2F)CC1]<br>4-(3-(4-(2-ethylbutyryl)piperazine-1-carbonyl)-4-fluorophenoxy)-2H-phthalazin-1-one |
| 62 | 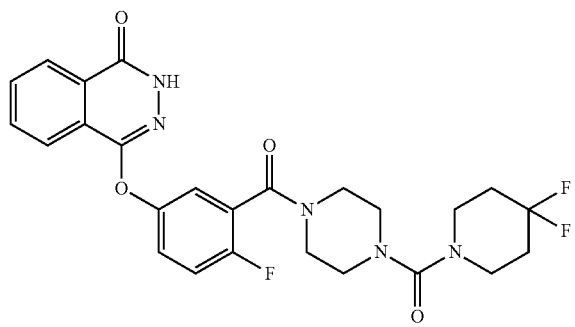 [SMILES: O=C(c1cc(Oc2n[nH]c(=O)c3ccccc23)ccc1F)N1CCN(C(=O)N2CCC(F)(F)CC2)CC1]<br>4-(4-fluoro-3-(4-(4,4-difluoropiperidine-1-carbonyl)piperazine-1-carbonyl)phenoxy)-2H-phthalazin-1-one |
| 63 | 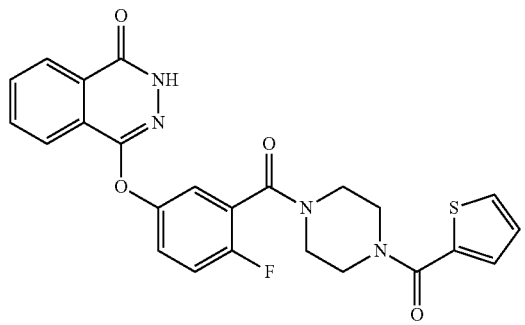 [SMILES: O=C(c1cccs1)N1CCN(C(=O)c2cc(Oc3n[nH]c(=O)c4ccccc34)ccc2F)CC1]<br>4-(4-fluoro-3-(4-(thiophene-2-carbonyl)piperazine-1-carbonyl)phenoxy)-2H-phthalazin-1-one |
| 64 | 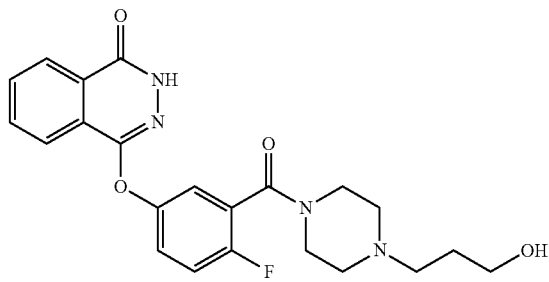 [SMILES: O=C(c1cc(Oc2n[nH]c(=O)c3ccccc23)ccc1F)N1CCN(CCCO)CC1]<br>4-(4-fluoro-3-(4-(3-hydroxypropyl)piperazine-1-carbonyl)phenoxy)-2H-phthalazin-1-one |

| Compound No. | Structure and Nomenclature |
|---|---|
| 65 | 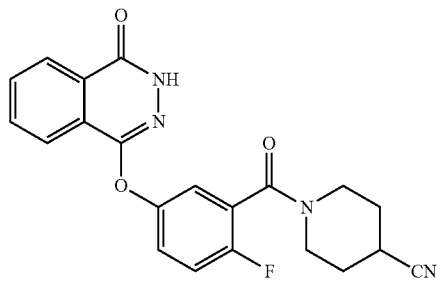 [SMILES: N#CC1CCN(C(=O)c2cc(Oc3n[nH]c(=O)c4ccccc34)ccc2F)CC1]
1-(2-fluoro-5-(4-oxo-3,4-2H-phthalazine-1-yl-oxyl)benzoyl)piperidine-4-formonitrile |
| 66 | 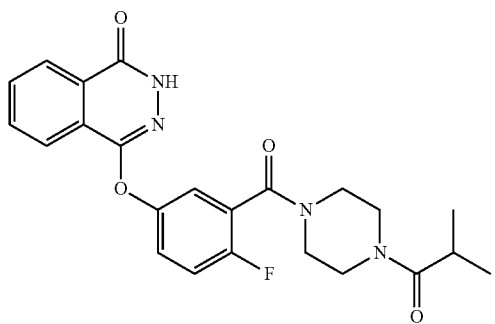 [SMILES: CC(C)C(=O)N1CCN(C(=O)c2cc(Oc3n[nH]c(=O)c4ccccc34)ccc2F)CC1]
4-(4-fluoro-3-(4-isobutyrylpiperazine-1-carbonyl)phenoxy)-2H-phthalazin-1-one |
| 67 | 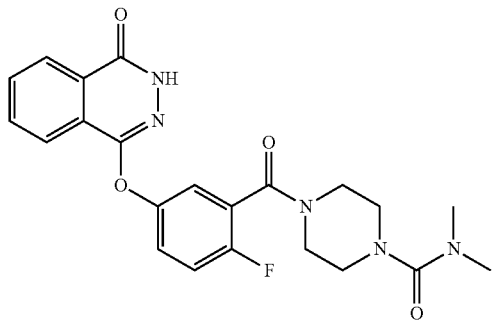 [SMILES: CN(C)C(=O)N1CCN(C(=O)c2cc(Oc3n[nH]c(=O)c4ccccc34)ccc2F)CC1]
4-(2-fluoro-5-(4-oxo-3,4-2H-phthalazin-1-yl-oxyl)benzoyl)-N,N-dimethylpiperazine-1-formamide |
| 68 | 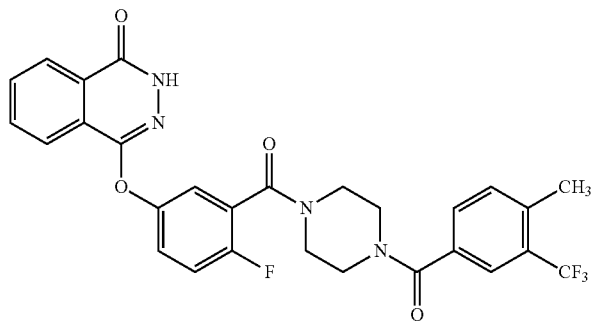 [SMILES: Cc1ccc(C(=O)N2CCN(C(=O)c3cc(Oc4n[nH]c(=O)c5ccccc45)ccc3F)CC2)cc1C(F)(F)F]
4-(4-fluoro-3-(4-(3-trifluoromethyl-4-methyl-benzoyl)piperazine-1-carbonyl)phenoxy)-2H-phthalazin-1-one |

| Compound No. | Structure and Nomenclature |
|---|---|
| 69 | 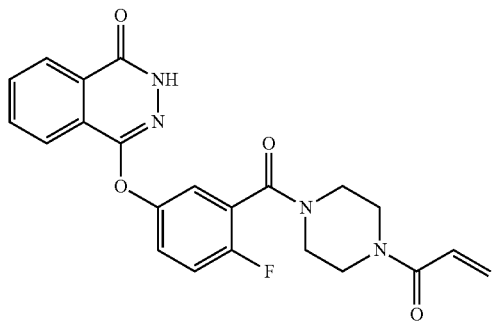 [SMILES: C=CC(=O)N1CCN(C(=O)c2cc(Oc3n[nH]c(=O)c4ccccc34)ccc2F)CC1]
4-(3-(4-acryloylpiperazine-1-carbonyl)-4-fluorophenoxy)-2H-phthalazin-1-one |
| 70 | 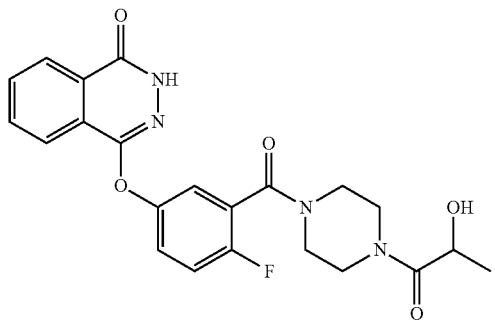 [SMILES: CC(O)C(=O)N1CCN(C(=O)c2cc(Oc3n[nH]c(=O)c4ccccc34)ccc2F)CC1]
4-(4-fluoro-3-(4-(2-hydroxypropionyl)piperazine-1-carbonyl)phenoxy)-2H-phthalazin-1-one |
| 71 | 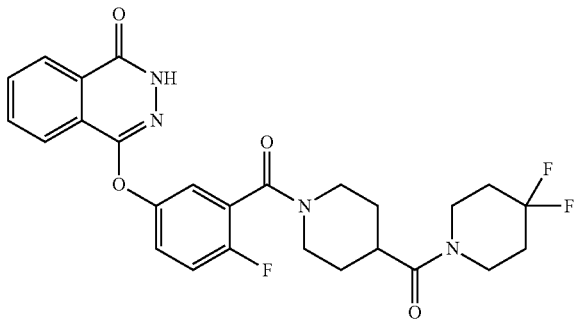 [SMILES: O=C(c1cc(Oc2n[nH]c(=O)c3ccccc23)ccc1F)N1CCC(C(=O)N2CCC(F)(F)CC2)CC1]
4-(3-(4-(4,4-difluoropiperidine-1-carbonyl)piperidine-1-carbonyl)-4-fluorophenoxy)-2H-phthalazin-1-one |
| 72 | 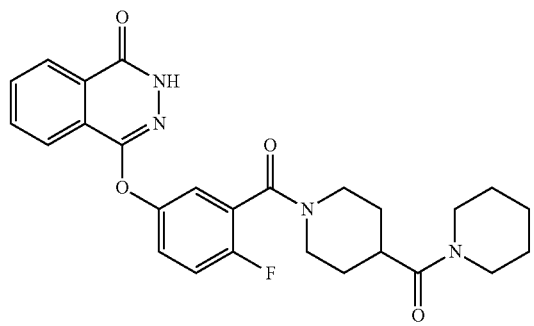 [SMILES: O=C(c1cc(Oc2n[nH]c(=O)c3ccccc23)ccc1F)N1CCC(C(=O)N2CCCCC2)CC1]
4-(4-fluoro-3-(4-(piperidine-1-carbonyl)piperidine-1-carbonyl)phenoxy)-2H-phthalazin-1-one |

| Compound No. | Structure and Nomenclature |
|---|---|
| 73 | 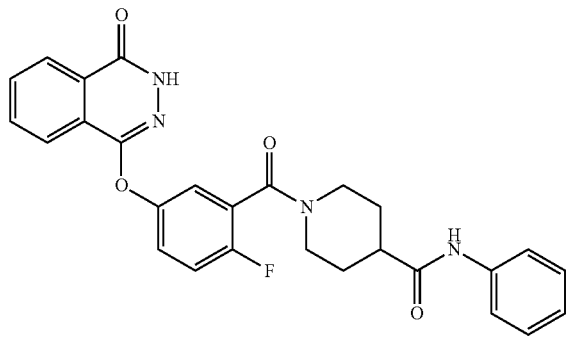 [SMILES: O=C(Nc1ccccc1)C1CCN(C(=O)c2cc(Oc3n[nH]c(=O)c4ccccc34)ccc2F)CC1]<br>1-(2-fluoro-5-(4-oxo-3,4-2H-phthalazin-1-yl-oxyl)benzoyl)-N-phenylpiperidine-4-formamide |
| 74 | 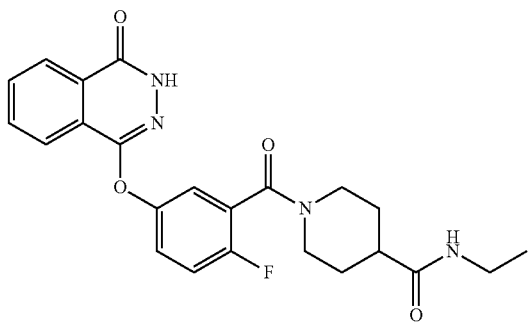 [SMILES: CCNC(=O)C1CCN(C(=O)c2cc(Oc3n[nH]c(=O)c4ccccc34)ccc2F)CC1]<br>N-ethyl-1-(2-fluoro-5-(4-oxo-1,4-dihydro-phthalazin-1-yl-oxyl)benzoyl)piperidine-4-formamide |
| 75 | 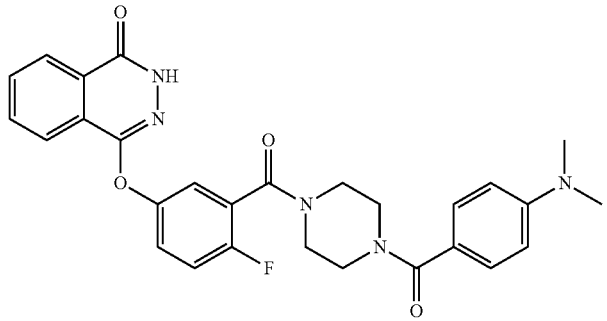 [SMILES: CN(C)c1ccc(C(=O)N2CCN(C(=O)c3cc(Oc4n[nH]c(=O)c5ccccc45)ccc3F)CC2)cc1]<br>4-(3-(4-(4-(dimethylamino)benzoyl)piperazine-1-carbonyl)-4-fluorophenoxy)-2H-phthalazin-1-one |
| 76 | 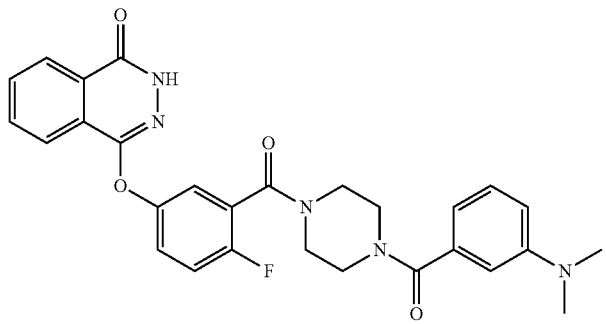 [SMILES: CN(C)c1cccc(C(=O)N2CCN(C(=O)c3cc(Oc4n[nH]c(=O)c5ccccc45)ccc3F)CC2)c1]<br>4-(3-(4-(3-(dimethylamino)benzoyl)piperazine-1-carbonyl)-4-fluorophenoxy)-2H-phthalazin-1-one |

| Compound No. | Structure and Nomenclature |
|---|---|
| 77 | 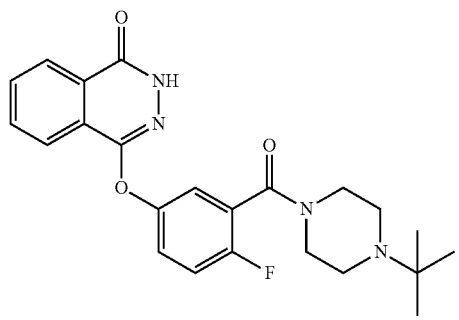 [SMILES: CC(C)(C)N1CCN(C(=O)c2cc(Oc3n[nH]c(=O)c4ccccc34)ccc2F)CC1]<br>4-(3-(4-tertbutylpiperazine-1-carbonyl)-4-fluorophenoxy)-2H-phthalazin-1-one |
| 78 | 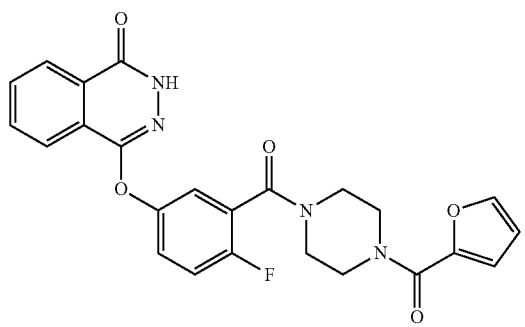 [SMILES: O=C(c1ccco1)N1CCN(C(=O)c2cc(Oc3n[nH]c(=O)c4ccccc34)ccc2F)CC1]<br>4-(4-fluoro-3-(4-(furan-2-carbonyl)piperazine-1-carbonyl)phenoxy)-2H-phthalazin-1-one |
| 79 | 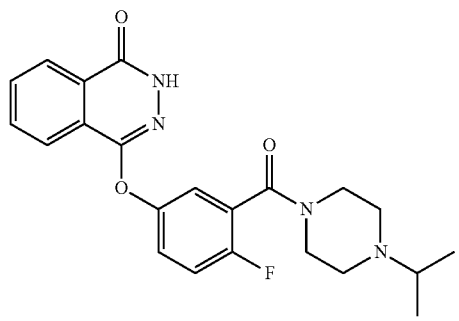 [SMILES: CC(C)N1CCN(C(=O)c2cc(Oc3n[nH]c(=O)c4ccccc34)ccc2F)CC1]<br>4-(4-fluoro-3-(4-isopropyl-1-carbonyl)phenoxy)-2H-phthalazin-1-one |
| 80 | 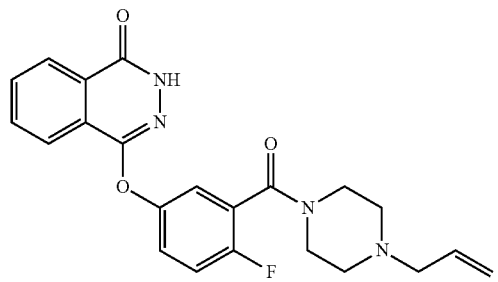 [SMILES: C=CCN1CCN(C(=O)c2cc(Oc3n[nH]c(=O)c4ccccc34)ccc2F)CC1]<br>4-(3-(4-allylpiperazine-1-carbonyl)-4-fluorophenoxy)-2H-phthalazin-1-one |

| Compound No. | Structure and Nomenclature |
|---|---|
| 81 | 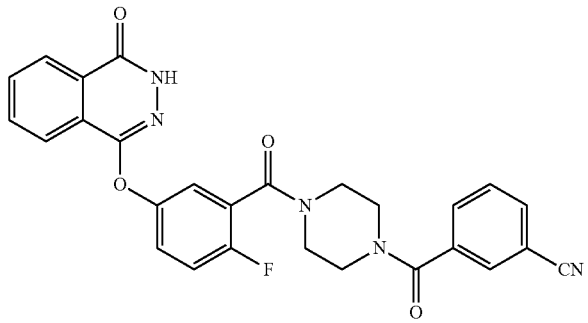 [SMILES: N#Cc1cccc(C(=O)N2CCN(C(=O)c3cc(Oc4n[nH]c(=O)c5ccccc45)ccc3F)CC2)c1]<br>4-(3-(4-3-cyanobenzoylpiperazine-1-carbonyl)-4-fluorophenoxy)-2H-phthalazin-1-one |
| 82 | 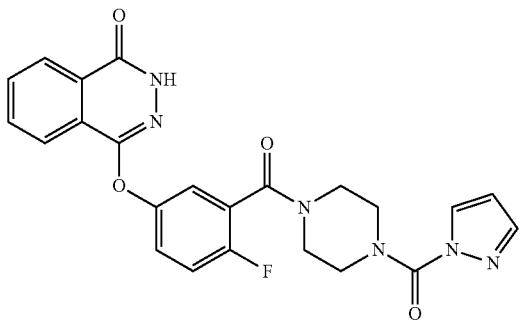 [SMILES: O=C(c1cc(Oc2n[nH]c(=O)c3ccccc23)ccc1F)N1CCN(C(=O)n2cccn2)CC1]<br>4-(3-(4-(1H-pyrazole-1-carbonyl)piperazine-1-carbonyl)-4-fluorophenoxy)-2H-phthalazin-1-one |
| 83 | 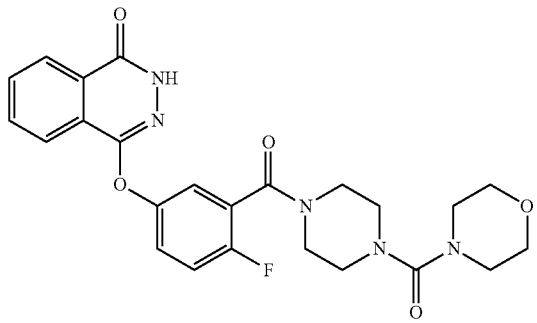 [SMILES: O=C(c1cc(Oc2n[nH]c(=O)c3ccccc23)ccc1F)N1CCN(C(=O)N2CCOCC2)CC1]<br>4-(4-fluoro-3-(4-(morpholine-4-carbonyl)piperazine-1-carbonyl)phenoxy)-2H-phthalazin-1-one |
| 84 | 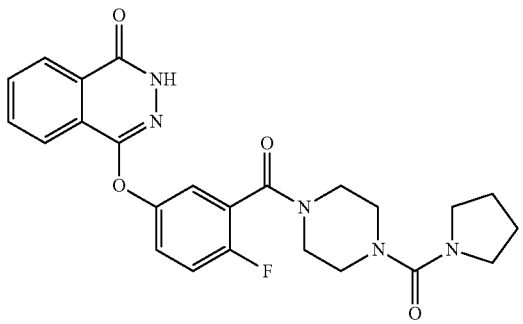 [SMILES: O=C(c1cc(Oc2n[nH]c(=O)c3ccccc23)ccc1F)N1CCN(C(=O)N2CCCC2)CC1]<br>4-(4-fluoro-3-(4-(pyrrolidine-1-carbonyl)piperazine-1-carbonyl)phenoxy)-2H-phthalazin-1-one |

| Compound No. | Structure and Nomenclature |
|---|---|
| 85 | 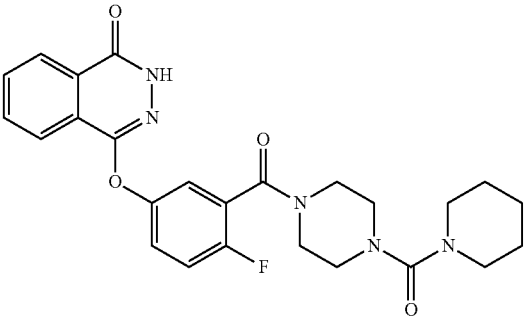 [SMILES: O=C(c1cc(Oc2n[nH]c(=O)c3ccccc23)ccc1F)N1CCN(C(=O)N2CCCCC2)CC1]<br>4-(4-fluoro-3-(4-(piperidine-1-carbonyl)piperazine-1-carbonyl)phenoxy)-2H-phthalazin-1-one |
| 86 | 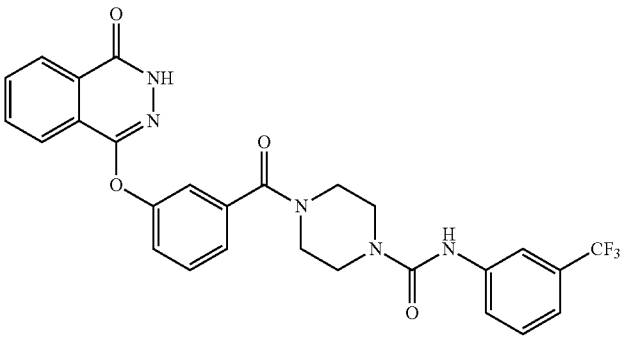 [SMILES: O=C(Nc1cccc(C(F)(F)F)c1)N1CCN(C(=O)c2cccc(Oc3n[nH]c(=O)c4ccccc34)c2)CC1]<br>4-(3-(4-oxo-3,4-dihydro-phthalazine-1-yl-oxyl)benzoyl)-N-(3-(trifluoromethyl)phenyl)piperazine-1-formamide |
| 87 | 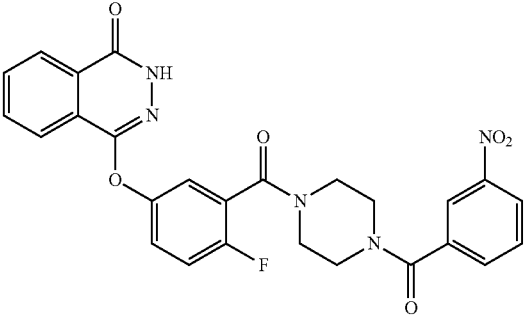 [SMILES: O=C(c1cccc([N+](=O)[O-])c1)N1CCN(C(=O)c2cc(Oc3n[nH]c(=O)c4ccccc34)ccc2F)CC1]<br>4-(4-fluoro-3-(4-(3-nitrobenzoyl)piperazine-1-carbonyl)phenoxy)-2H-phthalazin-1-one |
| 88 | 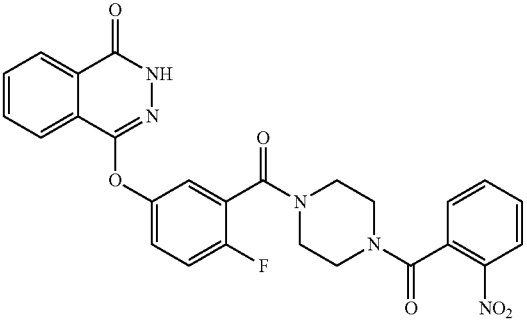 [SMILES: O=C(c1cc(Oc2n[nH]c(=O)c3ccccc23)ccc1F)N1CCN(C(=O)c2ccccc2[N+](=O)[O-])CC1]<br>4-(4-fluoro-3-(4-(2-nitrobenzoyl)piperazine-1-carbonyl)phenoxy)-2H-phthalazin-1-one |

| Compound No. | Structure and Nomenclature |
|---|---|
| 89 | 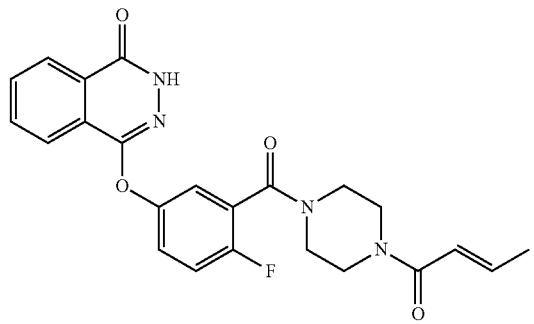 [SMILES: C/C=C/C(=O)N1CCN(C(=O)c2cc(Oc3n[nH]c(=O)c4ccccc34)ccc2F)CC1]<br>(E)-4-(3-(4-but-2-enoylpiperazine-1-carbonyl)-4-fluorophenoxy-)2H-phthalazin-1-one |
| 90 | 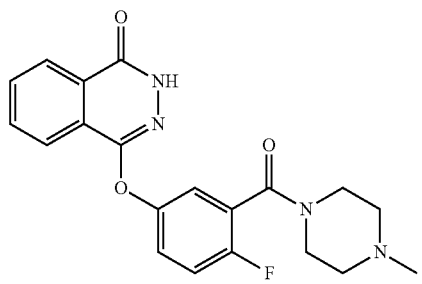 [SMILES: CN1CCN(C(=O)c2cc(Oc3n[nH]c(=O)c4ccccc34)ccc2F)CC1]<br>4-(4-fluoro-3-(4-methylpiperazine-1-carbonyl)phenoxy)-2H-phthalazin-1-one |
| 91 | 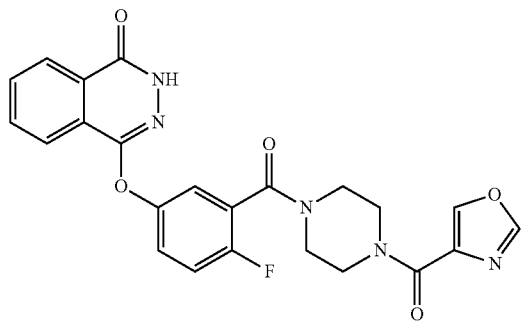 [SMILES: O=C(c1cocn1)N1CCN(C(=O)c2cc(Oc3n[nH]c(=O)c4ccccc34)ccc2F)CC1]<br>4-(4-fluoro-3-(4-(oxazole-4-carbonyl)piperazine-1-carbonyl)phenoxy)2H-phthalazin-1-one |
| 92 | 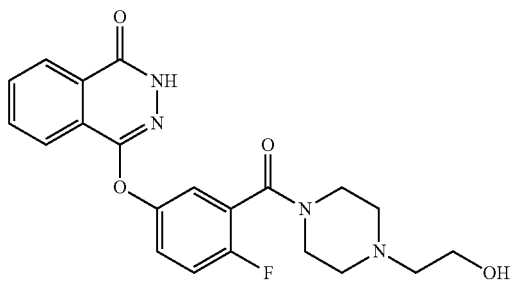 [SMILES: O=C(c1cc(Oc2n[nH]c(=O)c3ccccc23)ccc1F)N1CCN(CCO)CC1]<br>4-(4-fluoro-3-(4-(2-hydroxyethyl)piperazine-1-carbonyl)phenoxy)2H-phthalazin-1-one |

| Compound No. | Structure and Nomenclature |
|---|---|
| 93 | 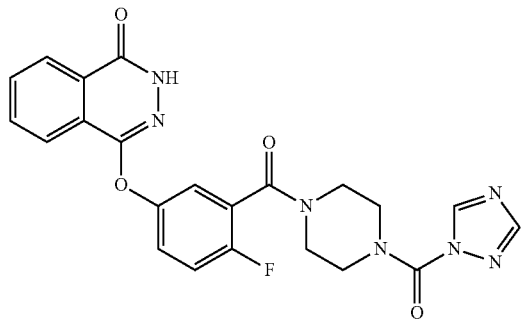 [SMILES: O=C(c1cc(Oc2n[nH]c(=O)c3ccccc23)ccc1F)N1CCN(C(=O)n2cncn2)CC1]<br>4-(3-(4-(1H-1,2,4-triazole-1-carbonyl)piperazine-1-carbonyl)-4-fluorophenoxy)2H-phthalazin-1-one |
| 94 | 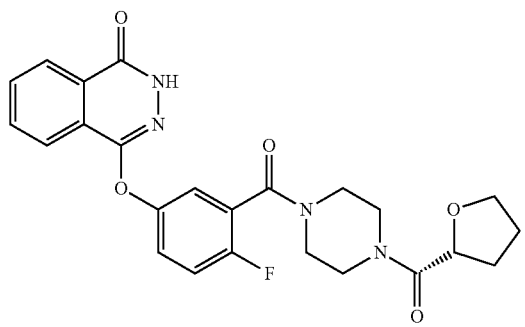<br>(R)-4-(4-fluoro-3-(4-(tetrahydrofuran-2-carbonyl)piperazine-1-carbonyl)phenoxy)2H-phthalazin-1-one |
| 95 | 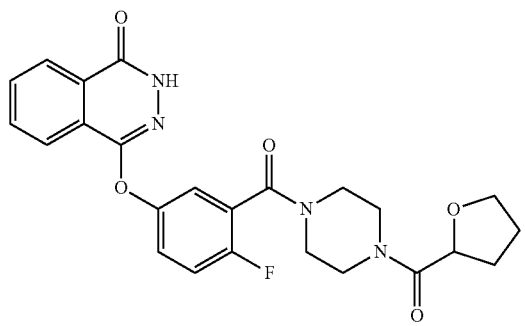 [SMILES: O=C(c1cc(Oc2n[nH]c(=O)c3ccccc23)ccc1F)N1CCN(C(=O)C2CCCO2)CC1]<br>4-(4-fluoro-3-(4-(tetrahydrofuran-2-carbonyl)piperazine-1-carbonyl)phenoxy)2H-phthalazin-1-one |
| 96 | 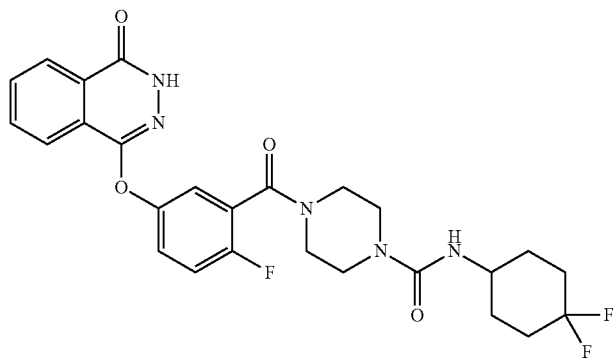 [SMILES: O=C(NC1CCC(F)(F)CC1)N1CCN(C(=O)c2cc(Oc3n[nH]c(=O)c4ccccc34)ccc2F)CC1]<br>N-(4,4-difluorocyclohexyl)-4-(2-fluoro-5-(4-oxo-3,4-dihydro-phthalazin-1-yl-oxyl)benzoyl)piperazine-1-formamide |

| Compound No. | Structure and Nomenclature |
|---|---|
| 97 | 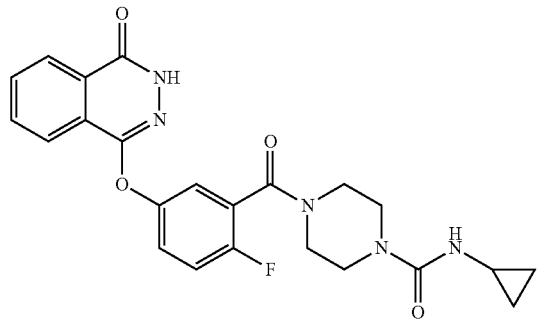 [SMILES: O=C(NC1CC1)N1CCN(C(=O)c2cc(Oc3n[nH]c(=O)c4ccccc34)ccc2F)CC1]<br>N-cyclopropyl-4-(2-fluoro-5-(4-oxo-3,4-dihydro-phthalazine-1-yl-oxyl)benzoyl)piperazine-1-formamide |
| 98 | 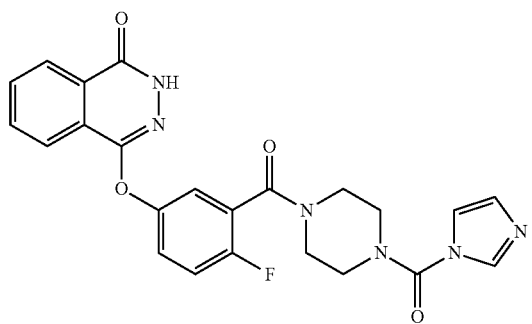 [SMILES: O=C(c1cc(Oc2n[nH]c(=O)c3ccccc23)ccc1F)N1CCN(C(=O)n2ccnc2)CC1]<br>4-(3-(4-(1H-imidazole-1-carbonyl)piperazirie-1-carbonyl)-4-fluorophenoxy)2H-phthalazin-1-one |
| 99 | 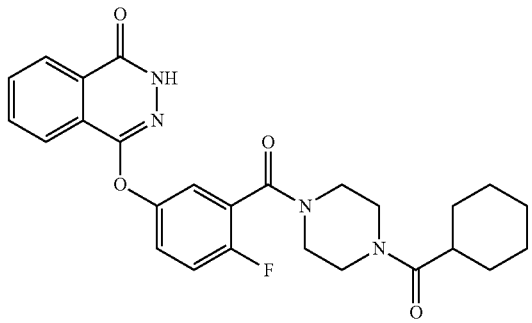 [SMILES: O=C(c1cc(Oc2n[nH]c(=O)c3ccccc23)ccc1F)N1CCN(C(=O)C2CCCCC2)CC1]<br>4-(3-(4-(cyclohexanecarbonyl)piperazine-1-carbonyl-4-fluorophenoxy)2H-phthalazin-1-one |
| 100 | 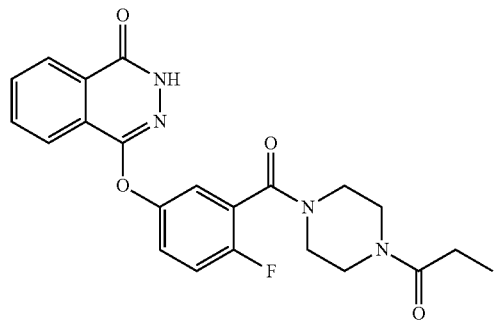 [SMILES: CCC(=O)N1CCN(C(=O)c2cc(Oc3n[nH]c(=O)c4ccccc34)ccc2F)CC1]<br>4-(4-fluoro-3-(4-propionylpiperazine-1-carbonyl)phenoxy)2H-phthalazin-1-one |

| Compound No. | Structure and Nomenclature |
|---|---|
| 101 | 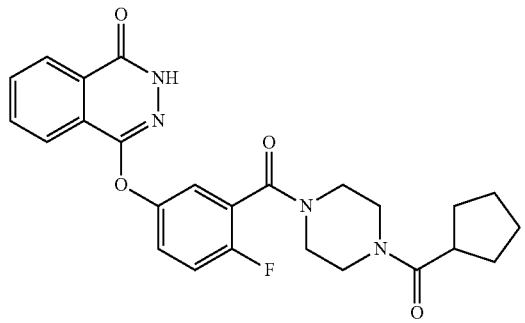 [SMILES: O=C(c1cc(Oc2n[nH]c(=O)c3ccccc23)ccc1F)N1CCN(C(=O)C2CCCC2)CC1]<br>4-(3-(4-(cyclopentylcarbonyl)piperazine-1-carbonyl)-4-fluorophenoxy)2H-phthalazin-1-one |
| 102 | 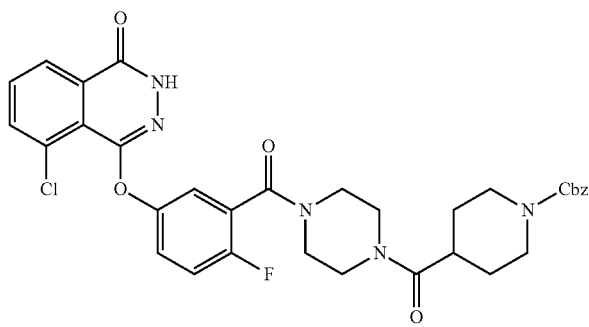 [SMILES: O=C(OCc1ccccc1)N1CCC(C(=O)N2CCN(C(=O)c3cc(Oc4n[nH]c(=O)c5cccc(Cl)c45)ccc3F)CC2)CC1]<br>8-chloro-4-(2-fluoro-(4-(4-benzyloxycarbonyl-piperidine)carbonylpiperazine-1-carbonyl)phenoxy-2H-phthalazin-1-one |
| 103 | 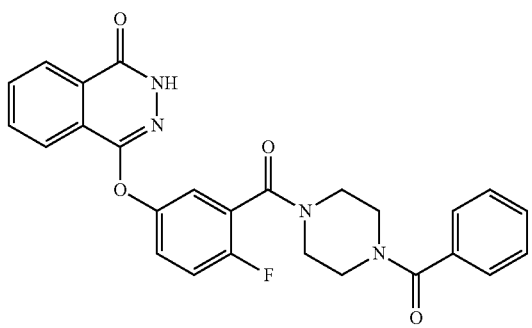 [SMILES: O=C(c1ccccc1)N1CCN(C(=O)c2cc(Oc3n[nH]c(=O)c4ccccc34)ccc2F)CC1]<br>4-(3-(4-benzoylpiperazine-1-carbonyl)-4-fluorophenoxy)2H-phthalazin-1-one |
| 104 | 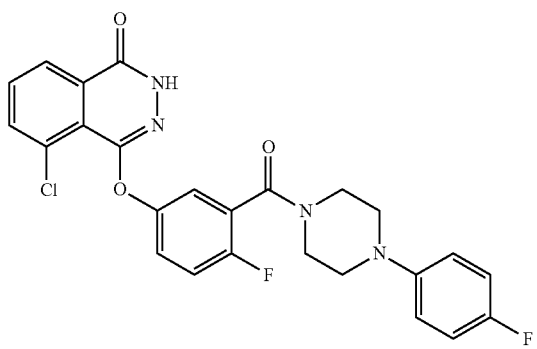 [SMILES: O=C(c1cc(Oc2n[nH]c(=O)c3cccc(Cl)c23)ccc1F)N1CCN(c2ccc(F)cc2)CC1]<br>5-chloro-4-(4-fluoro-3-(4-(4-fluorophenyl)piperazine-1-carbonyl)phenoxy)2H-phthalazin-1-one |

| Compound No. | Structure and Nomenclature |
|---|---|
| 105 | 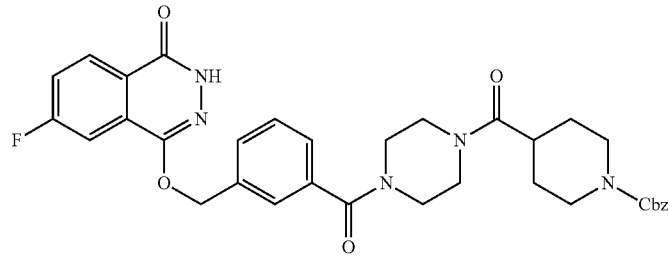 [SMILES: O=C(OCc1ccccc1)N1CCC(C(=O)N2CCN(C(=O)c3cccc(COc4n[nH]c(=O)c5ccc(F)cc45)c3)CC2)CC1]
1-benzyloxycarbonyl-4-(4-(3-((7-fluoro-4-oxo-3-1,4-dihydro-phthalazine-1-yl-oxyl)methyl)benzoyl) piperazine-1-carbonyl)piperidine |
| 106 | 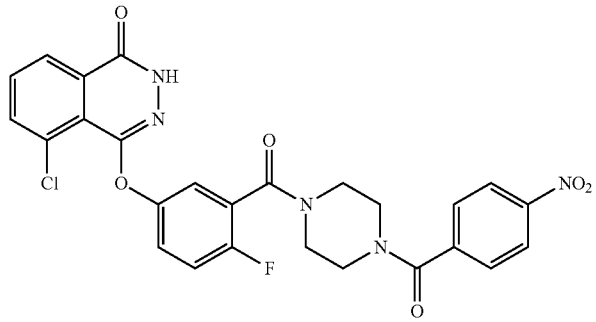 [SMILES: O=C(c1ccc([N+](=O)[O-])cc1)N1CCN(C(=O)c2cc(Oc3n[nH]c(=O)c4cccc(Cl)c34)ccc2F)CC1]
5-chloro-4-(4-fluoro-3-(4-(4-nitrobenzoyl)piperazine-1-carbonyl)phenoxy)2H-phthalazin-1-one |
| 107 | 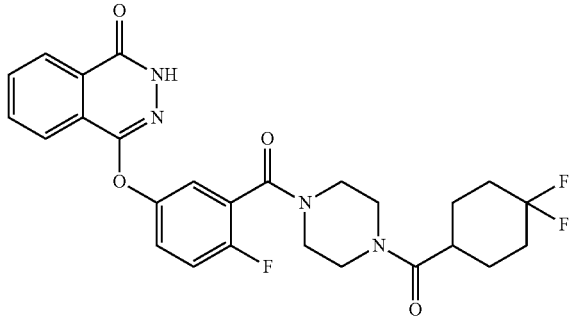 [SMILES: O=C(c1cc(Oc2n[nH]c(=O)c3ccccc23)ccc1F)N1CCN(C(=O)C2CCC(F)(F)CC2)CC1]
4-(3-(4-(4,4-difluorocyclohexanecarbonyl)piperazine-1-carbonyl)-4-fluorophenoxy)2H-phthalazin-1-one |
| 108 | 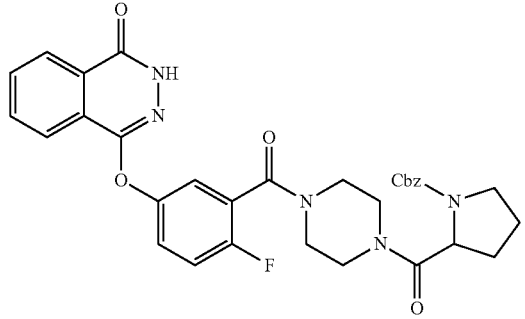 [SMILES: O=C(c1cc(Oc2n[nH]c(=O)c3ccccc23)ccc1F)N1CCN(C(=O)C2CCCN2C(=O)OCc2ccccc2)CC1]
1-benzyloxycarbonyl-2-(4-(2-fluoro-5-(4-oxo-3,4-dihydronaphthyridin-1-yl-oxyl)benzoyl)piperazine-1-carbonyl)pyrrolidine |

| Compound No. | Structure and Nomenclature |
|---|---|
| 109 | 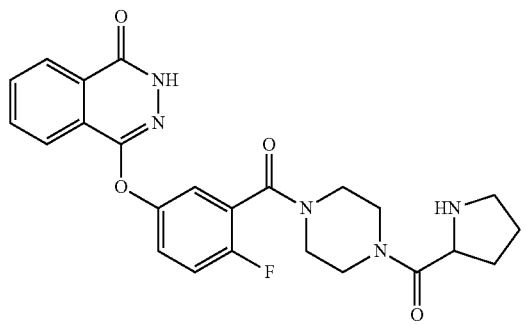 [SMILES: O=C(c1cc(Oc2n[nH]c(=O)c3ccccc23)ccc1F)N1CCN(C(=O)C2CCCN2)CC1]<br>4-(4-fluoro-3-(4-(pyrrolidine-2-carbonyl)piperazine-1-carbonyl)phenoxy)2H-phthalazin-1-one |
| 110 | 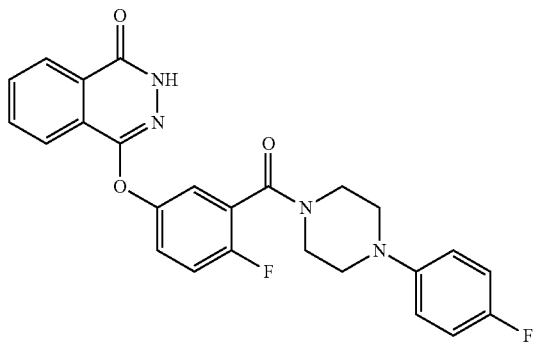 [SMILES: O=C(c1cc(Oc2n[nH]c(=O)c3ccccc23)ccc1F)N1CCN(c2ccc(F)cc2)CC1]<br>4-(4-fluoro-3-(4-(4-fluorophenyl)piperazine-1-carbonyl)phenoxy)2H-phthalazin-1-one |
| 111 | 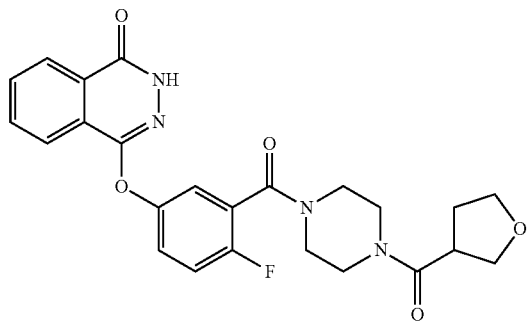 [SMILES: O=C(c1cc(Oc2n[nH]c(=O)c3ccccc23)ccc1F)N1CCN(C(=O)C2CCOC2)CC1]<br>4-(4-fluoro-3-(4-(tetrahydrofuran-3-carbonyl)piperazine-1-carbonyl)phenoxy)2H-phthalazin-1-one |
| 112 | 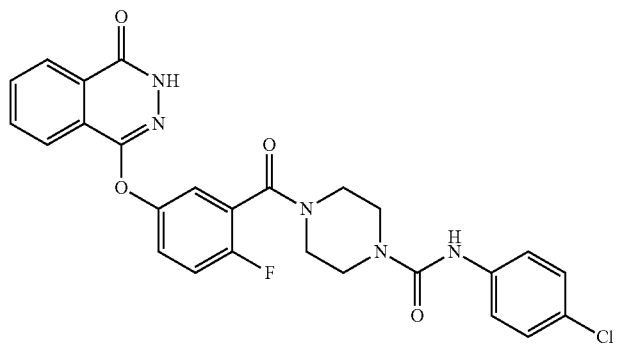 [SMILES: O=C(Nc1ccc(Cl)cc1)N1CCN(C(=O)c2cc(Oc3n[nH]c(=O)c4ccccc34)ccc2F)CC1]<br>N-(4-chlorophenyl)-4-(2-fluoro-5-(4-oxo-3,4-dihydronaphthyridin-1-yl-oxyl)benzoyl)piperazine-1-formamide |

| Compound No. | Structure and Nomenclature |
|---|---|
| 113 | 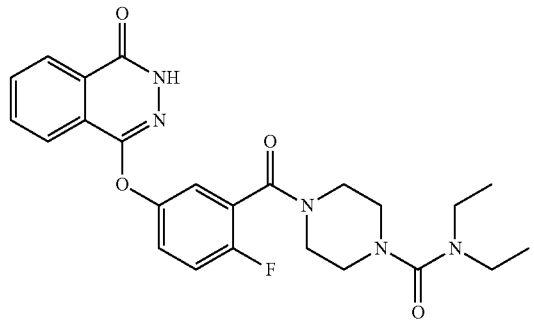 [SMILES: CCN(CC)C(=O)N1CCN(C(=O)c2cc(Oc3n[nH]c(=O)c4ccccc34)ccc2F)CC1]
N,N-diethyl-4-(2-fluoro-5-(4-oxo-3,4-dihydro-phthalazine-1-yl-oxyl)benzoyl)piperazine-1-formamide |
| 114 | 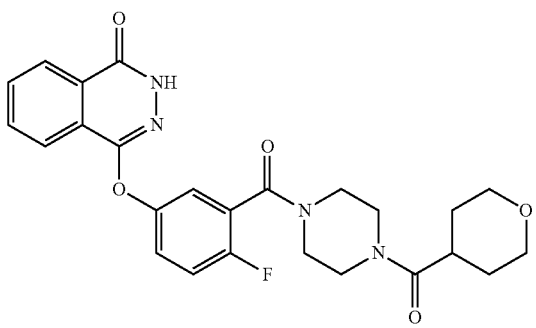 [SMILES: O=C(c1cc(Oc2n[nH]c(=O)c3ccccc23)ccc1F)N1CCN(C(=O)C2CCOCC2)CC1]
4-(4-fluoro-3-(4-(tetrahydropyran-4-carbonyl)piperazine-1-carbonyl)phenoxy)2H-phthalazin-1-one |
| 115 | 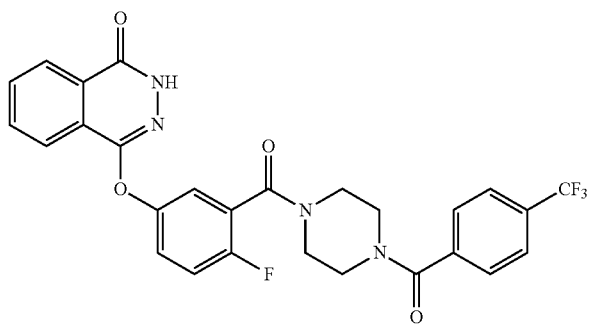 [SMILES: O=C(c1ccc(C(F)(F)F)cc1)N1CCN(C(=O)c2cc(Oc3n[nH]c(=O)c4ccccc34)ccc2F)CC1]
4-(4-fluoro-3-(4-(4-(trifluoromethyl)benzoyl)piperazine-1-carbonyl)phenoxy)2H-phthalazin-1-one |
| 116 | 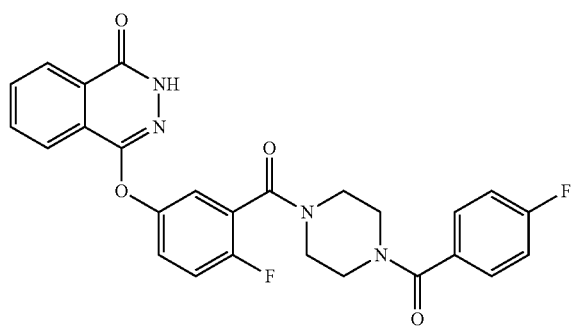 [SMILES: O=C(c1ccc(F)cc1)N1CCN(C(=O)c2cc(Oc3n[nH]c(=O)c4ccccc34)ccc2F)CC1]
4-(4-fluoro-3-(4-(4-fluorobenzoyl)piperazine-1-carbonyl)phenoxy)2H-phthalazin-1-one |

| Compound No. | Structure and Nomenclature |
|---|---|
| 117 | 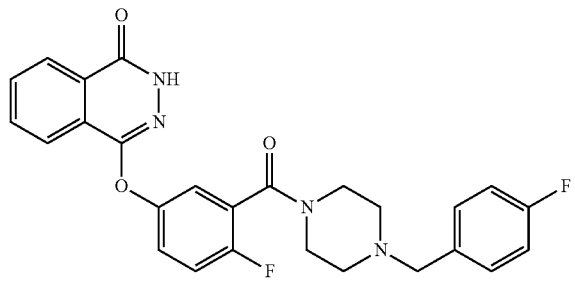 [SMILES: O=C(c1cc(Oc2n[nH]c(=O)c3ccccc23)ccc1F)N1CCN(Cc2ccc(F)cc2)CC1]<br>4-(4-fluoro-3-(4-(4-fluorobenzyl)piperazine-1-carbonyl)phenoxy)-2H-phthalazin-1-one |
| 118 | 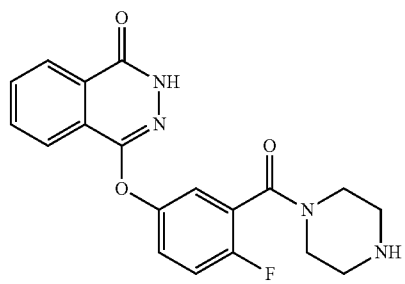 [SMILES: O=C(c1cc(Oc2n[nH]c(=O)c3ccccc23)ccc1F)N1CCNCC1]<br>4-(4-fluoro-3-(piperazine-1-carbonyl)phenoxy)2H-phthalazin-1-one |
| 119 | 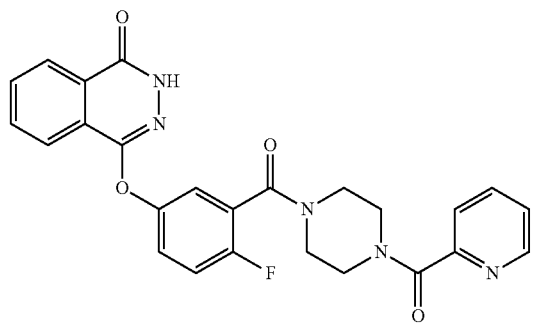 [SMILES: O=C(c1ccccn1)N1CCN(C(=O)c2cc(Oc3n[nH]c(=O)c4ccccc34)ccc2F)CC1]<br>4-(4-fluoro-3-(4-pyridineformylpiperazine-1-carbonyl)phenoxy)2H-phthalazin-1-one |
| 120 | 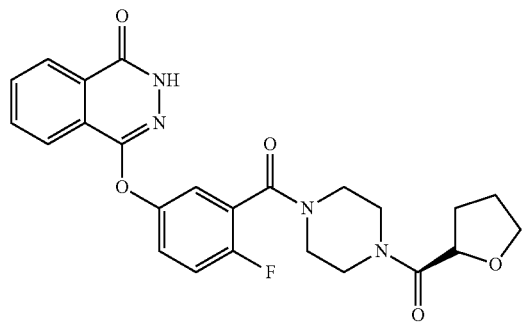<br>(S)-4-(4-fluoro-3-(4-(tetrahydrofuran-2-carbonyl)piperazine-1-carbonyl)phenoxy)2H-phthalazin-1-one |

| Compound No. | Structure and Nomenclature |
|---|---|
| 121 | 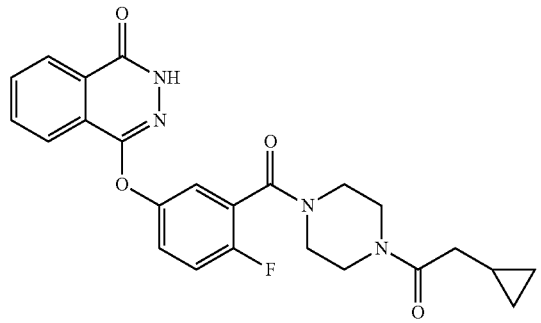 [SMILES: O=C(CC1CC1)N1CCN(C(=O)c2cc(Oc3n[nH]c(=O)c4ccccc34)ccc2F)CC1]<br>4-(3-(4-(2-cyclopropylacetyl)piperazine-1-carbonyl)-4-fluorophenoxy)2H-phthalazin-1-one |
| 122 | 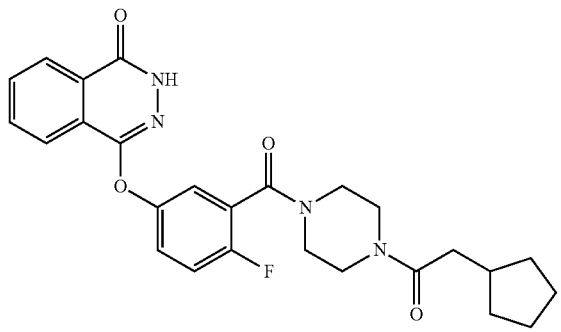 [SMILES: O=C(CC1CCCC1)N1CCN(C(=O)c2cc(Oc3n[nH]c(=O)c4ccccc34)ccc2F)CC1]<br>4-(3-(4-(2-cyclopentylacetyl)piperazine-1-carbonyl)-4-fluorophenoxy)2H-phthalazin-1-one |
| 123 | 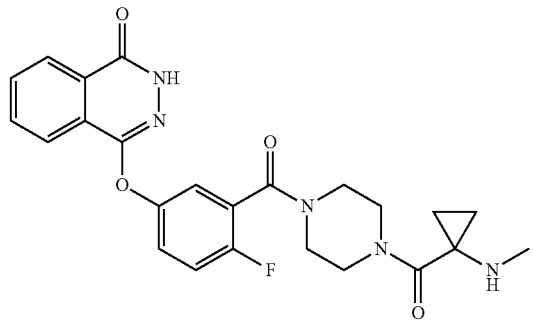 [SMILES: CNC1(C(=O)N2CCN(C(=O)c3cc(Oc4n[nH]c(=O)c5ccccc45)ccc3F)CC2)CC1]<br>4-(4-fluoro-3-(4-(1-(methylamino)cyclopropanecarbonyl)piperazine-1-carbonyl)phenoxy)2H-phthalazin-1-one |
| 124 | 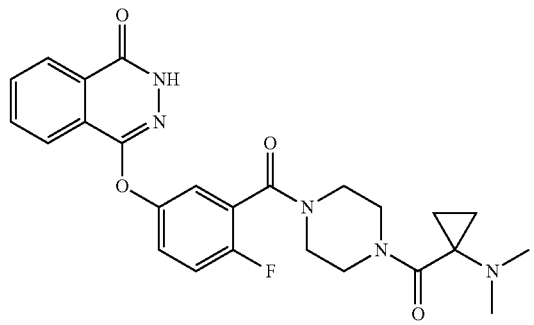 [SMILES: CN(C)C1(C(=O)N2CCN(C(=O)c3cc(Oc4n[nH]c(=O)c5ccccc45)ccc3F)CC2)CC1]<br>4-(3-(4-(1-(dimethylamino)cyclopropanecarbonyl)piperazine-1-carbonyl)-4-fluorophenoxy)2H-phthalazin-1-one |

| Compound No. | Structure and Nomenclature |
|---|---|
| 125 | 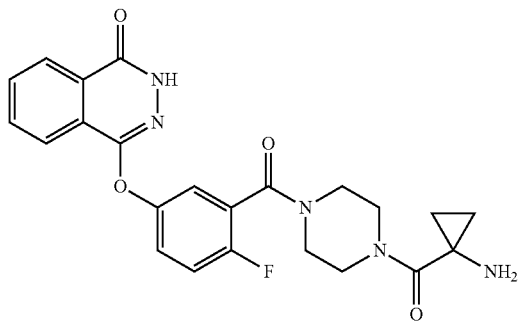 [SMILES: NC1(C(=O)N2CCN(C(=O)c3cc(Oc4n[nH]c(=O)c5ccccc45)ccc3F)CC2)CC1]<br>4-(3-(4-(1-aminocyclopropanecarbonyl)piperazine-1-carbonyl)-4-fluorophenoxy)2H-phthalazin-1-one |
| 126 | 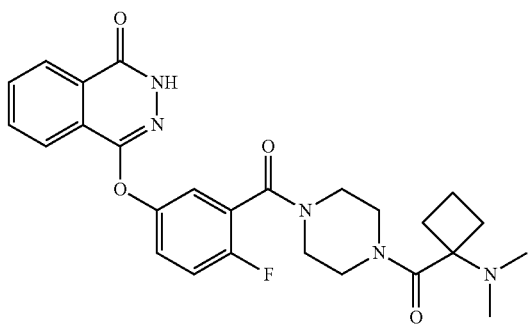 [SMILES: CN(C)C1(C(=O)N2CCN(C(=O)c3cc(Oc4n[nH]c(=O)c5ccccc45)ccc3F)CC2)CCC1]<br>4-(3-(4-(1-(dimethylamino)cyclobutanecarbonyl)piperazine-1-carbonyl)-4-fluorophenoxy)2H-phthalazin-1-one |
| 127 | 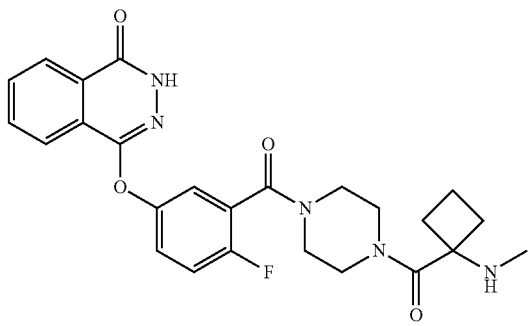 [SMILES: CNC1(C(=O)N2CCN(C(=O)c3cc(Oc4n[nH]c(=O)c5ccccc45)ccc3F)CC2)CCC1]<br>4-(4-fluoro-3-(4-(1-(methylamino)cyclobutanecarbonyl)piperazine-1-carbonyl)phenoxy)2H-phthalazin-1-one |
| 128 | 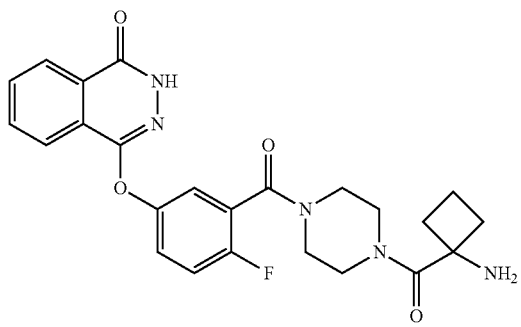 [SMILES: NC1(C(=O)N2CCN(C(=O)c3cc(Oc4n[nH]c(=O)c5ccccc45)ccc3F)CC2)CCC1]<br>4-(3-(4-(1-aminocyclobutanecarbonyl)piperazine-1-carbonyl)-4-fluorophenoxy)2H-phthalazin-1-one |

| Compound No. | Structure and Nomenclature |
| --- | --- |
| 129 | 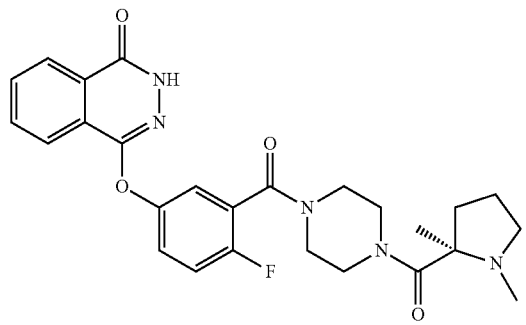 [SMILES: CN1CCC[C@]1(C)C(=O)N1CCN(C(=O)c2cc(Oc3n[nH]c(=O)c4ccccc34)ccc2F)CC1]<br>(R)-4-(3-(4-(1,2-dimethylpyrrolidine-2-carbonyl)piperazine-1-carbonyl)-4-fluorophenoxy)2H-phthalazin-1-one |
| 130 | 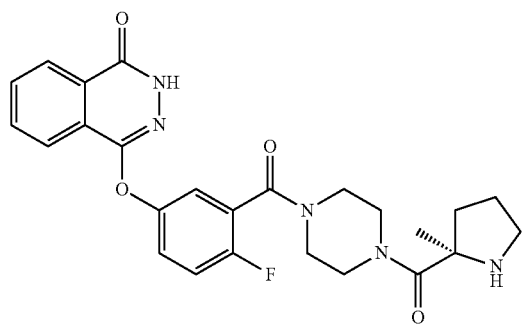 [SMILES: C[C@]1(C(=O)N2CCN(C(=O)c3cc(Oc4n[nH]c(=O)c5ccccc45)ccc3F)CC2)CCCN1]<br>(R)-4-(4-fluoro-3-(4-(2-methylpyrrolidine-2-carbonyl)piperazine-1-carbonyl)phenoxy)-2H-phthalazin-1-one |

The present invention further provides a pharmaceutical composition comprising an effective amount of the aforementioned compounds, pharmaceutically acceptable salts, hydrates, solvates or stereoisomers thereof, and pharmaceutically acceptable carriers. The pharmaceutically acceptable carriers are conventional medicinal carriers in the art and are not discussed herein.

The above-listed compounds, pharmaceutically acceptable salts, hydrates, solvates and stereoisomers and the pharmaceutical compositions thereof can be used as drugs for treating diseases mediated by PARP, including cancers, neurodegenerative diseases, cardiovascular diseases, diabetes and inflammation.

Therefore, the present invention also provides use of the compounds, pharmaceutically acceptable salts, hydrates, solvates or stereoisomers thereof in the manufacture of medicaments for treating diseases mediated by PARP. The diseases mediated by PARP are selected from cancers, neurodegenerative diseases, cardiovascular diseases, diabetes and inflammation.

In particular, the cancers are histiocytic lymphoma, non-small cell lung cancer, small-cell lung cancer, lung adenocarcinoma, lung squamous carcinoma, pancreatic cancer, breast cancer, prostate cancer, liver cancer, gastric cancer, colon cancer, colorectal cancer, ovarian cancer, cervical cancer, brain cancer, esophageal cancer, bone cancer, testicular cancer, melanoma, skin cancer, epithelial cell cancer, prostate cancer, nasopharyngeal cancer, oral cancer, leukemia, and any one of brain tumor, reproductive system tumor, lymphatic system tumor, digestive system tumor, respiratory system tumor and skin tumor.

The compounds and compositions thereof in the present invention can be used in the prevention or treatment of the onset or development of any of the PARP activity associated diseases or conditions in mammals especially in human. These symptoms comprise traumatic injuries to the central nervous system, e.g. brain damage, and neurodegenerations associated with the traumatic injuries to the central nervous system. The associated symptoms and diseases that can be treated by the methods of the present invention comprise vessel stroke, cardiac ischemia, cerebral ischemia, cerebral vascular disorders such as multiple sclerosis, and neurodegenerative diseases such as Alzheimer's disease, Huntington's disease and Parkinson's disease.

The compounds of the present invention may be used in the treatment or prevention of tissue damages caused by cell damage or death that are induced by necrosis or apoptosis, and in alleviating nervous or cardiovascular tissue damage, comprising subsequent ischemia, myocardial infarction and reperfusion injury. It may be also used in the treatment or prevention of other cardiovascular diseases, such as angina and cardiovascular ischemia.

Other PARP associated symptoms or diseases that can be treated with the compounds of the present invention comprise inflammation, e.g. pleurisy and colitis, endotoxic shock, diabetes, arthritis, cardiac ischemia, retinal ischemia, skin aging, chronic and acute pain, hemorrhagic shock, etc. For example, after a stroke symptom, the patient is treated with one or more compounds of the present invention to prevent the brain from damage or minimize the damage.

The invention also provides methods for treating the aforementioned diseases mediated by PARP, comprising steps of administrating to a patient an effective amount of the compound, pharmaceutically acceptable salt, hydrate, solvate or stereoisomer thereof of any of claims 1-10, or the pharmaceutical composition of claim 14.

The compounds of the present invention can be administrated in pure form, in a combination with other active ingredients or a combination with pharmaceutically acceptable non-toxic excipients or carriers. Oral compositions generally comprise inert diluent carriers or edible carriers. Pharmaceutically compatible adhesives and/or adjuvants may be used as a part of the compositions. Tablets, pills, capsules and troches may contain any of the following components or compounds with similar properties: adhesives such as microcrystalline cellulose, tragacanth and gelatin; excipients such as starch or lactose; dispersants such as alginic acid, Primogel or corn starch; lubricants such as magnesium stearate; flow aid such as colloidal silica; sweeteners such as sucrose and saccharin; or flavoring agents such as mint oil, methyl salicylate or orange flavor. When the unit dosage form is a capsule, in addition to the above types of substances, the compositions may further comprise liquid carriers such as fatty oil. Besides, the unit dosage form may contain other substances of various physical forms that improve the dosage unit, such as sugar-coating, shellacs or intestinal solvents. Further, in addition to the active compounds, syrup can contain sucrose as sweetener and certain preservative, dye, pigment and spice.

The selective preparations for administration comprise sterile water or non-aqueous solutions, suspensions and emulsions. Examples of non-aqueous solvents are dimethyl sulfoxide, alcohol, propylene glycol, polyethylene glycol, vegetable oils such as olive oil and injectable organic esters such as ethyl oleate. Aqueous carriers comprise a mixture of alcohol and water, buffering medium and saline. Intravenous carriers comprise fluid and nutritional supplements, electrolyte supplements, such as the carriers based on ringer dextrose. Preservatives and other additives may also exist, such as antibacterials, antioxidants, chelating agents and inert gas.

The compounds of the present invention may also be used as forms of pharmaceutically acceptable salts, hydrates, solvates or metabolites. The pharmaceutically acceptable salts comprise alkali salts of inorganic and organic acids, the acids comprise but not limit to hydrochloric acid, hydrobromic acid, sulfuric acid, phosphoric acid, methanesulfonic acid, ethylsulfonic acid, malic acid, acetic acid, oxalic acid, tartaric acid, citric acid, lactic acid, fumaric acid, succinic acid, maleic acid, salicylic acid, benzoic acid, phenylacetic acid, mandelic acid. When the compounds of the present invention comprise acidic functional groups such as carboxyl, the suitable pharmaceutically acceptable carboxylic cations are well-known for a person skilled in the art, including alkali, alkaline earth, ammonium, quaternary ammonium cations.

DESCRIPTION OF THE DRAWINGS

FIG. 1 is a result in Test Example 3 that shows the relationship between the peak area of compound AZD-2281 (as a standard) measured by HPLC and the concentration of the compound.

EMBODIMENTS

The followings further explain the general methods of the present invention. The compounds of the present invention may be prepared by the methods known in the art. The following illustrate the detailed preparation methods of the preferred compounds of the present invention. However, they are by no means limiting the preparation methods of the compounds of the present application.

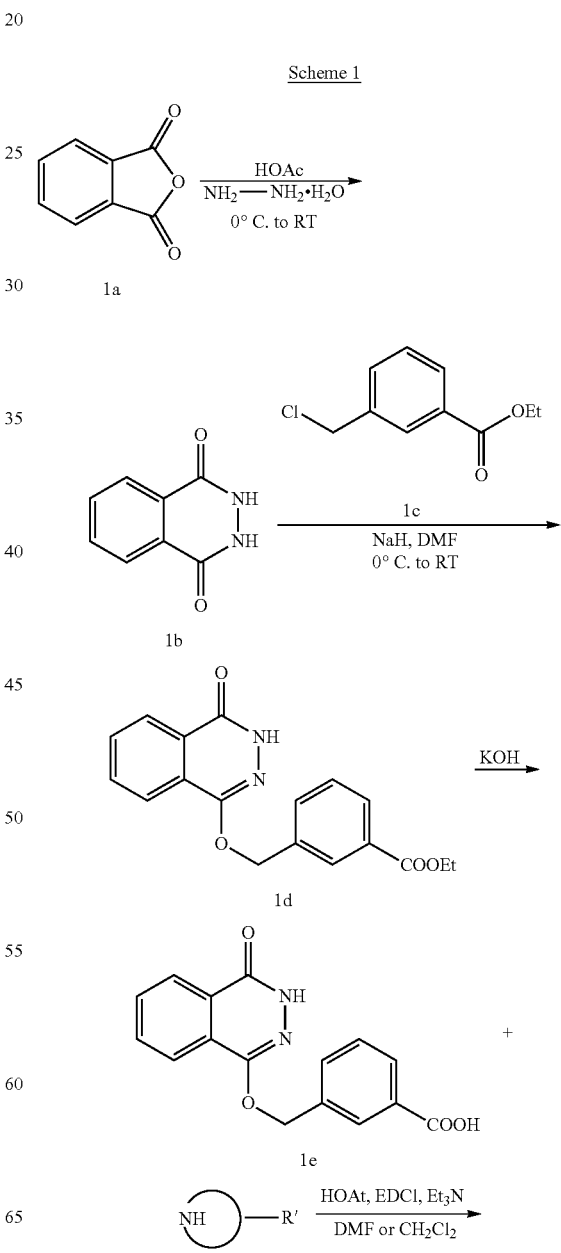

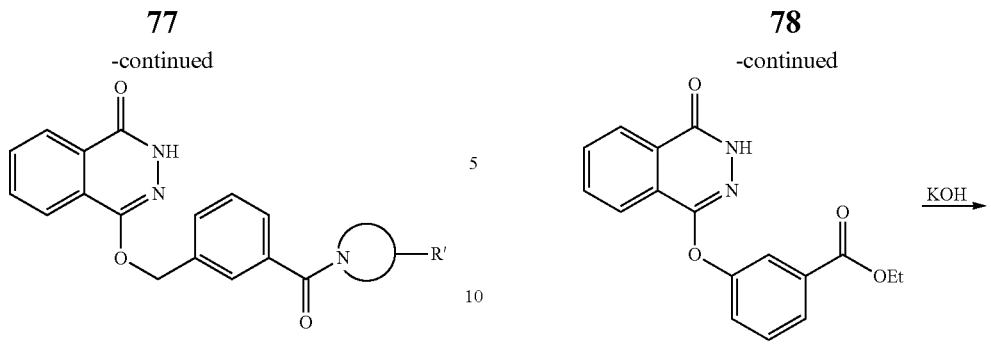

Phthalic anhydride (1a) was reacted with hydrazine hydrate in the presence of glacial acetic acid to give phthalhydrazide (1b), which was then reacted with ethyl 3-chloromethylbenzoate (1c) in the presence of sodium hydride to give ethyl 3-((4-oxo-3-1,4-dihydro-phthalazin-1-yl-oxyl)methyl)benzoate (1d), after that, 1d was hydrolyzed into 3-((4-oxo-3,4-dihydrophthalazin-1-yl-oxy)methyl)benzoic acid (1e) under alkali condition, 1e finally condensated with R' substituted nitrogen heterocycles, e.g. piperazine, piperidine, 4-hydroxypiperidine, tetrahydropyridine and 1,4-diazacycloheptane (homopiperazine) in the presence of 1-(3-dimethylaminopropyl)-3-ethylcarbodiimide hydrochloride (EDCI), triethylamine, 1-hydroxy-7-azabenzotriazole (HOAt) to generate target compounds, wherein the definition of R' is as described above.

Scheme 2

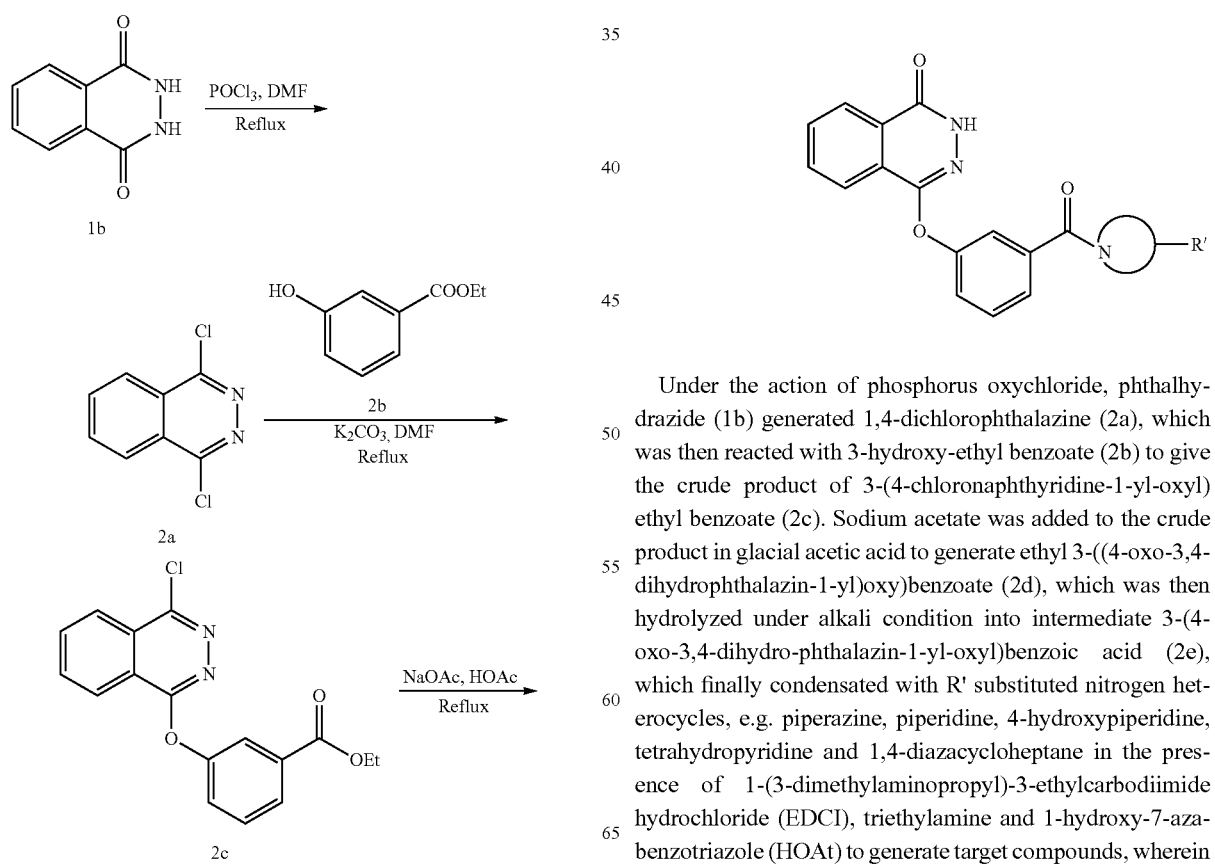

Under the action of phosphorus oxychloride, phthalhydrazide (1b) generated 1,4-dichlorophthalazine (2a), which was then reacted with 3-hydroxy-ethyl benzoate (2b) to give the crude product of 3-(4-chloronaphthyridine-1-yl-oxyl) ethyl benzoate (2c). Sodium acetate was added to the crude product in glacial acetic acid to generate ethyl 3-((4-oxo-3,4-dihydrophthalazin-1-yl)oxy)benzoate (2d), which was then hydrolyzed under alkali condition into intermediate 3-(4-oxo-3,4-dihydro-phthalazin-1-yl-oxyl)benzoic acid (2e), which finally condensated with R' substituted nitrogen heterocycles, e.g. piperazine, piperidine, 4-hydroxypiperidine, tetrahydropyridine and 1,4-diazacycloheptane in the presence of 1-(3-dimethylaminopropyl)-3-ethylcarbodiimide hydrochloride (EDCI), triethylamine and 1-hydroxy-7-azabenzotriazole (HOAt) to generate target compounds, wherein the definition of R' is as described above.

Scheme 3

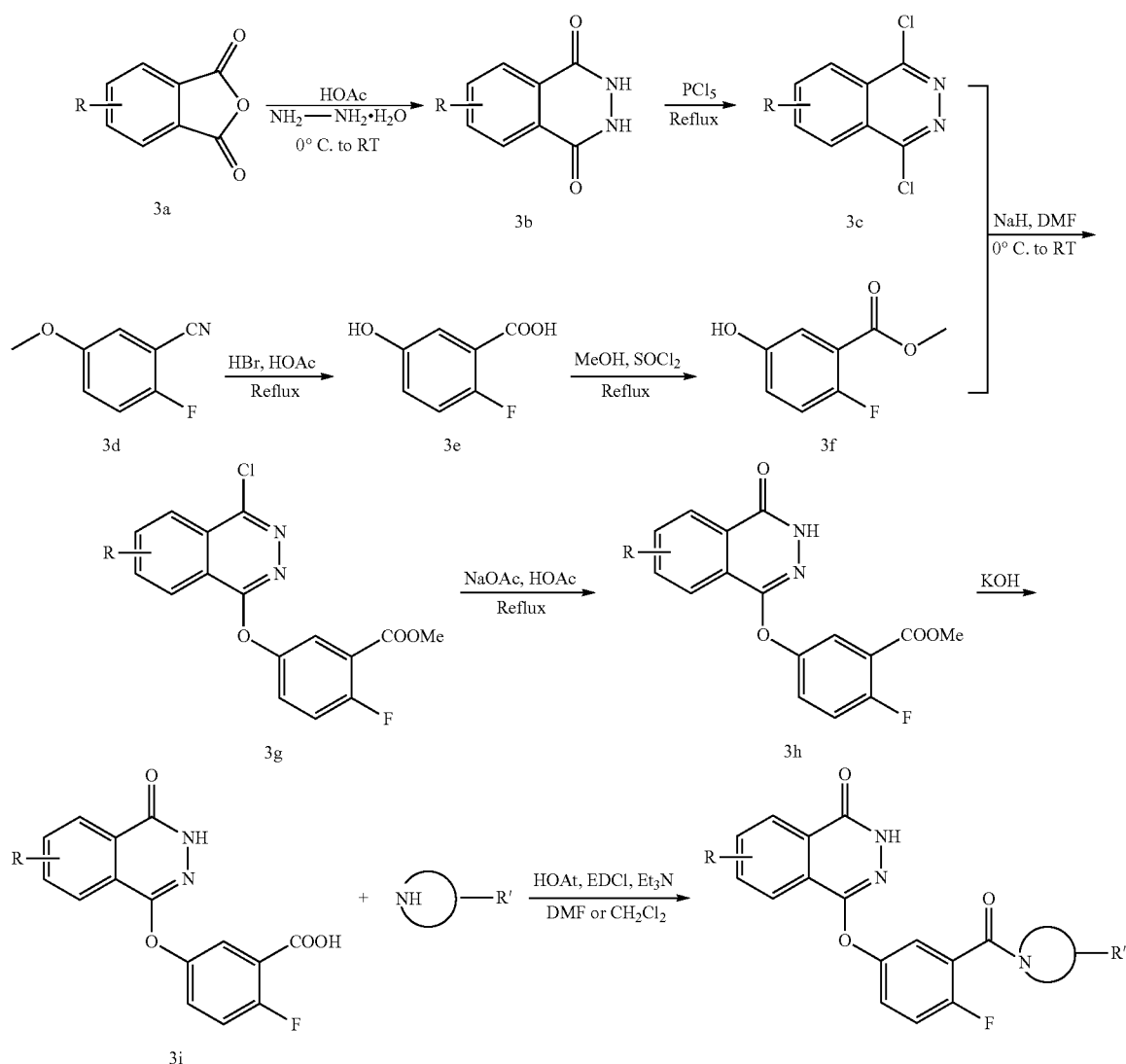

In the presence of hydrazine hydrate/glacial acetic acid, phthalic anhydride (3a) with substituent R was transformed into R-substituted phthalhydrazide (3b), which subsequently generated substituted dichlorophthalazine compounds (3c) under the action of phosphorus pentachloride. In another aspect, under the action of hydrobromic acid, 2-fluoro-5-methoxybenzonitrile (3d) was converted to 2-fluoro-5-hydroxybenzoic acid (3e), which was esterificated with methanol to give methyl 2-fluoro-5-hydroxybenzoate (3f). Under the action of sodium hydride, the prepared dichlorophthalazine compounds with substituent R (3c) was reacted with methyl 2-fluoro-5-hydroxybenzoate (3f) to give methyl 5-((4-chloronaphthyridine-1-yl)oxy)-2-fluorobenzoate with substituent R (3g), 3g was transformed into methyl 2-fluoro-5-((4-oxo-3,4-dihydro-phthalazin-1-yl)oxy)benzoate (3h) in the presence of AcOH/NaOAc under the reflux condition, 3h was then hydrolyzed under alkali condition into substituent-contained 2-fluoro-5-(4-oxo-3,4-dihydro-phthalazin-1-yl-oxyl)benzoic acid (3i), which finally condensated with R' substituted nitrogen heterocycles, e.g. piperazine, piperidine, 4-hydroxypiperidine, tetrahydropyridine and 1,4-diazacycloheptane in the presence of 1-(3-dimethylaminopropyl)-3-ethylcarbodiimide hydrochloride (EDCI), triethylamine and 1-hydroxy-7-azabenzotriazole (HOAt) to generate target compounds, wherein the definition of R and R' is as described above.

Scheme 4

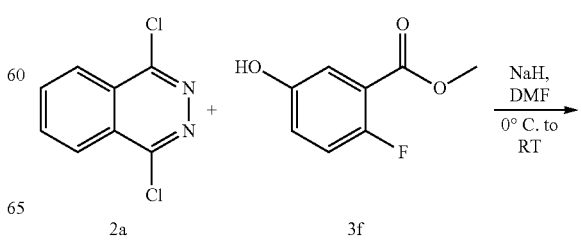

-continued

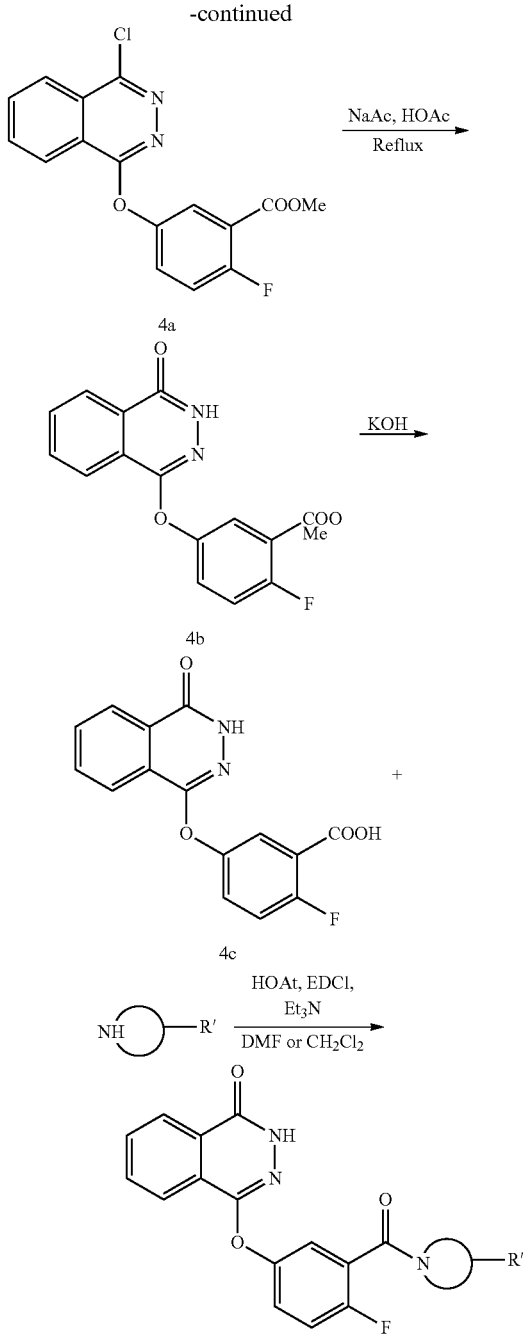

Under the action of sodium hydride, dichlorophthalazine (2a) was reacted with methyl 2-fluoro-5-hydroxybenzoate OD to give methyl 5-((4-chloronaphthyridine-1-yl)oxy)-2-fluorobenzoate (4a). 4a was transformed into methyl 2-fluoro-5-((4-oxo-3,4-dihydro-phthalazin-1-yl)oxyl)benzoate (4b) in the presence of AcOH/NaOAc under the reflux condition, 4b was then hydrolyzed under alkali condition into 2-fluoro-5-(4-oxo-3,4-dihydro-phthalazin-1-yl-oxyl)benzoic acid (4c), which finally condensated with R' substituted nitrogen heterocycles, e.g. piperazine, piperidine, 4-hydroxypiperidine, tetrahydropyridine and 1,4-diazacycloheptane in the presence of 1-(3-dimethylaminopropyl)-3-ethylcarbodiimide hydrochloride (EDCI), triethylamine and 1-hydroxy-7-azabenzotriazole (HOAt) to generate target compounds, wherein the definition of R' is as described above.

The present invention is further explained by the following examples. However, it shall be understood by a person skilled in the art that the present invention is not limited to these specific examples.

EXAMPLES

The structures of the compounds in the following examples were characterized by nuclear magnetic resonance (NMR) or/and mass spectrometry (ESI). NMR shift (δ) was given in the unit of $10^{-6}$ (ppm). $^1$H-NMR spectra was recorded in dimethyl sulfoxide-$d_6$ (DMSO-$d_6$) or CDCl$_3$ on a Varian Mercury-600 MHz NMR with tetramethylsilane (TMS) as an internal standard.

ESI-MS measurement was carried out using Finnigan LCQ Deca mass spectrometer.

High Performance Liquid Chromatography (HPLC) measurement was carried out on Agilent 1200 LC using the Phenomen C18 column (4.6 mm*150 mm, 0.4 μm).

IC$_{50}$ values were determined using Envision 2104 microplate reader (Perkin Elmer Inc.).

Thin layer chromatography was carried out using Yantai Huanghai HSGF254 silica gel plates. The silica gel plates used for thin layer chromatography (TLC) were 0.15 mm~0.2 mm. The silica gel plates used for separating and purifying products by TLC were 0.4 mm~0.5 mm.

Purified chromatographic column uses the silica gel as the carrier (300~400 mesh, produced by Yantai Huanghai co.).

The known starting materials of the present invention can be synthesized by using or according to the known methods in the art, or can be purchased from Alfa Aesar, Langcaster, TCI, Shanghai Shaoyuan Co. Ltd. and AstaTech (Chengdu) BioPharm. Co., Ltd.

Unless otherwise specified, the reactions in the examples were all carried out under argon or nitrogen atmosphere. Argon or nitrogen atmosphere refers to that the reaction flask is connected to an argon or nitrogen balloon with a volume of about 1 L. Hydrogenation was usually carried out under vacuum, filled with hydrogen, and repeated for three times. Unless otherwise specified, the reaction temperature in the examples was room temperature. Room temperature was the optimized reaction temperature, which was 20° C.-30° C.

The reaction progress in the examples was monitored by thin layer chromatography (TLC). The eluent systems used for the reactions include: A: dichloromethane-methanol system, B: n-hexane-ethyl acetate system, C: petroleum ether-ethyl acetate system. The volume ratios of the solvents were adjusted according to the different polarities of compounds.

The elution system of column chromatography used for purifying compounds and eluent system of TLC include A: dichloromethane-methanol system, B: n-hexane-ethyl acetate system, C: petroleum ether-ethyl acetate system. The volume ratios of the solvents were adjusted according to the different polarities of compounds. A small amount of alkaline or acidic agents such as triethylamine and acetic acid can be added for adjustment.

Intermediate Preparation Example 1

Synthesis of methyl 2-fluoro-5-hydroxybenzoate

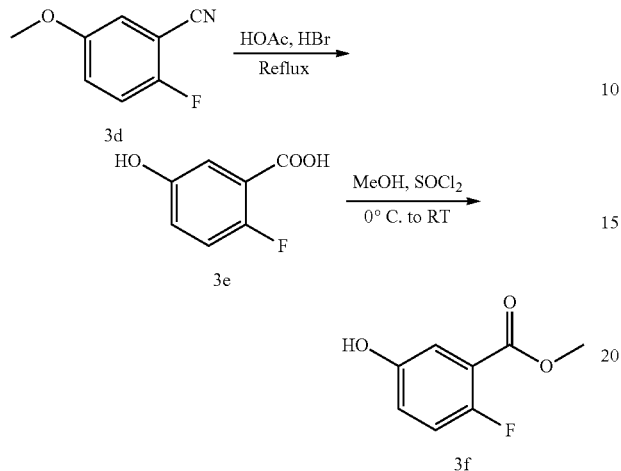

2-Fluoro-5-methoxybenzonitrile (3d, purchased from Alfa Aesar) (5 g, 33 mmol) was dissolved in hydrobromic acid (50 mL) and glacial acetic acid (30 mL), refluxed for 28 hours at 140° C., and then the reaction mixture was diluted with 100 mL ethyl acetate. The reaction mixture was then washed with 50 mL water and saturated sodium chloride solution successively for three times. The organic layers were combined and concentrated to give a crude product of 2-fluoro-5-hydroxybenzoic acid (3e), 2.88 g white solid (yield 56%). $^1$H NMR (600 MHz, DMSO-$d_6$) δ 7.19-7.17 (m, 1H), 7.08-7.04 (m, 1H), 6.95-6.92 (m, 1H); ESI-MS m/z: calculated for 156.02. found 154.91 [M−H]$^+$.

The obtained 2-fluoro-5-hydroxybenzoic acid (3e) (780 mg, 5 mmol) was dissolved in 100 mL methanol. Thionyl chloride (0.8 mL, 10 mmol) was added dropwise under the condition of ice bath (0° C.) and stirring, and then refluxed for two hours. The reaction solution was concentrated, and then column chromatography (petroleum ether:ethyl acetate=2:1) was performed to isolate methyl 2-fluoro-5-hydroxybenzoate (3f), 833 mg white solid (yield 98%). $^1$H NMR (600 MHz, DMSO-$d_6$) δ 9.73 (s, 1H), 7.20-7.18 (m, 1H), 7.13-7.09 (m, 1H), 6.99-6.97 (m, 1H), 3.80 (s, 3H); ESI-MS m/z: calculated for 170.04. found 171.25 [M+H]$^+$.

Intermediate Preparation Example 2

Preparation of 3-(((4-oxo-3,4-dihydrophthalazin-1-yl)oxy)methyl)benzoic acid (1e)

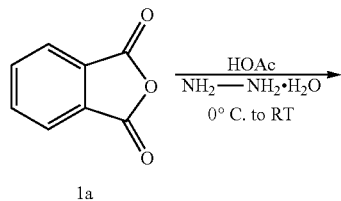

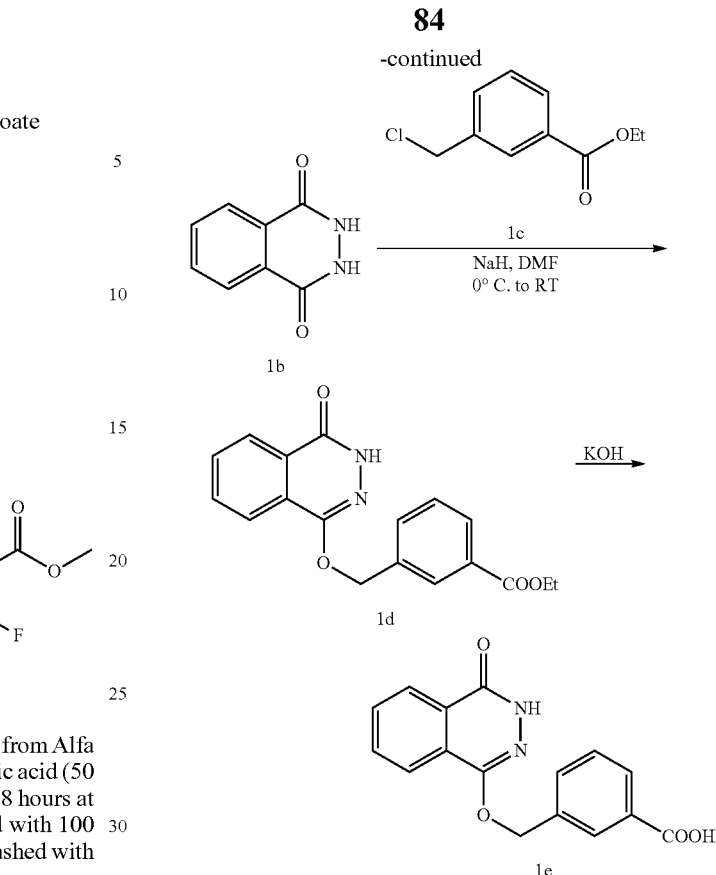

Phthalic anhydride (1a, purchased from Shanghai Shaoyuan Co. Ltd.) (10 g, 67.6 mmol) was dissolved in glacial acetic acid (100 mL), hydrazine hydrate (20 mL) was added dropwise under the condition of ice bath (0° C.) and stirring, and then refluxed for two hours at 125° C. The reaction was monitored by TLC. The solution was cooled to room temperature, filtrated and washed with water until the pH of the filtrate was 6.0, and then dried to give phthalhydrazide (1b), 10.5 g white solid (yield 96%). ESI-MS m/z calculated for: 162.04. found: 173.15 [M+H]$^+$.

Phthalhydrazide (1b) (10 g, 61.7 mmol) was dissolved in dried N,N-dimethylformamide (100 mL) in a round-bottom flask. Sodium hydride (1.63 g, 67.9 mmol) was added at 0° C., and then stirred for half an hour. Ethyl 3-chloromethylbenzoate (1c, purchased from Shanghai Shaoyuan Co. Ltd.) (13.49 g, 67.9 mmol) dissolved in N,N-dimethylformamide (20 mL) solution was added slowly dropwise at room temperature and reacted for 24 hours, and then ethyl acetate was added. The reaction solution was successively washed with 50 mL saturated sodium bicarbonate and saturated sodium chloride solution for three times, the organic layer was dried and concentrated. Column chromatography was performed for the crude product (petroleum ether:ethyl acetate=10:1) to give ethyl 3-(((4-oxo-3-1,4-dihydrophthalazin-1-yl)oxy)methyl)benzoate (1d), 6 g white solid (yield 30%). $^1$H NMR (600 MHz, DMSO-$d_6$): δ 11.94 (s, 1H), 8.24 (d, 1H, J=7.50 Hz), 7.97-7.95 (m, 1H), 7.93-7.87 (m, 3H), 7.85-7.83 (m, 1H), 7.57-7.56 (m, 1H), 7.48-7.45 (m, 1H), 5.23 (s, 2H), 4.29-4.25 (m, 2H), 1.28-1.25 (m, 3H); ESI-MS m/z: calculated for 324.1. found 346.9 [M+Na]$^+$.

Ethyl 3-(((4-oxo-3-1,4-dihydro-phthalazin-1-yl)oxyl)methyl)benzoate (1d) (1 g, 3.1 mmol) was completely dissolved in 1M potassium hydroxide aqueous solution, concentrated hydrochloric acid was added dropwise until a white solid was completely separate out, stirred for one hour and then filtrated, washed with water until the filtrate become faintly acid to give 3-(((4-oxo-3,4-dihydrophthalazin-1-yl)oxy)methyl)benzoic acid (1e), a crude product of 0.9 g white solid (yield 98%). ESI-MS m/z: calculated for 269.08. found 270.02 [M+11]+.

Intermediate Preparation Example 3

Synthesis of 3-(4-oxo-3,4-dihydro-phthalazin-1-yl-oxyl)benzoic acid (2e)

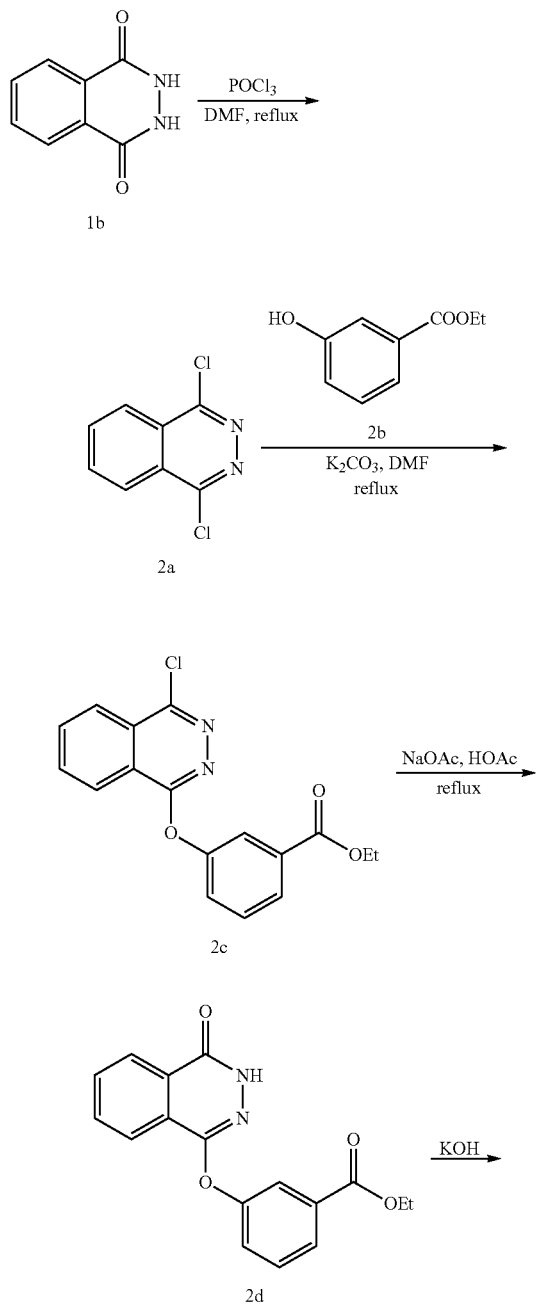

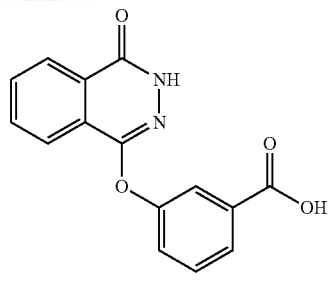

Phthalhydrazide (1b) (1 g, 6.2 mmol), phosphorus oxychloride (2.8 g, 18.6 mmol) and N,N-dimethylformamide were added into a reaction flask successively and refluxed for two hours, and then the reaction solution was carefully and slowly poured into ice water, and then warmed to room temperature, filtrated to remove the solid, the filtrate was concentrated under decreased pressure, and rapid column chromatography was performed with dichloromethane to give 1,4-dichlorophthalazine (2a), 281 mg pale yellow solid (yield 22.8%).

1,4-Dichlorophthalazine (2a) (277 mg, 1.4 mmol), N,N-dimethylformamide (10 mL), potassium carbonate (192 mg, 1.4 mmol), and ethyl 3-hydroxybenzoate (2b, purchased from Shanghai Shaoyuan Co. Ltd.) (231 mg, 1.4 mol) were added successively at room temperature, refluxed for two hours at 120° C. The reaction mixture was diluted with 50 mL ethyl acetate, then the reaction solution was washed successively with 50 mL saturated sodium bicarbonate solution and saturated sodium chloride solution for three times, the organic phases were combined and concentrated to give a crude product of ethyl 3-((4-chloronaphthyridine-1-yl)oxy)benzoate (2c), 340 mg white solid (yield 74%).

The crude product of ethyl 3-((4-chloronaphthyridine-1-yl)oxy)benzoate (2c) (670 mg, 2 mmol), acetic acid (20 mL) and sodium acetate (420 mg, 3 mmol) were added into a reaction flask successively, refluxed for one hour and then diluted with 50 mL ethyl acetate. The reaction solution was washed successively with 50 mL saturated sodium bicarbonate solution and saturated sodium chloride solution for three times, the organic phases were combined and concentrated to give a crude product of ethyl 3-((4-oxo-3,4-dihydro-phthalazin-1-yl)oxy)benzoate (2d), 589 mg white solid (yield 95%). $^1$H NMR (600 MHz, DMSO-$d_6$): δ 11.95 (s, 1H), 8.26 (d, 1H, J=7.7 Hz), 8.12 (d, 1H, J=7.7 Hz), 8.01-8.00 (m, 1H), 7.97-7.95 (m, 1H), 7.83-7.80 (m, 2H), 7.60-7.58 (m, 2H), 4.27 (q, J=7.2 Hz, 2H), 1.30 (t, J=7.2 Hz, 3H); ESI-MS m/z: calculated for 310.1. found 309.4 [M–H]+.

Ethyl 3-((4-oxo-3,4-dihydrophthalazin-1-yl)oxy)benzoate (2d) (1 g, 3.2 mmol) obtained in the last step was dissolved in 1M potassium hydroxide solution, stirred for two hours at room temperature, and then concentrated hydrochloric acid was added dropwise to adjust pH=3, stirred for two hours at room temperature, filtrated to give a white solid intermediate 3-(4-oxo-3,4-dihydro-phthalazin-1-yl-oxyl)benzoic acid (2e), 893 mg white solid (yield 99%). $^1$H NMR (600 MHz, DMSO-$d_6$): δ 11.96 (s, 1H), 8.26 (d, 1H, J=7.9 Hz), 8.12 (d, 1H, J=7.9 Hz), 8.02-7.99 (m, 1H), 7.97-7.94 (m, 1H), 7.82-7.81 (m, 2H), 7.56-7.55 (m, 2H); ESI-MS m/z: calculated for 282.1. found 281.1 [M–H]+.

Intermediate Preparation Example 4

Synthesis of 2-fluoro-5-(8-chloro-4-oxo-3,4-dihydro-phthalazin-1-yl-oxyl)benzoic acid (5f)

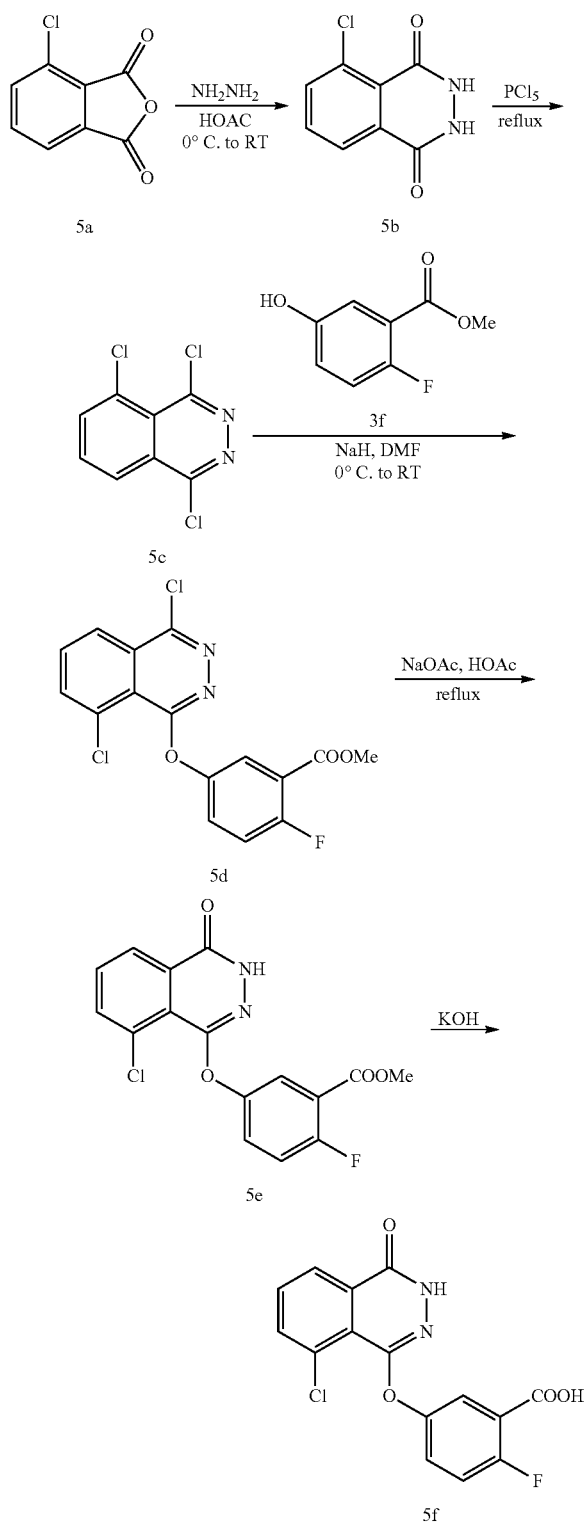

3-Chloro-phthalic anhydride (5a, purchased from TCI) (10 g, 54.95 mmol) was dissolved in glacial acetic acid (100 mL), and hydrazine hydrate (20 mL) was added dropwise at 0° C., and then refluxed for two hours at 125° C. When the reaction was completed, the solution was cooled down to room temperature, filtrated, and washed with water until the filtrate pH 6.0, and then dried to give 5-chloro-2,3-dihydrophthalazin-1,4-dione (5b), 10.08 g white solid (yield 93%).

5-Chloro-2,3-dihydrophthalazin-1,4-dione (5b) (1 g, 5.10 mmol) and phosphorus pentachloride (2.5 g, 12 mmol) were added into a reaction flask successively, and gradually warmed to 150° C. After the solid was melted, the mixture was reflux for two hours at 150° C., and then cooled down to room temperature. 200 mL dried dichloromethane was added, filtrated to remove insoluble substances, and the filtrate was concentrated. Rapid column chromatography was performed with dichloromethane, and the solvent was dried to give 1,4-dichloro-5-chloro-phthalazine (5c), 307 mg white solid (yield 26%).

Methyl 2-fluoro-5-hydroxy benzoate (30 (940 mg, 5.5 mmol) was dissolved in N,N-dimethylformamide (2 mL), and sodium hydride (140 mg, 6 mmol) was added slowly. Half an hour later, the reaction solution was slowly dropwise added to the N, N-dimethylformamide (4 mL) solution of 1,4-dichloro-5-chloro-phthalazine (5c) (1000 mg, 4.3 mmol), and stirred for another one hour. The reaction solution was diluted with 250 mL ethyl acetate, and washed successively with 50 mL saturated sodium bicarbonate solution and saturated sodium chloride solution for three times, the organic phases were combined, concentrated and dried to give methyl 5-((4,8-dichlorophthalazin-1-yl)oxy)-2-fluorobenzoate (5d), 1.8 g white solid (yield 95%).

Methyl 5-((4,8-dichlorophthalazin-1-yl)oxy)-2-fluorobenzoate (5d) (700 mg, 1.9 mmol), acetic acid (20 mL) and sodium acetate (420 mg, 3 mmol) were added into a reaction flask successively, the mixture was refluxed for one hour, and diluted with 50 mL ethyl acetate. The reaction solution was washed with 50 mL saturated sodium bicarbonate solution and saturated sodium chloride solution successively for three times, the organic layers were combined, concentrated and dried to give methyl 5-((8-chloro-4-oxo-3,4-dihydrophthalazin-1-yl)oxy)-2-fluorobenzoate (5e), 650 mg white solid (yield 95%). $^1$H NMR (600 MHZ, DMSO-$d_6$): δ 12.12 (s, 1H), 8.13 (d, J=8.0 Hz, 1H), 7.95-8.00 (m, 1H), 7.83-7.87 (m, 1H), 7.74-7.77 (m, 1H), 7.61-7.64 (m, 1H), 7.42-7.47 (m, 1H), 3.86 (s, 3H); ESI-MS m/z; calculated for 348.0. found 371.6 [M+Na]$^+$.

Methyl 5-((8-chloro-4-oxo-3,4-dihydrophthalazin-1-yl)oxy)-2-fluorobenzoate (5e) (1 g, 2.87 mmol) was dissolved in 1M potassium hydroxide solution, stirred for two hours at room temperature, and then concentrated hydrochloric acid was added dropwise to adjust the reaction mixture pH=3, stirred for two hours at room temperature, and filtrated to give 2-fluoro-5-(8-chloro-4-oxo-3,4-dihydro-phthalazin-1-yl-oxyl)benzoic acid (5f), 900 mg white solid (yield 90%). ESI-MS m/z: calculated for 334.02. found 357.10 [M+Na]$^+$.

The procedures for synthesizing 2-fluoro-5-(4-oxo-3,4-dihydro-phthalazin-1-yl-oxyl)benzoic acid substituted by 5-nitro and 5-fluoro are similar with the synthesis of 2-fluoro-5-(8-chloro-4-oxo-3,4-dihydro-phthalazin-1-yl-oxyl)benzoic acid (Intermediate Preparation Example 4).

Intermediate Preparation Example 5

Synthesis of 2-fluoro-5-(4-oxo-3,4-dihydro-phthalazin-1-yl-oxyl)benzoic acid (4d)

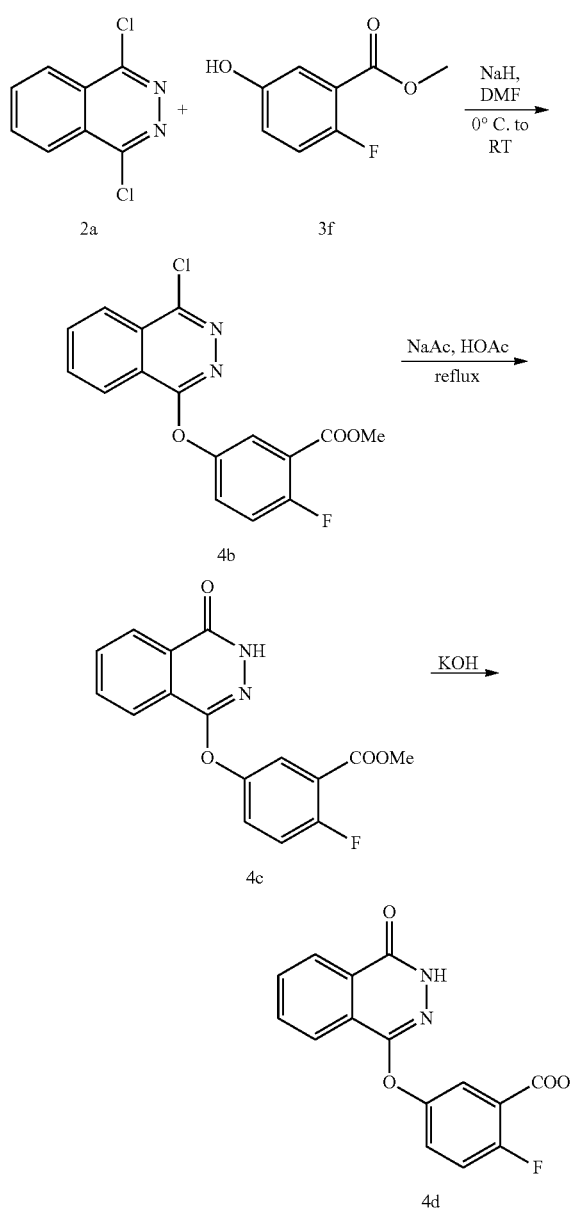

The procedures for synthesizing 2-fluoro-5-(4-oxo-3,4-dihydro-phthalazin-1-yl-oxyl)benzoic acid (4d) are similar with the synthesis of 2-fluoro-5-(8-chloro-4-oxo-3,4-dihydro-phthalazin-1-yl-oxyl)benzoic acid (5f) (Intermediate Preparation Example 4), except that the starting material 1,4-dichloro-5-chloro-phthalazine (5c) was replaced by 1,4-dichlorophthalazine (2a).

2-Fluoro-5-(4-oxo-3,4-dihydro-phthalazin-1-yl-oxyl) benzoic acid (4d), a white solid. $^1$H NMR (600 MHz, DMSO) δ 11.93 (s, 1H), 8.24 (d, J=7.8 Hz, 1H), 8.11 (d, J=7.8 Hz, 1H), 7.99-7.96 (m, 1H), 7.95-7.92 (m, 1H), 7.73-7.58 (m, 1H), 7.60-7.58 (m, 1H), 7.40-7.36 (m, 1H); ESI-MS m/z calculated for 300.1. found 301.24 [M+H]$^+$.

Intermediate Preparation Example 6

Synthesis of 1-tertbutoxycarbonyl-4-(4-fluorobenzoyl)piperazine (6c)

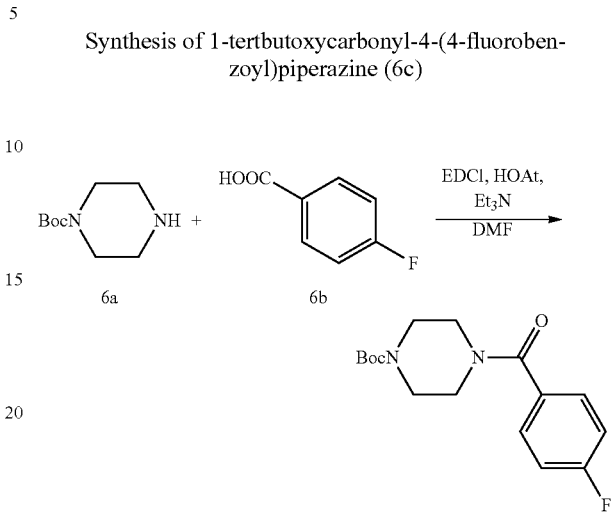

4-Fluorobenzoic acid (6b) (7 g, 50 mmol) was dissolved in dichloromethane (100 mL), and 1-(3-dimethylaminopropyl)-3-ethylcarbodiimide hydrochloride (EDCI) (10.5 g, 55 mmol), triethylamine (7.7 mL, 55 mmol) and 1-hydroxy-7-azabenzotriazole (HOAt) (7.5 g, 55 mmol) were added successively, stirred for half an hour at room temperature, and then 1-tertbutoxycarbonylpiperazine (6a) (10.2 g, 55 mmol) was added and stirred overnight. On the next day, water was added to quench the reaction. The reaction solution was washed successively with 50 mL saturated sodium bicarbonate solution and saturated sodium chloride solution for three times, the organic phases were concentrated to give 1-tertbutoxycarbonyl-4-(4-fluorobenzoyl)piperazine (6c), 14.8 g white solid (yield 96%). ESI-MS m/z calculated for: 308.15. found: 309.25 [M+H]$^+$.

Intermediate Preparation Example 7

Synthesis of 1-tertbutoxycarbonyl-4-(cyclopropylmethyl)piperazine

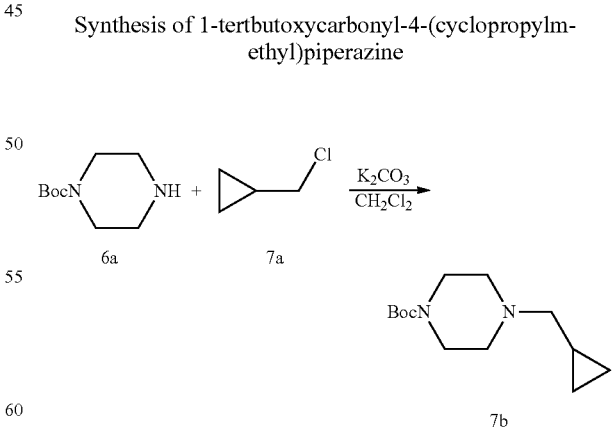

1-Tertbutoxycarbonylpiperazine (6a) (1.86 g, 10 mmol) was dissolved in dichloromethane (20 mL), and anhydrous potassium carbonate (829 mg, 6 mmol) was added. The dichloromethane solution of chloromethyl cyclopropane (7a) (1.1 mL, 12 mmol) was added dropwise, and reacted overnight at room temperature, after that, the reaction mixture was washed with water. The water layer was extracted with dichloromethane for twice, the organic phases were combined, washed successively with 50 mL saturated sodium bicarbonate solution and saturated sodium chloride solution for three times, dried with anhydrous sodium sulfate. Column chromatography (petroleum ether:ethyl acetate 2:1) was performed to isolate white solid powder 1-tertbutoxycarbonyl-4-(cyclopropylmethyl)piperazine (7b), 2.01 g white solid (yield 79.0%). ESI-MS m/z calculated for: 240.18. found: 241.05 [M+H]$^+$.

Intermediate Preparation Example 8

Synthesis of 1-tertbutoxycarbonyl-4-(isopropylamineformyl)piperazine

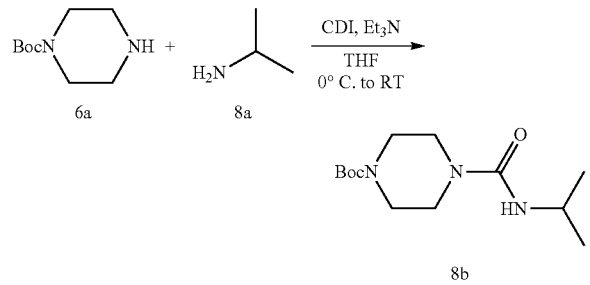

N,N'-carbonyldiimidazole (CDI) (1.62 g, 10 mmol) was added into the tetrahydrofuran (20 mL)/triethylamine (1.36 mL, 10 mmol) of 1-tertbutoxycarbonylpiperazine (6a) (1.86 g, 10 mmol) in ice bath (0° C.) under the protection of nitrogen, stirred for one hour, and then isopropamide (8a) (0.71 g, 12 mmol) was added, reacted overnight at room temperature. The reaction solution was diluted with water, extracted with ethyl acetate for three times, the organic phases were combined and washed with 50 mL saturated sodium chloride solution for three times. The organic phases were dried with anhydrous sodium sulfate. The organic phases were concentrated to give 1-tertbutoxycarbonyl-4-(isopropylformamyl) piperazine (8b), 1.68 g pale yellow solid (yield 62%). ESI-MS m/z calculated for: 271.19. found: 294.28 [M+Na]$^+$.

When the substituent at the fourth position of tertbutoxycarbonylpiperazine is aryl, alkane or formamyl, and the substituent at the fourth position of 1,4-diazacycloheptane is aryl or alkane, the synthetic methods are similar with the above Intermediate Preparation Examples 6, 7, and 8, and are not described herein.

Example 1

Compound 1 of the present invention was prepared according to Scheme 1.
1-Tertbutoxycarbonyl-4-(cyclopropanecarbonyl)piperazine (190 mg, 0.75 mmol) was dissolved in dichloromethane, and then trifluoroacetic acid (1 mL) was added. The reaction mixture was stirred at room temperature until complete reaction, and then washed with saturated sodium bicarbonate solution for three times. The organic phases were concentrated to give 112 mg (yield 97%) pale yellow solid of N-(cyclopropanecarbonyl) piperazine for use.
3-((4-Oxo-3,4-dihydro-phthalazin-1-yl-oxy)methyl)benzoic acid (148 mg, 0.5 mmol) was dissolved in N,N-dimethylformamide, and then 1-(3-dimethylaminopropyl)-3-ethyl-carbodiimide hydrochloride (EDCI) (115 mg, 0.63 mmol), triethylamine (83.6 µL, 0.63 mmol) and 1-hydroxy-7-azabenzotriazole (HOAt) (81.6 mg, 0.63 mmol) were added successively. The mixture was stirred at room temperature for half an hour, and then N-(cyclopropanecarbonyl) piperazine was added and reacted at room temperature overnight, and then the reaction was quenched with water. The mixture was extracted with ethyl acetate, and washed with water for two times. The organic phases were combined and washed with saturated saline, dried with anhydrous sodium sulfate, concentrated and then purified by column chromatography (dichloromethane:methanol=20:1) to give a white solid 173 mg (yield 88%). $^1$H NMR (600 MHz, DMSO-d$_6$): δ 11.94 (s, 1H), 8.21 (d, 1H, J=7.68 Hz), 7.99 (d, 1H, J=7.86 Hz), 7.94-7.92 (m, 1H), 7.90-7.88 (m, 1H), 7.61 (d, 1H, J=7.62 Hz), 7.55 (s, 1H), 7.49 (t, 1H, J=7.62 Hz), 7.39 (d, 1H, J=7.62 Hz), 5.38 (s, 2H), 3.87-3.47 (m, 8H), 1.95 (brs, 1H), 0.69-0.72 (m, 4H); ESI-MS m/z: calculated for 432.1. found 455.1 [M+Na]$^+$.

Example 2

Compound 2 of the present invention was prepared according to Scheme 1. The synthetic method was similar with Example 1, except that the N-(cyclopropanecarbonyl) piperazine was replaced. Firstly, 4-phenylcarbonyl piperidine (corresponds to A ring with substituent R' of Formula (I) in Compound 2) was prepared, and obtained as white solid. $^1$H NMR (600 MHz, DMSO-d$_6$): δ 11.93 (s, 1H), 8.20 (d, 1H, J=8.64 Hz), 8.00-7.98 (m, 1H), 7.89-7.87 (m, 2H), 7.60 (d, 1H, J=7.14 Hz), 7.54 (br, 1H), 7.49-7.40 (m, 7H), 5.37 (s, 2H), 3.64-3.34 (m, 8H); ESI-MS m/z: calculated for 468.1. found 490.9 [M+Na]$^+$.

Example 3

Compound 3 of the present invention was prepared according to Scheme 1. The synthetic method was similar with Example 1, except that the N-(cyclopropanecarbonyl) piperazine was replaced. Firstly, 4-propionyl piperazine (corresponds to A ring with substituent R' of Formula (I) in Compound 3) was prepared, and obtained as white solid. $^1$H NMR (600 MHz, DMSO-d$_6$): δ 11.94 (s, 1H), 8.21 (d, 1H, J=7.80 Hz), 7.99 (d, 1H, J=7.74 Hz), 7.94-7.92 (m, 1H), 7.90-7.87 (m, 1H), 7.60 (d, 1H, J=7.68 Hz), 7.54 (s, 1H), 7.49 (t, 1H, J=7.62 Hz), 7.38 (d, 1H, J=7.56 Hz), 5.38 (m, 2H), 3.63-3.41 (m, 8H), 2.30 (br, 2H), 0.97 (t, 3H, J=7.26 Hz); ESI-MS m/z: calculated for 420.1. found 443.1 [M+Na]$^+$.

Example 4

Compound 4 of the present invention was prepared according to Scheme 1. The synthetic method was similar with Example 1, except that the N-(cyclopropanecarbonyl) piperazine was replaced. Firstly, 4-(cyclohexanecarbonyl) piperazine (corresponds to A ring with substituent R' of Formula (I) in Compound 4) was prepared, and obtained as white solid. $^1$H NMR (600 MHz, DMSO-d$_6$): δ 11.94 (s, 1H), 8.21 (d, 1H, J=7.86 Hz), 7.99 (d, 1H, J=7.86 Hz), 7.94-7.88 (m, 1H), 7.90-7.88 (m, 1H), 7.60 (d, 1H, J=7.26 Hz), 7.54 (s, 1H), 7.49 (t, 1H, J=7.68 Hz), 7.38 (d, 1H, J=7.50 Hz), 5.38 (s, 2H), 3.64-3.40 (m, 8H), 2.09-2.06 (m, 3H), 1.60-1.67 (m, 5H), 1.29-1.30 (m, 3H); ESI-MS m/z: calculated for 474.2. found 497.2 [M+Na]$^+$.

Example 5

Compound 5 of the present invention was prepared according to Scheme 1. The synthetic method was similar with Example 1, except that the N-(cyclopropanecarbonyl) piperazine was replaced. Firstly, 4-(cyclopentanecarbonyl) piperazine (corresponds to A ring with substituent R' of Formula (I) in Compound 5) was prepared, and obtained as white solid. $^1$H NMR (600 MHz, DMSO-$d_6$): δ 11.94 (s, 1H), 8.21 (d, 1H, J=7.86 Hz), 7.99 (d, 1H, J=7.80 Hz), 7.94-7.92 (m, 1H), 7.90-7.87 (m, 1H), 7.60 (d, 1H, J=7.62 Hz), 7.54 (s, 1H), 7.48 (t, 1H, J=7.62 Hz), 7.38 (d, 1H, J=7.62 Hz), 5.38 (s, 2H), 3.56-3.49 (m, 8H), 2.96-2.90 (m, 1H), 1.49-1.73 (m, 8H); ESI-MS m/z: calculated for 460.2. found 483.2 [M+Na]$^+$.

Example 6

Compound 6 of the present invention was prepared according to Scheme 1. The synthetic method was similar with Example 1, except that the N-(cyclopropanecarbonyl) piperazine was replaced. Firstly, 4-acetyl piperazine (corresponds to A ring with substituent R' of Formula (I) in Compound 6) was prepared, and obtained as white solid. $^1$H NMR (600 MHz, DMSO-$d_6$): δ 11.94 (s, 1H), 8.21 (d, 1H, J=7.68 Hz), 7.99 (d, 1H, J=7.92 Hz), 7.95-7.92 (m, 1H), 7.90-7.88 (m, 1H), 7.61 (d, 1H, J=7.74 Hz), 7.54 (s, 1H), 7.48 (m, 1H), 7.39 (d, 1H, J=7.62 Hz), 5.38 (s, 2H), 3.63-3.45 (m, 8H), 2.07 (s, 3H); ESI-MS m/z: calculated for 406.1. found 429.1 [M+Na]$^+$.

Example 7

Compound 7 of the present invention was prepared according to Scheme 2. The preparation of Compound 7, 4-(3-(4-(cyclopropanecarbonyl)piperazine-1-carbonyl)phenoxy)-2H-phthalazin-1-one:

1-Tertbutoxycarbonyl-4-(cyclopropanecarbonyl) piperazine (254 mg, 1 mmol) was dissolved in dichloromethane, and then trifluoroacetic acid (1.5 mL) was added. The reaction mixture was stirred at room temperature until completed, and then washed with saturated sodium bicarbonate solution for three times. The organic phases were concentrated. N-(cyclopropanecarbonyl) piperazine was obtained for use.

3-(4-oxo-3,4-dihydro-phthalazin-1-yl-oxyl)benzoic acid (54 mg, 0.3 mmol) was dissolved in N,N-dimethylformamide, and then 1-(3-dimethylaminopropyl)-3-ethylcarbodiimide hydrochloride (EDCI) (220 mg, 1.2 mmol), triethylamine (150 μL, 1.2 mmol) and 1-hydroxy-7-azabenzotriazole (HOAt) (165 mg, 1.2 mmol) were added successively. The mixture was stirred at room temperature for half an hour, and then N-(cyclopropanecarbonyl) piperazine was added and reacted at room temperature overnight, and then the reaction was quenched with water, extracted with ethyl acetate, and washed with water for three times. The organic phases were combined and washed with saturated saline, dried with anhydrous sodium sulfate, and concentrated for column chromatography isolation (dichloromethane:methanol=20:1) to give Compound 7. A white solid was obtained. $^1$H NMR (600 MHz, DMSO-$d_6$): δ 11.98 (s, 1H), 8.27 (d, 1H, J=7.38 Hz), 8.10 (d, 1H, J=7.74 Hz), 7.99-8.01 (m, 1H), 7.94-7.96 (m, 1H), 7.52 (t, 1H, J=7.86 Hz), 7.39-7.38 (m, 2H), 7.28 (d, 1H, J=7.62 Hz), 3.33-3.81 (m, 8H), 1.96 (brs, 1H), 0.69-0.74 (m, 4H); ESI-MS m/z: calculated for 418.16. found 417.89 [M−H]$^+$.

Example 8

Compound 8 of the present invention was prepared according to Scheme 2. The synthetic method was similar with Example 7, except that the N-(cyclopropanecarbonyl) piperazine was replaced. Firstly, 4-propionyl piperazine (corresponds to A ring with substituent R' of Formula (I) in Compound 8) was prepared, and obtained as white solid. $^1$H NMR (600 MHz, DMSO-$d_6$): δ 11.98 (s, 1H), 8.27 (d, 1H, J=7.62 Hz), 8.10 (d, 1H, J=7.74 Hz), 7.99-8.01 (m, 1H), 7.94-7.96 (m, 1H), 7.51 (t, 1H, J=7.83 Hz), 7.39-7.36 (m, 2H), 7.28 (d, J=7.62 Hz, 1H), 3.60-3.48 (m, 8H), 2.33-2.29 (brs, 2H), 0.97 (t, 3H, J=7.38 Hz); ESI-MS m/z: calculated for 406.16. found 407.09 [M+H]$^+$.

Example 9

Compound 9 of the present invention was prepared according to Scheme 2. The synthetic method was similar with Example 7, except that the N-(cyclopropanecarbonyl) piperazine was replaced. Firstly, 4-benzoyl piperazine (corresponds to A ring with substituent R' of Formula (I) in Compound 9) was prepared, and obtained as white solid. $^1$H NMR (600 MHz, DMSO-$d_6$): δ 11.98 (s, 1H), 8.26 (d, 1H, J=7.80 Hz), 8.09-8.10 (m, 1H), 7.98-8.00 (m, 1H), 7.96-7.93 (m, 1H), 7.49-7.52 (m, 1H), 7.43-7.44 (m, 3H), 7.40-7.36 (m, 4H), 7.28-7.27 (m, 1H), 3.64-3.40 (m, 8H); ESI-MS m/z: calculated for 454.16. found 453.31 [M−H]$^+$.

Example 10

Compound 10 of the present invention was prepared according to Scheme 2. The synthetic method was similar with Example 7, except that the N-(cyclopropanecarbonyl) piperazine was replaced. Firstly, 4-(cyclohexanecarbonyl) piperazine (corresponds to A ring with substituent R' of Formula (I) in Compound 10) was prepared, and obtained as white solid. $^1$H NMR (600 MHz, DMSO-$d_6$): δ 11.98 (s, 1H), 8.26 (d, 1H, J=7.56 Hz), 8.10 (d, 1H, J=7.80 Hz), 7.98-8.01 (m, 1H), 7.93-7.96 (m, 1H), 7.51 (t, 1H, J=7.86 Hz), 7.36-7.39 (m, 2H), 7.27 (d, 1H, J=7.56 Hz), 3.33-3.65 (m, 8H), 2.50-2.64 (m, 1H), 1.68-1.67 (m, 2H), 1.62-1.60 (m, 3H), 1.21-1.33 (m, 5H). ESI-MS m/z: calculated for 460.20. found 460.98 [M+H]$^+$.

Example 11

Compound 11 of the present invention was prepared according to Scheme 2. The synthetic method was similar with Example 7, except that the N-(cyclopropanecarbonyl) piperazine was replaced. Firstly, 4-(cyclopentanecarbonyl) piperazine (corresponds to A ring with substituent R' of Formula (I) in Compound 11) was prepared, and obtained as white solid. $^1$H NMR (600 MHz, DMSO-$d_6$): δ 11.98 (s, 1H), 8.26 (d, 1H, J=7.68 Hz), 8.10 (d, 1H, J=7.98 Hz), 7.98-8.02 (m, 1H), 7.92-7.97 (m, 1H), 7.51 (m, 1H), 7.33-7.40 (m, 2H), 7.27 (d, 1H, J=7.80 Hz), 3.33-3.65 (m, 8H), 2.87-3.02 (m, 1H), 1.68-1.80 (m, 2H), 1.53-1.67 (m, 6H); ESI-MS m/z: calculated for 446.20. found 446.64 [M+H]$^+$.

Example 12

Compound 12 of the present invention was prepared according to Scheme 2. The synthetic method was similar with Example 7, except that the N-(cyclopropanecarbonyl) piperazine was replaced. Firstly, 4-acetyl piperazine (corresponds to A ring with substituent R' of Formula (I) in Compound 12) was prepared, and obtained as white solid. $^1$H NMR (600 MHz, DMSO-$d_6$): δ 11.98 (s, 1H), 8.26 (d, 1H, J=7.74 Hz), 8.10 (d, 1H, J=7.98 Hz), 7.99-8.01 (m, 1H), 7.94-7.96 (m, 1H), 7.51 (t, 1H, J=7.83 Hz), 7.39-7.36 (m, 2H), 7.27 (d, 1H, J=7.62 Hz), 3.33-3.65 (m, 8H), 2.51 (s, 3H); ESI-MS m/z: calculated for 392.15. found 393.26 [M+H]$^+$.

Example 13

Compound 13 of the present invention was prepared according to Scheme 2. The synthetic method was similar with Example 7, except that the N-(cyclopropanecarbonyl) piperazine was replaced. Firstly, 4-(4-benzyloxycarbonyl-piperidine) carbonyl piperazine (corresponds to A ring with substituent R' of Formula (I) in Compound 13) was prepared, and obtained as white solid. $^1$H NMR (600 MHz, DMSO-d$_6$): δ 11.18 (s, 1H), 7.47-7.46 (d, 1H, J=7.2 Hz), 7.30-7.29 (d, 1H, J=7.8 Hz), 7.21-7.18 (m, 1H), 7.16-7.13 (m, 1H), 6.72-6.70 (m, 1H), 6.59-6.47 (m, 8H), 4.25 (s, 2H), 3.20-3.18 (m, 2H), 2.77-2.54 (m, 8H), 2.10-2.01 (brs, 3H), 0.83-0.80 (m, 2H), 0.64-0.58 (m, 2H); ESI-MS m/z: calculated for 595.2. found 617.9 [M+Na].

Example 14

Compound 14 of the present invention was prepared according to Scheme 1. The synthetic method was similar with Example 1, except that the N-(cyclopropanecarbonyl) piperazine was replaced. Firstly, 4-paranitrophenyl piperazine (corresponds to A ring with substituent R' of Formula (I) in Compound 14) was prepared, and obtained as pale yellow solid. $^1$H NMR (600 MHz, CDCl$_3$): δ 9.52 (s, 1H), 8.41 (d, 1H, J=7.32 Hz), 8.11-8.09 (m, 2H), 8.04 (d, 1H, J=7.08 Hz), 7.84-7.80 (m, 2H), 7.62 (brs, 1H), 7.59 (d, 1H, J=7.68 Hz), 7.49 (t, 1H, J=7.62 Hz), 7.44-7.43 (m, 1H), 6.79-6.78 (m, 2H), 5.40 (s, 2H), 3.94 (brs, 2H), 3.69 (brs, 2H), 3.46 (brs, 4H); ESI-MS m/z: calculated for 485.17. found 508.05 [M+Na].

Example 15

Compound 15 of the present invention was prepared according to Scheme 1. The synthetic method was similar with Example 1, except that the N-(cyclopropanecarbonyl) piperazine was replaced. Firstly, 4-paranitrobenzoyl piperazine (corresponds to A ring with substituent R' of Formula (I) in Compound 15) was prepared, and obtained as pale yellow solid. $^1$H NMR (600 MHz, CDCl$_3$): δ 9.52 (s, 1H), 8.42-8.40 (m, 1H), 8.30-8.29 (m, 2H), 8.04-8.03 (m, 1H), 7.85-7.81 (m, 2H), 7.59-7.57 (m, 4H), 7.48 (brs, 1H), 7.40-7.38 (m, 1H), 5.38 (s, 2H), 3.81-3.46 (m, 8H); ESI-MS m/z: calculated for 513.16. found 536.17 [M+Na]$^+$.

Example 16

Compound 16 of the present invention was prepared according to Scheme 1. The synthetic method was similar with Example 7, except that the N-(cyclopropanecarbonyl) piperazine was replaced. Firstly, 4-benzyl-1,4-diazacycloheptane (corresponds to A ring with substituent R' of Formula (I) in Compound 16) was prepared, and obtained as white solid. $^1$H NMR (600 MHz, CDCl$_3$): δ 9.51 (s, 1H), 8.41-8.39 (m, 1H), 8.04-8.02 (m, 1H), 7.81-7.80 (m, 2H), 7.53-7.49 (m, 2H), 7.45-7.40 (m, 1H), 7.39-7.32 (m, 3H), 7.28-7.27 (m, 2H), 7.24-7.20 (m, 1H), 5.36 (d, 2H, J=13.2 Hz), 3.81-3.79 (m, 2H), 3.67 (brs, 1H), 3.60 (brs, 1H), 3.47-3.45 (m, 2H), 2.83 (brs, 1H), 2.73-2.72 (m, 1H), 2.63-2.58 (m, 2H), 1.99 (brs, 1H), 1.78 (brs, 1H); ESI-MS m/z: calculated for 468.22. found 491.36 [M+Na]$^+$.

Example 17

Compound 17 of the present invention was prepared according to Scheme 1. The synthetic method was similar with Example 1, except that the N-(cyclopropanecarbonyl) piperazine was replaced. Firstly, 4-(3-chloro-(4-trifluoromethyl-phenyl)-4-hydroxypiperidine (corresponds to A ring with substituent R' of Formula (I) in Compound 17) was prepared, and obtained as white solid. $^1$H NMR (600 MHz, CDCl$_3$): δ 11.92 (s, 1H), 8.18 (m, 1H), 8.00 (d, 1H, J=7.26 Hz), 7.96 (brs, 1H), 7.88-7.83 (m, 2H), 7.80 (d, 1H, J=8.28 Hz), 7.65 (d, 1H, J=8.52 Hz), 7.59-7.58 (m, 2H), 7.50-7.47 (m, 1H), 7.45-7.44 (d, 1H, J=7.50 Hz), 5.49 (s, 1H), 5.39 (s, 1H), 4.46 (brs, 1H), 3.46-3.43 (m, 2H), 3.14 (brs, 1H), 2.10-1.94 (m, 2H), 1.68 (brs, 1H), 1.46 (brs, 1H); ESI-MS m/z: calculated for 557.13. found 580.2 [M+Na]$^+$.

Example 18

Compound 18 of the present invention was prepared according to Scheme 1. The synthetic method was similar with Example 1, except that the N-(cyclopropanecarbonyl) piperazine was replaced. Firstly, 4-(4-fluorophenyl)-1,2,3,6-tetrahydropyridine (corresponds to A ring with substituent R' of Formula (I) in Compound 18) was prepared, and obtained as white solid. $^1$H NMR (600 MHz, CDCl$_3$): δ 9.65 (s, 1H), 8.40 (d, 1H, J=9.0 Hz), 8.05 (s, 1H), 7.81-7.79 (m, 2H), 7.602-7.55 (m, 2H), 7.50-7.45 (m, 2H), 7.32-7.30 (m, 2H), 7.02 (d, 2H, J=8.4 Hz), 6.09-5.80 (m, 1H), 5.40 (s, 2H), 4.41 (brs, 1H), 4.11-4.10 (m, 2H), 3.66 (brs, 1H), 2.50-2.37 (m, 2H); ESI-MS m/z: calculated for 455.16. found 478.43 [M+Na]$^+$.

Example 19

Compound 19 of the present invention was prepared according to Scheme 1. The synthetic method was similar with Example 1, except that the N-(cyclopropanecarbonyl) piperazine was replaced. Firstly, 4-(pyrimidin-2-yl) piperazine (corresponds to A ring with substituent R' of Formula (I) in Compound 19) was prepared, and obtained as white solid. $^1$H NMR (600 MHz, CDCl$_3$): δ 9.95 (s, 1H), 8.41 (d, 1H, J=7.68 Hz), 8.30 (d, 2H, J=4.68 Hz), 8.04 (d, 1H, J=7.92 Hz), 7.85-7.83 (m, 1H), 7.82-7.79 (m, 1H), 7.61 (s, 1H), 7.57 (d, 1H, J=7.20 Hz), 7.48 (t, 1H, J=7.56 Hz), 7.42 (d, 1H, J=7.56 Hz), 6.52 (m, 1H), 5.39 (s, 2H), 3.94-3.79 (m, 6H), 3.53 (brs, 2H); ESI-MS m/z: calculated for 442.19. found 465.40 [M+Na]$^+$.

Example 20

Compound 20 of the present invention was prepared according to Scheme 1. The synthetic method was similar with Example 1, except that the N-(cyclopropanecarbonyl) piperazine was replaced. Firstly, 4-tertbutoxycarbonyl-1,4-diazacycloheptane (corresponds to A ring with substituent R' of Formula (I) in Compound 20) was prepared, and obtained as white solid. $^1$H NMR (600 Hz, CDCl$_3$): δ 10.44 (s, 1H), 8.41 (d, 1H, J=6.48 Hz), 8.03 (d, 1H, J=7.50 Hz), 7.83-7.79 (m, 2H), 7.53-7.50 (m, 2H), 7.43 (brs, 1H), 7.34 (brs, 1H), 5.36 (d, 2H, J=9.72 Hz), 3.81 (brs, 1H), 3.71 (brs, 1H), 3.64 (brs, 1H), 3.49-3.35 (m, 5H), 2.02-1.97 (m, 1H), 1.64-1.60 (m, 1H), 1.47 (s, 9H); ESI-MS m/z: calculated for 478.54. found 501.44 [M+Na]$^+$.

Example 21

Compound 21 of the present invention was prepared according to Scheme 1. The synthetic method was similar with Example 1, except that the N-(cyclopropanecarbonyl) piperazine was replaced. Firstly, 4-(3-chloro-phenyl)-4-hydroxypiperidine (corresponds to A ring with substituent R' of Formula (I) in Compound 21) was prepared, and obtained as white solid. $^1$H NMR (600 Hz, CDCl$_3$): δ 9.87 (s, 1H), 8.39-8.38 (m, 1H), 8.05-8.03 (m, 1H), 7.82-7.77 (m, 2H), 7.57 (s, 1H), 7.54 (d, 1H, J=7.50 Hz), 7.47-7.44 (m, 2H), 7.42 (d, 1H, J=7.62 Hz), 7.32 (d, 1H, J=7.62 Hz), 7.28 (t, 1H, J=7.74 Hz), 7.25-7.24 (m, 1H), 5.39 (s, 2H), 4.69 (brs, 1H), 3.68 (m, 1H), 3.58 (m, 1H), 3.32 (brs, 1H), 2.11 (brs, 2H), 1.87 (brs, 2H); ESI-MS m/z: calculated for 489.95. found 512.28[M+Na]$^+$.

Example 22

Compound 22 of the present invention was prepared according to Scheme 1. The synthetic method was similar with Example 1, except that the N-(cyclopropanecarbonyl) piperazine was replaced. Firstly, 4-(4-chloro-phenyl)-4-hydroxypiperidine (corresponds to A ring with substituent R' of Formula (I) in Compound 22) was prepared, and obtained as white solid. $^1$H NMR (600 Hz, CDCl$_3$): δ 9.50 (s, 1H), 8.40-8.38 (m, 1H), 8.05-8.03 (m, 1H), 7.81-7.79 (m, 2H), 7.56 (s, 1H), 7.54 (d, 1H, J=7.50 Hz), 7.46 (t, 1H, J=7.56 Hz), 7.42-7.39 (m, 3H), 7.34-7.32 (m, 2H), 5.39 (s, 2H), 4.70 (brs, 1H), 3.68-3.58 (m, 2H), 3.33 (brs, 1H), 2.14-2.12 (m, 1H), 1.86 (brs, 2H), 1.70 (brs, 1H); ESI-MS m/z: calculated for 489.95. found 512.30 [M+Na]$^+$.

Example 23

Compound 23 of the present invention was prepared according to Scheme 1. The synthetic method was similar with Example 1, except that the N-(cyclopropanecarbonyl) piperazine was replaced. Firstly, 4-phenylpiperazine (corresponds to A ring with substituent R' of Formula (I) in Compound 23) was prepared, and obtained as white solid. $^1$H NMR (600 Hz, CDCl$_3$): δ 9.86 (s, 1H), 8.42-8.40 (m, 1H), 8.06-8.04 (m, 1H), 7.84-7.79 (m, 2H), 7.59 (s, 1H), 7.56 (d, 1H, J=7.56 Hz), 7.47 (t, 1H, J=7.56 Hz), 7.42 (d, 1H, J=7.56 Hz), 7.29-7.28 (m, 2H), 6.92-6.90 (m, 3H), 5.40 (s, 2H), 3.95-3.61 (m, 4H), 3.26-3.13 (m, 4H); ESI-MS m/z: calculated for 440.49. found 463.26 [M+Na]$^+$.

Example 24

Compound 24 of the present invention was prepared according to Scheme 1. The synthetic method was similar with Example 1, except that the N-(cyclopropanecarbonyl) piperazine was replaced. Firstly, 4-phenyl-1,2,3,6-tetrahydropyridine (corresponds to A ring with substituent R' of Formula (I) in Compound 24) was prepared, and obtained as white solid. $^1$H NMR (600 Hz, CDCl$_3$): δ 9.67 (s, 1H), 8.41-8.40 (m, 1H), 8.06-8.05 (m, 1H), 7.82-7.78 (m, 2H), 7.61 (s, 1H), 7.56-7.55 (m, 1H), 7.48-7.43 (m, 2H), 7.36-7.32 (m, 4H), 7.28-7.27 (m, 1H), 6.16-6.15 (m, 1H), 5.40 (s, 2H), 4.41 (brs, 1H), 4.12 (brs, 1H), 4.00 (brs, 1H), 3.64 (brs, 1H), 2.68-2.55 (m, 2H); ESI-MS m/z: calculated for 437.49. found 460.32 [M+Na]$^+$.

Example 25

Compound 25 of the present invention was prepared according to Scheme 2. The synthetic method was similar with Example 7, except that the N-(cyclopropanecarbonyl) piperazine was replaced. Firstly, 4-(4-fluoro-phenyl)-1,2,3,6-tetrahydropyridine (corresponds to A ring with substituent R' of Formula (I) in Compound 25) was prepared, and obtained as white solid. $^1$H NMR (600 MHz, DMSO): $^1$H NMR (600 MHz, DMSO-d$_6$): δ 11.97 (s, 1H), 8.28 (d, 1H, J=7.8 Hz), 8.13 (d, 1H, J=8.4 Hz), 8.03-8.00 (m, 1H), 7.80-7.95 (m, 1H), 7.54 (m, 1H), 7.48 (m, 2H), 7.42-7.40 (m, 2H), 7.33-7.32 (d, 1H, J=7.8 Hz), 7.19-7.16 (d, 2H, J=7.8 Hz), 6.21 (m, 1H), 4.24 (m, 1H), 4.10 (m, 1H), 4.04-4.02 (m, 1H), 3.83 (m, 1H), 3.54 (m, 1H), 1.99 (brs, 1H); ESI-MS m/z: calculated for 441.15. found 442.03 [M+H]$^+$.

Example 26

Compound 26 of the present invention was prepared according to Scheme 2. The synthetic method was similar with Example 7, except that the N-(cyclopropanecarbonyl) piperazine was replaced. Firstly, 4-isonicotinoylpiperazine (corresponds to A ring with substituent R' of Formula (I) in Compound 26) was prepared, and obtained as white solid. $^1$H NMR (600 MHz, DMSO-d$_6$): δ 11.99 (s, 1H), 8.66-8.65 (m, 2H), 8.27-8.26 (m, 1H), 8.10-8.08 (m, 1H), 8.01-7.98 (m, 1H), 7.96-7.94 (m, 1H), 7.53-7.49 (m, 1H), 7.39-7.35 (m, 4H), 7.29-7.25 (m, 1H), 3.73-3.44 (m, 4H), 3.26-3.21 (m, 4H); ESI-MS m/z: calculated for 455.47. found 454.40 [M–H]$^+$.

Example 27

Compound 27 of the present invention was prepared according to Scheme 2. The synthetic method was similar with Example 7, except that the N-(cyclopropanecarbonyl) piperazine was replaced. Firstly, 4-(4-fluorobenzoyl) piperazine (corresponds to A ring with substituent R' of Formula (I) in Compound 27) was prepared, and obtained as white solid. $^1$H NMR (600 MHz, DMSO-d$_6$): δ 11.98 (s, 1H), 8.27 (d, 1H, J=7.2 Hz), 8.10-8.09 (m, 1H), 8.01-7.98 (m, 1H), 7.96-7.93 (m, 1H), 7.53-7.46 (m, 3H), 7.39-7.36 (m, 2H), 7.28-7.25 (m, 3H), 3.63-3.41 (m, 8H); ESI-MS m/z: calculated for 472.47. found 471.28 [M–H]$^+$.

Example 28

Compound 28 of the present invention was prepared according to Scheme 3. The synthetic method was similar with Example 1, except that the N-(cyclopropanecarbonyl) piperazine was replaced. Firstly, 4-(4-nitrobenzoyl)piperazine (corresponds to A ring with substituent R' of Formula (I) in Compound 28) was prepared, and obtained as pale yellow solid. $^1$H NMR (600 MHZ, DMSO-d$_6$): δ 11.89 (s, 1H), 8.27 (brs, 2H), 7.90 (brs, 1H), 7.80 (brs, 1H), 7.67-7.58 (m, 7H), 5.36 (s, 2H), 3.68-3.42 (m, 8H); ESI-MS m/z: calculated for 531.1. found 554.0 [M+Na]$^+$.

Example 29

Compound 29 of the present invention was prepared according to Scheme 3. The synthetic method was similar with Example 1, except that the N-(cyclopropanecarbonyl) piperazine was replaced. Firstly, 4-(4-benzyloxycarbonyl-piperidine)carbonylpiperazine (corresponds to A ring with substituent R' of Formula (I) in Compound 29) was prepared, and obtained as white solid. $^1$H NMR (600 MHZ, DMSO-d$_6$): δ 11.90 (s, 1H), 7.93-7.91 (m, 1H), 7.82-7.80 (m, 1H), 7.67-7.58 (m, 2H), 7.54 (brs, 1H), 7.50-7.48 (m, 1H), 7.40-7.39 (m, 1H), 7.37-7.34 (m, 4H), 7.31-7.28 (m, 1H), 5.36 (s, 2H), 5.06 (s, 2H), 4.00-3.98 (m, 2H), 3.64-3.33 (m, 8H), 2.86 (brs, 3H), 1.61 (brs, 2H), 1.42 (m, 2H); ESI-MS m/z: calculated for 627.2. found 650.0 [M+Na]$^+$.

Example 30

Compound 30 of the present invention was prepared according to Scheme 4. The synthetic method was similar with Example 7, except that the N-(cyclopropanecarbonyl)piperazine was replaced. Firstly, 4-(4-benzyloxycarbonyl-piperidine)carbonylpiperazine (corresponds to A ring with substituent R' of Formula (I) in Compound 30) was prepared, and obtained as white solid. $^1$H NMR (600 MHz, CDCl$_3$): δ 9.90 (s, 1H), 8.43 (d, J=7.80 Hz, 1H), 8.13 (d, J=7.8 Hz, 1H), 7.93-7.91 (m, 2H), 7.89-7.87 (m, 1H), 7.35-7.30 (m, 7H), 7.18-7.15 (m, 1H), 5.12 (s, 2H), 4.22 (brs, 2H), 3.83-3.75 (m, 2H), 3.67-3.56 (m, 4H), 3.50-3.38 (m, 2H), 2.88 (brs, 2H), 2.70-2.63 (m, 1H), 1.80-1.66 (m, 4H); ESI-MS m/z: calculated for 613.23. found 612.41 [M–H]$^+$.

Example 31

Compound 31 of the present invention was prepared according to Scheme 4. The synthetic method was similar with Example 7, except that the N-(cyclopropanecarbonyl)piperazine was replaced. Firstly, 4-(4-nitrobenzoyl)piperazine (corresponds to A ring with substituent R' of Formula (I) in Compound 31) was prepared, and obtained as yellow solid. $^1$H NMR (600 MHz, DMSO-d$_6$) δ 11.97 (s, 1H), 8.27-8.26 (m, 3H), 8.12-8.08 (m, 1H), 8.01-7.98 (m, 1H), 7.96-7.93 (m, 1H), 7.72-7.67 (m, 2H), 7.47-7.34 (m, 3H), 3.76-3.63 (m, 4H), 3.40-3.28 (m, 4H). ESI-MS m/z: calculated for 517.14. found 516.37[M–H]$^+$.

Example 32

Compound 32 of the present invention was prepared according to Scheme 4. The synthetic method was similar with Example 7, except that the N-(cyclopropanecarbonyl)piperazine was replaced. Firstly, 4-(5-methylisoxazole-4-carbonyl)piperazine (corresponds to A ring with substituent R' of Formula (I) in Compound 32) was prepared, and obtained as white solid. $^1$H NMR (600 MHz, CDCl$_3$): δ 9.63 (s, 1H), 8.44 (d, J=7.74 Hz, 1H), 8.14 (d, J=8.04 Hz, 1H), 7.93-7.91 (m, 1H), 7.89-7.87 (m, 1H), 7.33-7.31 (m, 2H), 7.29-7.27 (m, 1H), 7.20-7.17 (m, 1H), 3.95-3.65 (m, 4H), 3.59-3.41 (m, 4H), 1.65 (s, 3H). ESI-MS m/z: calculated for 477.14. found 478.25 [M+H]$^+$.

Example 33

Compound 33 of the present invention was prepared according to Scheme 4. The synthetic method was similar with Example 7, except that the N-(cyclopropanecarbonyl)piperazine was replaced. Firstly, N-phenylpiperazine-1-formamide (corresponds to A ring with substituent R' of Formula (I) in Compound 33) was prepared, and obtained as white solid. $^1$H NMR (600 MHz, DMSO-d$_6$): δ 9.79 (s, 1H), 8.43 (d, J=7.62 Hz, 1H), 8.14 (d, J=7.74 Hz, 1H), 7.93-7.90 (m, 1H), 7.88-7.86 (m, 1H), 7.33-7.27 (m, 6H), 7.18 (t, 1H, J=8.52 Hz), 7.06-7.03 (m, 1H), 6.57 (s, 1H), 3.70-3.57 (m, 5H), 3.54-3.47 (m, 3H); ESI-MS m/z: calculated for 487.2. found 510.1 [M+Na]$^+$.

Example 34

Compound 34 of the present invention was prepared according to Scheme 3. The synthetic method was similar with Example 7, except that the N-(cyclopropanecarbonyl)piperazine was replaced. Firstly, 4-(4-fluorobenzoyl)piperazine (corresponds to A ring with substituent R' of Formula (I) in Compound 34) was prepared, and obtained as white solid. $^1$H NMR (600 MHz, DMSO-d$_6$): δ 12.22 (s, 1H), 8.28-8.26 (m, 1H), 8.05 (d, J=8.04 Hz, 1H), 7.88 (t, 1H, J=7.95 Hz), 7.49-7.48 (m, 2H), 7.36-7.34 (m, 3H), 7.26 (t, 2H, J=8.46 Hz), 3.67-3.39 (m, 8H); ESI-MS m/z: calculated for 524.0. found 523.0 [M–H]$^+$.

Example 35

Compound 35 of the present invention was prepared according to Scheme 3. The synthetic method was similar with Example 7, except that the N-(cyclopropanecarbonyl)piperazine was replaced. Firstly, 4-benzoylpiperazine (corresponds to A ring with substituent R' of Formula (I) in Compound 35) was prepared, and obtained as white solid. $^1$H NMR (600 MHz, DMSO-d$_6$): δ 12.22 (s, 1H), 8.27-8.26 (d, J=7.92 Hz, 1H), 8.05 (d, J=7.38 Hz, 1H), 7.88 (t, 1H, J=7.89 Hz), 7.44-7.34 (m, 8H), 3.66-3.36 (m, 8H); ESI-MS m/z: calculated for 506.0. found 505.1 [M–H]$^+$.

Example 36

Compound 36 of the present invention was prepared according to Scheme 4. The synthetic method was similar with Example 7, except that the N-(cyclopropanecarbonyl)piperazine was replaced. Firstly, 4-(2-methylthiazole-4-carbonyl)piperazine (corresponds to A ring with substituent R' of Formula (I) in Compound 36) was prepared, and obtained as white solid. $^1$H NMR (600 MHz, CDCl$_3$): δ 10.17 (s, 1H), 8.43 (s, 1H), 8.13 (d, J=7.62 Hz, 1H), 7.94-7.83 (m, 3H), 7.33-7.30 (m, 2H), 7.17-7.16 (m, 1H), 4.07-3.83 (m, 6H), 3.51 (brs, 2H), 2.73 (s, 3H); ESI-MS m/z: calculated for 493.12. found 493.95 [M+H]$^+$.

Example 37

Compound 37 of the present invention was prepared according to Scheme 3. The synthetic method was similar with Example 7, except that the N-(cyclopropanecarbonyl)piperazine was replaced. Firstly, 4-(4-fluorophenyl)piperazine (corresponds to A ring with substituent R' of Formula (I) in Compound 37) was prepared, and obtained as pale yellow solid. $^1$H NMR (600 MHz, DMSO-d$_6$): δ 12.31 (s, 1H), 8.32 (d, J=7.92 Hz, 1H), 8.24 (d, J=7.74 Hz, 1H), 8.18 (t, 1H, J=7.95 Hz), 7.50-7.48 (m, 2H), 7.42 (t, 1H, J=8.67 Hz), 7.08-7.05 (m, 2H), 7.00-6.97 (m, 2H), 3.78 (brs, 2H), 3.40-3.39 (m, 2H), 3.16-3.14 (m, 2H), 3.07-3.05 (m, 2H); ESI-MS m/z: calculated for 507.1. found 506.2 [M+H]$^+$.

Example 38

Compound 38 of the present invention was prepared according to Scheme 3. The synthetic method was similar with Example 7, except that the N-(cyclopropanecarbonyl)piperazine was replaced. Firstly, 4-fluorobenzoyl (corresponds to A ring with substituent R' of Formula (I) in Compound 38) was prepared, and obtained as white solid. $^1$H NMR (600 MHz, DMSO-d$_6$): δ 12.30 (s, 1H), 8.32 (d, J=8.04 Hz, 1H), 8.24 (d, J=7.68 Hz, 1H), 8.16 (t, 1H, J=7.92 Hz), 7.50-7.45 (m, 4H), 7.41-7.37 (m, 1H), 7.28-7.25 (m, 2H), 3.67-3.49 (m, 4H), 3.29-3.16 (m, 4H); ESI-MS m/z: calculated for 535.1. found 534.3 [M–H]$^+$.

Example 39

Compound 39 of the present invention was prepared according to Scheme 3. The synthetic method was similar with Example 7, except that the N-(cyclopropanecarbonyl)piperazine was replaced. Firstly, 4-benzoylpiperazine (corresponds to A ring with substituent R' of Formula (I) in Compound 39) was prepared, and obtained as pale yellow solid. $^1$H NMR (600 MHz, DMSO-$d_6$): δ 12.32 (s, 1H), 8.34-8.33 (m, 1H), 8.26 (d, J=7.74 Hz, 1H), 8.18 (t, 1H, J=7.86 Hz), 7.46-7.42 (m, 8H), 3.68-3.42 (m, 8H); ESI-MS m/z: calculated for 517.1. found 516.1 [M−H]$^+$.

Example 40

Compound 40 of the present invention was prepared according to Scheme 3. The synthetic method was similar with Example 7, except that the N-(cyclopropanecarbonyl)piperazine was replaced. Firstly, 4-(1-benzyloxycarbonyl-piperidine)carbonylpiperazine (corresponds to A ring with substituent R' of Formula (I) in Compound 40) was prepared, and obtained as yellow solid. $^1$H NMR (600 MHz, DMSO-$d_6$): δ 12.32 (s, 1H), 8.33 (d, J=7.74 Hz, 1H), 8.24 (d, J=7.74 Hz, 1H), 8.18 (t, 1H, J=7.92 Hz), 7.48-7.47 (m, 2H), 7.42-7.40 (m, 1H), 7.38-7.34 (m, 4H), 7.32-7.30 (m, 1H), 5.07 (s, 2H), 4.01-3.99 (m, 2H), 3.66-3.47 (m, 6H), 3.29-3.24 (m, 2H), 2.90-2.78 (m, 3H), 1.65-1.62 (m, 2H), 1.46-1.40 (m, 2H); ESI-MS m/z: calculated for 658.2. found 657.3 [M−H]$^+$.

Example 41

Compound 41 of the present invention was prepared according to Scheme 3. The synthetic method was similar with Example 7, except that the N-(cyclopropanecarbonyl)piperazine was replaced. Firstly, 4-(4-nitrobenzoyl)piperazine (corresponds to A ring with substituent R' of Formula (I) in Compound 41) was prepared, and obtained as yellow solid. $^1$H NMR (600 MHz, DMSO-$d_6$): 12.29 (s, 1H), 8.34-8.15 (m, 4H), 8.18 (s, 1H), 7.71 (brs, 2H), 7.49-7.39 (m, 3H), 3.76-3.65 (m, 4H), 3.44-3.36 (m, 2H), 3.31-3.25 (m, 2H); ESI-MS m/z: calculated for 562.1. found 561.1 [M−H]$^+$.

Example 42

Compound 42 of the present invention was prepared according to Scheme 4. The synthetic method was similar with Example 7, except that the N-(cyclopropanecarbonyl)piperazine was replaced. Firstly, N-cyclohexyl piperazine-1-formamide (corresponds to A ring with substituent R' of Formula (I) in Compound 42) was prepared, and obtained as white solid. $^1$H NMR (600 MHz, DMSO-$d_6$): δ 9.27 (s, 1H), 8.44 (d, J=7.6 Hz, 1H), 8.14 (d, J=7.4 Hz, 1H), 7.90 (m, 2H), 7.30 (m, 2H), 7.17 (m, 1H), 5.35 (s, 1H), 4.29 (m, 1H), 3.33 (m, 8H), 1.98 (m, 4H), 1.69 (s, 3H), 1.59 (s, 3H); ESI-MS m/z: calculated for 493.5. found 516.1 [M+Na]$^+$.

Example 43

Compound 43 of the present invention was prepared according to Scheme 4. The synthetic method was similar with Example 7, except that the N-(cyclopropanecarbonyl)piperazine was replaced. Firstly, 4-acetylpiperazine (corresponds to A ring with substituent R' of Formula (I) in Compound 43) was prepared, and obtained as white solid. $^1$H NMR (600 MHz, DMSO-$d_6$): δ 9.71 (s, 1H), 8.44 (d, 1H, J=7.74 Hz), 8.13 (d, 1H, J=7.80 Hz), 7.93-7.91 (m, 1H), 7.89-7.87 (m, 1H), 7.33-7.31 (m, 2H), 7.19-7.16 (m, 1H), 3.82-3.65 (m, 4H), 3.57-3.41 (m, 4H), 2.16 (s, 3H); ESI-MS m/z: calculated for 410.1. found 433.1 [M+Na]$^+$.

Example 44

Compound 44 of the present invention was prepared according to Scheme 4. The synthetic method was similar with Example 7, except that the N-(cyclopropanecarbonyl)piperazine was replaced. Firstly, 4-(thiazole-4-carbonyl)piperazine (corresponds to A ring with substituent R' of Formula (I) in Compound 44) was prepared, and obtained as white solid. $^1$H NMR (600 MHz, CDCl$_3$): δ 9.57 (s, 1H), 8.81-8.79 (m, 1H), 8.44 (d, J=7.68 Hz, 1H), 8.14 (d, J=7.92 Hz, 1H), 8.09 (brs, 1H), 7.93-7.91 (m, 1H), 7.89-7.86 (m, 1H), 7.35-7.31 (m, 2H), 7.18 (brs, 1H), 4.08-4.03 (m, 2H), 3.91-3.83 (m, 4H), 3.52 (brs, 2H); ESI-MS m/z: calculated for 479.11. found 480.24 [M+H]$^+$.

Example 45

Compound 45 of the present invention was prepared according to Scheme 4. The synthetic method was similar with Example 7, except that the N-(cyclopropanecarbonyl)piperazine was replaced. Firstly, 4-(2-benzyloxycarbonyl-piperidine)carbonylpiperazine (corresponds to A ring with substituent R' of Formula (I) in Compound 45) was prepared, and obtained as white solid. $^1$H NMR (600 MHz, CDCl$_3$): δ 9.50 (s, 1H), 8.44 (d, J=7.86 Hz, 1H), 8.15-8.13 (m, 1H), 7.93-7.91 (m, 1H), 7.89-7.87 (m, 1H), 7.36-7.31 (m, 7H), 7.20-7.18 (m, 1H), 5.15 (s, 2H), 4.22-4.14 (m, 2H), 3.95-3.39 (m, 9H), 2.99-2.77 (m, 2H), 1.91-1.87 (m, 1H), 1.77-1.74 (m, 2H), 1.52-1.42 (m, 1H); ESI-MS m/z: calculated for 613.13. found 636.29 [M+Na]$^+$.

Example 46

Compound 46 of the present invention was prepared according to Scheme 4. The synthetic method was similar with Example 7, except that the N-(cyclopropanecarbonyl)piperazine was replaced. Firstly, 4-(3-benzyloxycarbonyl-piperidine)carbonylpiperazine (corresponds to A ring with substituent R' of Formula (I) in Compound 46) was prepared, and obtained as white solid. $^1$H NMR (600 MHz, CDCl$_3$): δ 10.72 (s, 1H), 8.42 (d, J=7.26 Hz, 1H), 8.12 (d, J=7.44 Hz, 1H), 7.91-7.87 (m, 1H), 7.87-7.84 (m, 1H), 7.30 (brs, 6H), 7.16-7.14 (m, 2H), 5.10 (s, 2H), 3.99-3.65 (m, 4H), 3.50-3.33 (m, 6H), 1.96 (brs, 1H), 1.88-1.63 (m, 5H), 1.42 (brs, 1H); ESI-MS m/z: calculated for 613.13. found 636.48 [M+Na]$^+$.

Example 47

Compound 47 of the present invention was prepared according to Scheme 4. The synthetic method was similar with Example 7, except that the N-(cyclopropanecarbonyl)piperazine was replaced. Firstly, 4-(4-oxocyclohexanecarbonyl)piperazine (corresponds to A ring with substituent R' of Formula (I) in Compound 47) was prepared, and obtained as white solid. $^1$H NMR (600 MHz, CDCl$_3$): δ 10.50 (s, 1H), 8.42 (d, J=7.74 Hz, 1H), 8.12 (d, J=7.86 Hz, 1H), 7.92-7.90 (m, 1H), 7.88-7.85 (m, 1H), 7.32-7.31 (m, 2H), 7.18-7.15 (m, 1H), 3.84-3.62 (m, 6H), 3.50-3.43 (m, 2H), 2.97-2.86 (m, 1H), 2.53 (brs, 2H), 2.37-2.25 (m, 2H), 2.04 (brs, 4H); ESI-MS m/z: calculated for 492.18. found 493.28 [M+H]$^+$.

Example 48

Compound 48 of the present invention was prepared according to Scheme 4. The synthetic method was similar with Example 7, except that the N-(cyclopropanecarbonyl)piperazine was replaced. Firstly, 4-(4-cyanobenzoyl)piperazine (corresponds to A ring with substituent R' of Formula (I) in Compound 48) was prepared, and obtained as white solid. $^1$H NMR (600 MHz, DMSO-$d_6$): δ 11.98 (s, 1H), 8.28 (d, 1H, J=7.80 Hz), 8.12 (brs, 1H), 8.03-8.00 (m, 1H), 7.97-7.94 (m, 3H), 7.62 (brs, 2H), 7.49-7.36 (m, 3H), 3.76-3.65 (m, 4H), 3.44-3.37 (m, 4H); ESI-MS m/z: calculated for 497.15. found 520.12 [M+Na]$^+$.

Example 49

Compound 49 of the present invention was prepared according to Scheme 4. The synthetic method was similar with Example 7, except that the N-(cyclopropanecarbonyl) piperazine was replaced. Firstly, (R)4-(2-phenylpropionyl) piperazine (corresponds to A ring with substituent R' of Formula (I) in Compound 49) was prepared, and obtained as white solid. $^1$H NMR (600 MHz, CDCl$_3$): δ 10.73 (s, 1H), 8.41 (d, J=7.74 Hz, 1H), 8.10-8.09 (m, 1H), 7.90-7.88 (m, 1H), 7.86-7.84 (m, 1H), 7.31-7.27 (m, 3H), 7.23-7.20 (m, 4H), 7.13-7.08 (m, 1H), 3.98-3.76 (m, 3H), 3.48-3.40 (m, 4H), 3.22 (brs, 1H), 2.92-2.74 (m, 1H), 1.45-1.44 (m, 3H); ESI-MS m/z: calculated for 500.19. found 523.03 [M+Na]$^+$.

Example 50

Compound 50 of the present invention was prepared according to Scheme 4. The synthetic method was similar with Example 7, except that the N-(cyclopropanecarbonyl) piperazine was replaced. Firstly, 4-(cyclopropanecarbonyl) piperazine (corresponds to A ring with substituent R' of Formula (I) in Compound 50) was prepared, and obtained as white solid. $^1$H NMR (600 MHz, DMSO-d$_6$): δ 10.43 (s, 1H), 8.43 (d, J=7.86 Hz, 1H), 8.13 (d, J=7.86 Hz, 1H), 7.92-7.90 (m, 1H), 7.88-7.85 (m, 1H), 7.32-7.30 (m, 2H), 7.16 (t, 1H, J=8.67 Hz), 3.85-3.68 (m, 6H), 3.49-3.42 (m, 2H), 1.76-1.69 (m, 1H), 1.01 (brs, 2H), 0.81-0.75 (m, 2H); ESI-MS m/z: calculated for 436.1. found 459.1 [M+Na]$^+$.

Example 51

Compound 51 of the present invention was prepared according to Scheme 4. The synthetic method was similar with Example 7, except that the N-(cyclopropanecarbonyl) piperazine was replaced. Firstly, 1-(piperazine-1-yl)propane-1,2-dione (corresponds to A ring with substituent R' of Formula (I) in Compound 51) was prepared, and obtained as white solid. $^1$H NMR (600 MHz, CDCl$_3$): δ 9.97 (s, 1H), 8.44 (d, J=7.62 Hz, 1H), 8.13 (d, J=7.74 Hz, 1H), 7.93-7.91 (m, 1H), 7.89-7.87 (m, 1H), 7.33-7.32 (m, 2H), 7.20-7.15 (m, 1H), 3.86 (brs, 2H), 3.74 (brs, 1H), 3.68 (brs, 1H), 3.62 (brs, 1H), 3.57 (brs, 1H), 3.49 (brs, 2H), 1.66 (s, 3H); SI-MS m/z: calculated for 438.13. found 460.91 [M+Na]$^+$.

Example 52

Compound 52 of the present invention was prepared according to Scheme 4. The synthetic method was similar with Example 7, except that the N-(cyclopropanecarbonyl) piperazine was replaced. Firstly, 4-(5-methylisoxazole-3-carbonyl)piperazine (corresponds to A ring with substituent R' of Formula (I) in Compound 52) was prepared, and obtained as white solid. $^1$H NMR (600 MHz, CDCl$_3$): δ 9.51 (s, 1H), 8.44 (d, J=7.62 Hz, 1H), 8.14 (d, J=6.90 Hz, 1H), 7.93-7.91 (m, 1H), 7.89-7.87 (m, 1H), 7.34-7.30 (m, 2H), 7.21-7.15 (m, 1H), 6.33 (d, J=4.86 Hz, 1H), 4.01-3.82 (m, 6H), 3.51 (brs, 2H), 2.48 (s, 3H); ESI-MS m/z: calculated for 477.14. found 475.82 [M−H]$^+$.

Example 53

Compound 53 of the present invention was prepared according to Scheme 4. The synthetic method was similar with Example 7, except that the N-(cyclopropanecarbonyl) piperazine was replaced. Firstly, 4-(2,2,2-trifluoroacetyl)piperazine (corresponds to A ring with substituent R' of Formula (I) in Compound 53) was prepared, and obtained as white solid. $^1$H NMR (600 MHz, CDCl$_3$): δ 10.70 (s, 1H), 8.42 (d, 1H, J=7.80 Hz), 8.13 (d, 1H, J=7.80 Hz), 7.90-7.93 (m, 1H), 7.88-7.86 (m, 1H), 7.34-7.33 (m, 2H), 7.19-7.17 (m, 1H), 3.87-3.66 (m, 6H), 3.52 (brs, 2H); ESI-MS m/z: calculated for 464.11. found 486.93 [M+Na]$^+$.

Example 54

Compound 54 of the present invention was prepared according to Scheme 4. The synthetic method was similar with Example 7, except that the N-(cyclopropanecarbonyl) piperazine was replaced. Firstly, 4-(3,3,3-trifluoropropionyl) piperazine (corresponds to A ring with substituent R' of Formula (I) in Compound 54) was prepared, and obtained as white solid. $^1$H NMR (600 MHz, CDCl$_3$): δ 10.18 (s, 1H), 8.43 (d, 1H, J=7.62 Hz), 8.13 (d, 1H, J=7.62 Hz), 7.93-7.87 (m, 2H), 7.33-7.32 (m, 2H), 7.19-7.16 (m, 1H), 3.85-3.71 (m, 4H), 3.59-3.45 (m, 4H), 3.33-3.23 (m, 2H); ESI-MS m/z: calculated for 478.13. found 500.96 [M+Na]$^+$.

Example 55

Compound 55 of the present invention was prepared according to Scheme 4. The synthetic method was similar with Example 7, except that the N-(cyclopropanecarbonyl) piperazine was replaced. Firstly, 4-pivaloylpiperazine (corresponds to A ring with substituent R' of Formula (I) in Compound 55) was prepared, and obtained as white solid. $^1$H NMR (600 MHz, CDCl$_3$): δ 10.01 (s, 1H), 8.43 (d, J=7.86 Hz, 1H), 8.13 (d, J=7.74 Hz, 1H), 7.93-7.90 (m, 1H), 7.89-7.86 (m, 1H), 7.32-7.28 (m, 2H), 7.18-7.14 (m, 1H), 3.79-3.75 (m, 4H), 3.68-3.67 (m, 2H), 3.42 (brs, 2H), 1.29 (s, 9H); ESI-MS m/z: calculated for 452.19. found 475.05 [M+Na]$^+$.

Example 56

Compound 56 of the present invention was prepared according to Scheme 4. The synthetic method was similar with Example 7, except that the N-(cyclopropanecarbonyl) piperazine was replaced. Firstly, 4-(2-methoxyacetyl)piperazine (corresponds to A ring with substituent R' of Formula (I) in Compound 56) was prepared, and obtained as white solid. $^1$H NMR (600 MHz, CDCl$_3$): δ 9.85 (s, 1H), 8.44 (d, J=7.62 Hz, 1H), 8.13 (d, J=7.86 Hz, 1H), 7.93-7.92 (m, 1H), 7.89-7.92 (m, 1H), 7.32-7.31 (m, 2H), 7.18-7.16 (m, 1H), 4.12 (d, 2H, J=26.4 Hz), 3.81-3.57 (m, 6H), 3.44-3.40 (m, 5H); ESI-MS m/z: calculated for 440.15. found 462.85 [M+Na]$^+$.

Example 57

Compound 57 of the present invention was prepared according to Scheme 4. The synthetic method was similar with Example 7, except that the N-(cyclopropanecarbonyl) piperazine was replaced. Firstly, 4-(2-methylthiazole-4-carbonyl)piperazine (corresponds to A ring with substituent R' of Formula (I) in Compound 57) was prepared, and obtained as white solid. $^1$H NMR (600 MHz, CDCl$_3$): δ 9.61 (s, 1H), 8.44 (d, J=7.20 Hz, 1H), 8.14 (brs, 1H), 7.93-7.90 (m, 1H), 7.89-7.87 (m, 1H), 7.76-7.67 (m, 2H), 7.57-7.48 (m, 2H), 7.33-7.31 (m, 2H), 7.22-7.11 (m, 1H), 3.96-3.88 (m, 4H), 3.58-3.36 (m, 4H); ESI-MS m/z: calculated for 497.15. found 520.00 [M+Na]$^+$.

Example 58

Compound 58 of the present invention was prepared according to Scheme 4. The synthetic method was similar with Example 7, except that the N-(cyclopropanecarbonyl) piperazine was replaced. Firstly, N-isopropylpiperazine-1-formamide (corresponds to A ring with substituent R' of Formula (I) in Compound 58) was prepared, and obtained as white solid. $^1$H NMR (600 MHz, DMSO-$d_6$): δ 11.96 (s, 1H), 8.26 (d, J=7.80 Hz, 1H), 8.10 (d, J=7.80 Hz, 1H), 8.01-7.99 (m, 1H), 7.96-7.93 (m, 1H), 7.45-7.43 (m, 1H), 7.41-7.36 (m, 2H), 6.22 (d, J=7.38 Hz, 1H), 3.75-3.70 (m, 1H), 3.58 (brs, 2H), 3.52-3.34 (m, 2H), 3.28-3.26 (m, 2H), 3.214-3.207 (m, 2H), 1.03 (d, J=6.54 Hz, 6H); ESI-MS m/z: calculated for 453.18. found 476.12 [M+Na]$^+$.

Example 59

Compound 59 of the present invention was prepared according to Scheme 4. The synthetic method was similar with Example 7, except that the N-(cyclopropanecarbonyl) piperazine was replaced. Firstly, 4-(2-ethoxyacetyl)piperazine (corresponds to A ring with substituent R' of Formula (I) in Compound 59) was prepared, and obtained as white solid. $^1$H NMR (600 MHz, CDCl$_3$) δ 10.38 (s, 1H), 8.43 (d, J=7.74 Hz, 1H), 8.12 (d, J=7.92 Hz, 1H), 7.92-7.89 (m, 1H), 7.88-7.85 (m, 1H), 7.32-7.30 (m, 2H), 7.17-7.14 (m, 1H), 4.17-4.13 (m, 2H), 3.81 (brs, 2H), 3.71-3.53 (m, 6H), 3.48-3.39 (brs, 2H), 1.24-1.19 (m, 3H). ESI-MS m/z: calculated for 454.17. found 453.18[M−H]$^+$.

Example 60

Compound 60 of the present invention was prepared according to Scheme 4. The synthetic method was similar with Example 7, except that the N-(cyclopropanecarbonyl) piperazine was replaced. Firstly, 4-isonicotinoylpiperazine (corresponds to A ring with substituent R' of Formula (I) in Compound 60) was prepared, and obtained as white solid. $^1$H NMR (600 MHz, DMSO-$d_6$): δ 9.25 (s, 1H), 8.77-8.71 (m, 2H), 8.45 (d, J=6.5 Hz, 1H), 8.14-8.13 (m, 1H), 7.94-7.92 (m, 1H), 7.90-7.88 (m, 1H), 7.35-7.30 (m, 4H), 7.21-7.11 (m, 1H), 3.93-3.75 (m, 4H), 3.56-3.39 (m, 4H); ESI-MS m/z: calculated for 473.1. found 474.02 [M+H]$^+$.

Example 61

Compound 61 of the present invention was prepared according to Scheme 4. The synthetic method was similar with Example 7, except that the N-(cyclopropanecarbonyl) piperazine was replaced. Firstly, 4-(2-ethylbutyryl)piperazine (corresponds to A ring with substituent R' of Formula (I) in Compound 61) was prepared, and obtained as white solid. $^1$H NMR (600 MHz, CDCl$_3$) δ 9.45 (s, 1H), 8.44 (d, J=7.98 Hz, 1H), 8.14 (d, J=7.68 Hz, 1H), 7.94-7.91 (m, 1H), 7.90-7.87 (m, 1H), 7.33-7.31 (m, 2H), 7.19-7.17 (m, 1H), 3.80-3.60 (m, 6H), 3.44-3.41 (m, 2H), 2.55-2.45 (m, 1H), 1.70-1.67 (m, 2H), 1.51-1.50 (m, 2H), 0.90-0.87 (m, 6H). ESI-MS m/z: calculated for 466.20. found 465.23[M−H]$^+$.

Example 62

Compound 62 of the present invention was prepared according to Scheme 4. The synthetic method was similar with Example 7, except that the N-(cyclopropanecarbonyl) piperazine was replaced. Firstly, 4-(4,4-difluoropiperidine-1-carbonyl)piperazine (corresponds to A ring with substituent R' of Formula (I) in Compound 62) was prepared, and obtained as white solid. $^1$H NMR (600 MHz, CDCl$_3$): δ 10.61 (s, 1H), 8.41 (d, J=7.74 Hz, 1H), 8.11 (d, J=7.80 Hz, 1H), 7.91-7.88 (m, 1H), 7.86-7.84 (m, 1H), 7.29-7.28 (m, 2H), 7.15-7.10 (m, 1H), 3.84-3.74 (m, 2H), 3.43 (brs, 2H), 3.38-3.35 (m, 6H), 3.30 (brs, 2H), 1.99-1.94 (m, 4H); ESI-MS m/z: calculated for 515.1. found 537.95 [M+Na]$^+$.

Example 63

Compound 63 of the present invention was prepared according to Scheme 4. The synthetic method was similar with Example 7, except that the N-(cyclopropanecarbonyl) piperazine was replaced. Firstly, 4-(thiophene-2-carbonyl) piperazine (corresponds to A ring with substituent R' of Formula (I) in Compound 63) was prepared, and obtained as white solid. $^1$H NMR (600 MHz, CDCl$_3$): δ 9.58 (s, 1H), 8.44 (d, J=7.92 Hz, 1H), 8.13 (d, J=7.74 Hz, 1H), 7.93-7.91 (m, 1H), 7.89-7.87 (m, 1H), 7.49-7.48 (m, 1H), 7.34-7.31 (m, 3H), 7.18 (t, 1H, J=8.70 Hz), 7.07-7.06 (m, 1H), 3.87 (brs, 3H), 3.80-3.79 (m, 3H), 3.50 (brs, 2H); ESI-MS m/z: calculated for 478.1. found 477.2[M−H].

Example 64

Compound 64 of the present invention was prepared according to Scheme 4. The synthetic method was similar with Example 7, except that the N-(cyclopropanecarbonyl) piperazine was replaced. Firstly, 4-(3-hydroxypropyl)piperazine (corresponds to A ring with substituent R' of Formula (I) in Compound 64) was prepared, and obtained as white solid. $^1$H NMR (600 MHz, CDCl$_3$): δ 9.50 (s, 1H), 8.44 (d, J=7.74 Hz, 1H), 8.14 (d, J=7.62 Hz, 1H), 7.93-7.91 (m, 1H), 7.89-7.87 (m, 1H), 7.30-7.29 (m, 2H), 7.17-7.14 (m, 1H), 3.82 (t, 2H, J=5.22 Hz), 3.45 (brs, 2H), 2.69-2.66 (m, 6H), 2.56 (brs, 2H), 1.78-1.75 (m, 2H); ESI-MS m/z: calculated for 426.1. found 427.0 [M+H]$^+$.

Example 65

Compound 65 of the present invention was prepared according to Scheme 4. The synthetic method was similar with Example 7, except that the N-(cyclopropanecarbonyl) piperazine was replaced. Firstly, 4-formonitrile piperidine (corresponds to A ring with substituent R' of Formula (I) in Compound 65) was prepared, and obtained as white solid. $^1$H NMR (600 MHz, CDCl$_3$): δ 9.28 (s, 1H), 8.45 (d, J=7.68 Hz, 1H), 8.14 (d, J=7.92 Hz, 1H), 7.93-7.91 (m, 1H), 7.90-7.87 (m, 1H), 7.32-7.30 (m, 2H), 7.19-7.16 (m, 1H), 3.94-3.82 (m, 2H), 3.59 (brs, 1H), 3.40 (brs, 1H), 2.95 (brs, 1H), 2.06-1.88 (m, 4H); ESI-MS calculated for 393.1. found 394.1 [M+H]$^+$.

Example 66

Compound 66 of the present invention was prepared according to Scheme 4. The synthetic method was similar with Example 7, except that the N-(cyclopropanecarbonyl) piperazine was replaced. Firstly, 4-isobutyrylpiperazine (corresponds to A ring with substituent R' of Formula (I) in Compound 66) was prepared, and obtained as white solid. $^1$H NMR (600 MHz, CDCl$_3$): δ 10.15 (s, 1H), 8.43 (d, J=7.74 Hz, 1H), 8.13 (d, J=7.92 Hz, 1H), 7.93-7.90 (m, 1H), 7.89-7.86 (m, 1H), 7.32-7.31 (m, 2H), 7.18-7.15 (m, 1H), 3.81-3.56 (m, 6H), 3.46-3.41 (m, 2H), 2.82-2.74 (m, 1H), 1.14-1.13 (m, 6H); ESI-MS m/z: calculated for 438.1. found 461.07 [M+Na].

Example 67

Compound 67 of the present invention was prepared according to Scheme 4. The synthetic method was similar with Example 7, except that the N-(cyclopropanecarbonyl) piperazine was replaced. Firstly, N,N-dimethylpiperazine-1-formamide (corresponds to A ring with substituent R' of Formula (I) in Compound 67) was prepared, and obtained as white solid. $^1$H NMR (600 MHz, CDCl$_3$): δ 9.87 (s, 1H), 8.44 (d, J=7.80 Hz, 1H), 8.13 (d, J=7.74 Hz, 1H), 7.92-7.90 (m, 1H), 7.88-7.86 (m, 1H), 7.31-7.28 (m, 2H), 7.17-7.14 (m, 1H), 3.80 (brs, 2H), 3.43 (brs, 2H), 3.33-3.31 (m, 2H), 3.26 (m, 2H), 2.85 (s, 6H); ESI-MS m/z: calculated for 439.1. found 439.95 [M+H]$^+$.

Example 68

Compound 68 of the present invention was prepared according to Scheme 4. The synthetic method was similar with Example 7, except that the N-(cyclopropanecarbonyl) piperazine was replaced. Firstly, 4-(3-trifluoromethyl-4-methyl-benzoyl)piperazine (corresponds to A ring with substituent R' of Formula (I) in Compound 68) was prepared, and obtained as white solid. $^1$H NMR (600 MHz, CDCl$_3$): δ 9.60 (s, 1H), 8.44 (d, J=7.86 Hz, 1H), 8.13 (d, J=7.62 Hz, 1H), 7.93-7.91 (m, 1H), 7.89-7.87 (m, 1H), 7.69 (s, 1H), 7.48 (d, J=7.56 Hz, 1H), 7.37-7.35 (m, 1H), 7.32-7.30 (m, 2H), 7.17 (brs, 1H), 3.81-3.48 (m, 8H), 2.52 (s, 3H); ESI-MS m/z: calculated for 554.1. found 576.98 [M+Na]$^+$.

Example 69

Compound 69 of the present invention was prepared according to Scheme 4. The synthetic method was similar with Example 7, except that the N-(cyclopropanecarbonyl) piperazine was replaced. Firstly, 4-acryloylpiperazine (corresponds to A ring with substituent R' of Formula (I) in Compound 69) was prepared as white solid. $^1$H NMR (600 MHz, CDCl$_3$): δ 10.25 (s, 1H), 8.43 (d, J=7.80 Hz, 1H), 8.13 (d, J=7.98 Hz, 1H), 7.93-7.90 (m, 1H), 7.89-7.86 (m, 1H), 7.33-7.31 (m, 2H), 7.18-7.15 (m, 1H), 6.56 (brs, 1H), 6.32 (d, 1H, J=16.86 Hz), 5.75 (brs, 1H), 3.81-3.62 (m, 6H), 3.46 (brs, 2H); ESI-MS m/z: calculated for 422.1. found 444.97 [M+Na]$^+$.

Example 70

Compound 70 of the present invention was prepared according to Scheme 70. The synthetic method was similar with Example 7, except that the N-(cyclopropanecarbonyl) piperazine was replaced. Firstly, 4-(2-hydroxypropionyl)piperazine (corresponds to A ring with substituent R' of Formula (I) in Compound 70) was prepared, and obtained as white solid. $^1$H NMR (600 MHz, CDCl$_3$): δ 10.09 (s, 1H), 8.43 (d, J=7.68 Hz, 1H), 8.13 (d, J=7.62 Hz, 1H), 7.92-7.90 (m, 1H), 7.88-7.86 (m, 1H), 7.31 (brs, 2H), 7.17 (t, 1H, J=8.58 Hz), 5.48-5.43 (m, 1H), 4.36-3.35 (m, 1H), 3.96-3.78 (m, 2H), 3.66-3.44 (m, 6H), 1.60-1.57 (m, 3H); ESI-MS m/z: calculated for 440.0. found 439.0 [M−H].

Example 71

Compound 71 of the present invention was prepared according to Scheme 4. The synthetic method was similar with Example 7, except that the N-(cyclopropanecarbonyl) piperazine was replaced. Firstly, 4-(4,4-difluoropiperidine-1-carbonyl)piperidine (corresponds to A ring with substituent R' of Formula (I) in Compound 71) was prepared, and obtained as white solid. $^1$H NMR (600 MHz, CDCl$_3$): δ 9.40 (s, 1H), 8.44 (d, J=7.74 Hz, 1H), 8.14 (d, J=7.98 Hz, 1H), 7.94-7.91 (m, 1H), 7.89-7.86 (m, 1H), 7.32-7.28 (m, 2H), 7.16 (t, 1H, J=8.7 Hz), 4.72-4.70 (m, 1H), 3.74 (brs, 3H), 3.62 (brs, 2H), 3.17 (brs, 1H), 2.97 (brs, 1H), 2.80 (brs, 1H), 2.00 (m, 4H), 1.84 (brs, 3H), 1.71-1.69 (m, 1H); ESI-MS m/z: calculated for 514.1. found 515.1 [M+H]$^+$.

Example 72

Compound 72 of the present invention was prepared according to Scheme 4. The synthetic method was similar with Example 7, except that the N-(cyclopropanecarbonyl) piperazine was replaced. Firstly, 4-(piperidine-1-carbonyl)piperidine, (corresponds to A ring with substituent R' of Formula (I) in Compound 72) was prepared, and obtained as white solid. $^1$H NMR (600 MHz, CDCl$_3$): δ 9.51 (s, 1H), 8.44 (d, J=7.80 Hz, 1H), 8.14 (d, J=7.98 Hz, 1H), 7.93-7.90 (m, 1H), 7.88-7.86 (m, 1H), 7.32-7.28 (m, 2H), 7.15 (t, 1H, J=8.70 Hz), 4.71-4.69 (m, 1H), 3.75-3.72 (m, 1H), 3.55 (brs, 2H), 3.45 (brs, 2H), 3.15 (brs, 1H), 2.97-2.93 (m, 1H), 2.78 (brs, 1H), 1.83 (brs, 2H), 1.70-1.66 (m, 4H), 1.58-1.54 (m, 4H); ESI-MS m/z: calculated for 478.2. found 501.1 [M+Na]$^+$.

Example 73

Compound 73 of the present invention was prepared according to Scheme 4. The synthetic method was similar with Example 7, except that the N-(cyclopropanecarbonyl) piperazine was replaced. Firstly, N-phenylpiperidine-4-formamide (corresponds to A ring with substituent R' of Formula (I) in Compound 73) was prepared, and obtained as white solid. $^1$H NMR (600 MHz, CDCl$_3$): δ 9.82 (s, 1H), 8.43 (d, J=7.86 Hz, 1H), 8.13 (d, J=7.86 Hz, 1H), 7.92-7.90 (m, 1H), 7.87-7.85 (m, 1H), 7.54 (s, 1H), 7.51 (d, 2H, J=7.38 Hz), 7.31-7.29 (m, 3H), 7.15 (t, 1H, J=8.70 Hz), 7.10 (t, 1H, J=7.23 Hz), 4.74-4.72 (m, 1H), 3.78-3.76 (m, 1H), 3.16 (brs, 1H), 2.97-2.93 (m, 1H), 2.56-2.51 (m, 1H), 2.05-2.03 (m, 1H), 1.95-1.84 (m, 3H); ESI-MS m/z: calculated for 486.1. found 485.1 [M−H]$^+$.

Example 74

Compound 74 of the present invention was prepared according to Scheme 4. The synthetic method was similar with Example 7, except that the N-(cyclopropanecarbonyl) piperazine was replaced. Firstly, N-ethylpiperidine-4-formamide (corresponds to A ring with substituent R' of Formula (I) in Compound 74) was prepared, and obtained as white solid. $^1$H NMR (600 MHz, CDCl$_3$): δ 9.60 (s, 1H), 8.44 (d, J=7.86 Hz, 1H), 8.13 (d, J=7.86 Hz, 1H), 7.92-7.90 (m, 1H), 7.88-7.86 (m, 1H), 7.29-7.28 (m, 2H), 7.15 (t, 1H, J=8.70 Hz), 5.54 (brs, 1H), 4.72-4.70 (m, 1H), 3.74-3.72 (m, 1H), 3.31-3.27 (m, 2H), 3.12 (brs, 1H), 2.92-2.88 (m, 1H), 2.34-2.31 (m, 1H), 1.96-1.94 (m, 1H), 1.85-1.83 (m, 1H), 1.77-1.76 (m, 2H), 1.13 (t, J=7.23 Hz, 3H); ESI-MS m/z: calculated for 438.1. found 461.1 [M+Na]$^+$.

Example 75

Compound 75 of the present invention was prepared according to Scheme 4. The synthetic method was similar with Example 7, except that the N-(cyclopropanecarbonyl) piperazine was replaced. Firstly, 4-(4-(dimethylamino)benzoyl)piperazine (corresponds to A ring with substituent R' of Formula (I) in Compound 75) was prepared, and obtained as white solid. $^1$H NMR (600 MHz, CDCl$_3$): δ 9.50 (s, 1H), 8.44 (d, J=7.68 Hz, 1H), 8.13 (d, J=7.62 Hz, 1H), 7.93-7.91 (m, 1H), 7.89-7.86 (m, 1H), 7.37 (d, J=8.76 Hz, 2H), 7.33-7.29 (m, 2H), 7.17 (t, 1H, J=8.61 Hz), 6.68 (d, J=8.64 Hz, 2H), 3.82-3.69 (m, 6H), 3.45 (brs, 2H), 3.01 (s, 6H); ESI-MS m/z: calculated for 515.1. found 538.1 [M+Na]$^+$.

Example 76

Compound 76 of the present invention was prepared according to Scheme 4. The synthetic method was similar with Example 7, except that the N-(cyclopropanecarbonyl) piperazine was replaced. Firstly, 4-(3-(dimethylamino)benzoyl)piperazine (corresponds to A ring with substituent R' of Formula (I) in Compound 76) was prepared, and obtained as white solid. $^1$H NMR (600 MHz, CDCl$_3$): δ 9.39 (s, 1H), 8.44 (d, J=7.62 Hz, 1H), 8.13 (d, J=7.68 Hz, 1H), 7.93-7.91 (m, 1H), 7.89-7.87 (m, 1H), 7.36-7.29 (m, 3H), 7.18 (brs, 1H), 6.76-6.76 (m, 2H), 6.70-6.69 (m, 1H), 3.79 (brs, 4H), 3.49 (brs, 4H), 2.98 (s, 6H); ESI-MS m/z: calculated for 515.1. found 538.1 [M+Na]$^+$.

Example 77

Compound 77 of the present invention was prepared according to Scheme 4. The synthetic method was similar with Example 7, except that the N-(cyclopropanecarbonyl) piperazine was replaced. Firstly, 4-tertbutylpiperazine (corresponds to A ring with substituent R' of Formula (I) in Compound 77) was prepared, and obtained as white solid. $^1$H NMR (600 MHz, CDCl$_3$): δ 8.53-8.48 (m, 1H), 8.13-8.12 (m, 1H), 8.08 (d, J=6.90 Hz, 1H), 7.99-7.97 (m, 1H), 7.91-7.87 (m, 3H), 3.84-3.79 (m, 2H), 3.68-3.62 (m, 2H), 3.50-3.41 (m, 4H), 1.59 (s, 9H); ESI-MS m/z: calculated for 424.1. found 447.2 [M+Na]$^+$.

Example 78

Compound 78 of the present invention was prepared according to Scheme 4. The synthetic method was similar with Example 7, except that the N-(cyclopropanecarbonyl) piperazine was replaced. Firstly, 4-(furan-2-carbonyl)piperazine (corresponds to A ring with substituent R' of Formula (I) in Compound 78) was prepared, and obtained as white solid. $^1$H NMR (600 MHz, CDCl$_3$): δ 9.64 (s, 1H), 8.44 (d, J=7.74 Hz, 1H), 8.14 (d, J=7.92 Hz, 1H), 7.93-7.91 (m, 1H), 7.89-7.87 (m, 1H), 7.49 (s 1H), 7.34-7.31 (m, 2H), 7.18 (t, 1H, J=8.64 Hz), 7.07 (d, J=3.36 Hz, 1H), 6.51-6.50 (m, 1H), 3.92-3.84 (m, 6H), 3.51 (br, 2H); ESI-MS m/z: calculated for 462.13. found 463.08 [M+H]$^+$.

Example 79

Compound 79 of the present invention was prepared according to Scheme 4. The synthetic method was similar with Example 7, except that the N-(cyclopropanecarbonyl) piperazine was replaced. Firstly, 4-isopropylpiperazine (corresponds to A ring with substituent R' of Formula (I) in Compound 79) was prepared, and obtained as white solid. $^1$H NMR (600 MHz, CDCl$_3$): δ 9.07 (s, 1H), 8.44 (d, J=7.80 Hz, 1H), 8.14 (d, J=7.56 Hz, 1H), 7.93-7.91 (m, 1H), 7.89-7.87 (m, 1H), 7.30-7.28 (m, 2H), 7.15 (t, 1H, J=8.52 Hz), 3.81 (brs, 2H), 3.41 (brs, 2H), 2.75 (brs, 1H), 2.60 (brs, 2H), 2.50 (brs, 2H), 1.06 (d, 6H, J=6.00 Hz); ESI-MS m/z: calculated for 410.18. found 411.14 [M+H]$^+$.

Example 80

Compound 80 of the present invention was prepared according to Scheme 4. The synthetic method was similar with Example 7, except that the N-(cyclopropanecarbonyl) piperazine was replaced. Firstly, 4-allylpiperazine (corresponds to A ring with substituent R' of Formula (I) in Compound 80) was prepared, and obtained as white solid. $^1$H NMR (600 MHz, CDCl$_3$): δ 9.21 (s, 1H), 8.44 (d, J=7.86 Hz, 1H), 8.14 (d, J=7.98 Hz, 1H), 7.93-7.91 (m, 1H), 7.89-7.87 (m, 1H), 7.29-7.28 (m, 2H), 7.17-7.14 (m, 1H), 5.89-5.81 (m, 1H), 5.22-5.20 (m, 2H), 3.82 (brs, 2H), 3.42 (brs, 2H), 3.04 (d, 2H, J=6.36 Hz), 2.54-2.53 (m, 2H), 2.44 (brs, 2H); ESI-MS m/z: calculated for 408.16. found 409.15 [M+H]$^+$.

Example 81

Compound 81 of the present invention was prepared according to Scheme 4. The synthetic method was similar with Example 7, except that the N-(cyclopropanecarbonyl) piperazine was replaced. Firstly, 4-3-cyanobenzoylpiperazine (corresponds to A ring with substituent R' of Formula (I) in Compound 81) was prepared, and obtained as white solid. $^1$H NMR (600 MHz, CDCl$_3$): δ 9.72 (s, 1H), 8.45 (d, J=7.86 Hz, 1H), 8.15 (d, J=7.86 Hz, 1H), 7.95-7.93 (m, 1H), 7.91-7.88 (m, 1H), 7.75-7.68 (m, 2H), 7.66 (d, J=7.68 Hz, 1H), 7.58-7.56 (m, 1H), 7.34-7.32 (m, 2H), 7.21-7.14 (m, 1H), 3.83 (brs, 4H), 3.49 (brs, 4H); ESI-MS m/z: calculated for 497.15. found 496.22 [M−H]$^+$.

Example 82

Compound 82 of the present invention was prepared according to Scheme 4. The synthetic method was similar with Example 7, except that the N-(cyclopropanecarbonyl) piperazine was replaced. Firstly, 4-(1H-pyrazole-1-carbonyl) piperazine (corresponds to A ring with substituent R' of Formula (I) in Compound 82) was prepared, and obtained as white solid. $^1$H NMR (600 MHz, DMSO-d$_6$): δ 9.21 (s, 1H), 8.45 (d, J=6.72 Hz, 1H), 8.16-8.13 (m, 2H), 7.94-7.91 (m, 1H), 7.90-7.87 (m, 1H), 7.65 (brs, 1H), 7.35-7.28 (m, 2H), 7.20-7.17 (m, 1H), 6.39-6.38 (m, 1H), 4.03-3.94 (m, 4H), 3.56 (brs, 2H); ESI-MS m/z: calculated for 462.1. found 485.1 [M+Na]$^+$.

Example 83

Compound 83 of the present invention was prepared according to Scheme 4. The synthetic method was similar with Example 7, except that the N-(cyclopropanecarbonyl) piperazine was replaced. Firstly, 4-(morpholine-4-carbonyl) piperazine (corresponds to A ring with substituent R' of Formula (I) in Compound 83) was prepared, and obtained as white solid. $^1$H NMR (600 MHz, CDCl$_3$): δ 10.52 (s, 1H), 8.42 (d, J=7.74 Hz, 1H), 8.11 (d, J=7.80 Hz, 1H), 7.91-7.89 (m, 1H), 7.87-7.84 (m, 1H), 7.29-7.28 (m, 2H), 7.15-7.12 (m, 1H), 3.78 (brs, 2H), 3.67-3.65 (m, 4H), 3.43 (brs, 2H), 3.35-3.34 (m, 2H), 3.28-3.27 (m, 6H); ESI-MS m/z: calculated for 481.18. found 480.22 [M+H]$^+$.

Example 84

Compound 84 of the present invention was prepared according to Scheme 4. The synthetic method was similar with Example 7, except that the N-(cyclopropanecarbonyl) piperazine was replaced. Firstly, 4-(pyrrolidine-1-carbonyl) piperazine (corresponds to A ring with substituent R' of Formula (I) in Compound 84) was prepared, and obtained as white solid. ¹H NMR (600 MHz, CDCl₃): δ 10.14 (s, 1H), 8.43 (d, J=7.86 Hz, 1H), 8.12 (d, J=7.86 Hz, 1H), 7.92-7.89 (m, 1H), 7.87-7.85 (m, 1H), 7.30-7.29 (m, 2H), 7.16-7.14 (m, 1H), 3.80 (brs, 2H), 3.43-3.41 (m, 2H), 340-3.37 (m, 6H), 3.31-3.29 (m, 2H), 1.83 (brs, 4H); ESI-MS m/z: calculated for 465.18. found 464.30 [M−H]⁺.

Example 85

Compound 85 of the present invention was prepared according to Scheme 4. The synthetic method was similar with Example 7, except that the N-(cyclopropanecarbonyl) piperazine was replaced. Firstly, 4-(piperidine-1-carbonyl) piperazine (corresponds to A with substituent R' of Formula (I) in Compound 85) was prepared, and obtained as white solid. ¹H NMR (600 MHz, CDCl₃): δ 9.19 (s, 1H), 8.44 (d, J=7.74 Hz, 1H), 8.13 (d, J=7.62 Hz, 1H), 7.94-7.91 (m, 1H), 7.89-7.87 (m, 1H), 7.31-7.28 (m, 2H), 7.18-7.15 (m, 1H), 3.82-3.79 (m, 2H), 3.45-3.40 (m, 2H), 3.33-3.31 (m, 2H), 3.26-3.25 (m, 2H), 3.24-3.22 (m, 4H), 1.62-1.56 (m, 6H); ESI-MS m/z: calculated for 479.20. found 478.30 [M−H]⁺.

Example 86

Compound 86 of the present invention was prepared according to Scheme 4. The synthetic method was similar with Example 7, except that the N-(cyclopropanecarbonyl) piperazine was replaced. Firstly, N-(3-(trifluoromethyl)phenyl)piperazine-1-formamide (corresponds to A ring with substituent R' of Formula (I) in Compound 86) was prepared, and obtained as white solid. ¹H NMR (600 MHz, CDCl₃): δ 9.52 (s, 1H), 8.43 (d, J=7.8 Hz, 1H), 8.13 (d, J=7.8 Hz, 1H), 7.92-7.86 (m, 2H), 7.64-7.62 (m, 1H), 7.57-7.56 (m, 2H), 7.42-7.38 (m, 2H), 7.42-7.38 (m, 2H), 3.62-3.59 (m, 4H), 3.53-3.48 (m, 4H); ESI-MS m/z: calculated for 555.5. found 554.0[M−H]⁺.

Example 87

Compound 87 of the present invention was prepared according to Scheme 4. The synthetic method was similar with Example 7, except that the N-(cyclopropanecarbonyl) piperazine was replaced. Firstly, 4-(3-nitrobenzoyl)piperazine (corresponds to A ring with substituent R' of Formula (I) in Compound 87) was prepared, and obtained as white solid. ¹H NMR (600 MHz, DMSO-d₆): δ 11.96 (m, 1H), 8.29 (d, 1H, J=6.96 Hz), 8.27-8.24 (m, 2H), 8.10 (brs, 1H), 8.01-7.99 (m, 1H), 7.96-7.93 (m 1H), 7.87-7.86 (m, 1H), 7.74 (brs, 1H), 7.43 (brs, 3H), 3.75-3.65 (m, 4H), 3.41-3.32 (m, 4H); ESI-MS m/z: calculated for 517.14. found 515.99 [M−H]⁺.

Example 88

Compound 88 of the present invention was prepared according to Scheme 4. The synthetic method was similar with Example 7, except that the N-(cyclopropanecarbonyl) piperazine was replaced. Firstly, 4-(2-nitrobenzoyl)piperazine (corresponds to A ring with substituent R' of Formula (I) in Compound 88) was prepared, and obtained as white solid. ¹H NMR (600 MHz, CDCl₃): δ 9.30 (m, 1H), 8.46-8.43 (m, 1H), 8.23-8.18 (m, 1H), 8.16-8.11 (m, 1H), 7.94-7.88 (m, 2H), 7.77-7.71 (m, 1H), 7.64-7.57 (m, 1H), 7.42-7.40 (m, 1H), 7.36-7.34 (m 1H), 7.31-7.30 (m, 1H), 7.23-7.20 (m, 1H), 4.24-3.68 (m, 4H), 3.59-3.28 (m, 4H); ESI-MS m/z: calculated for 517.14. found 516.10 [M−H]⁺.

Example 89

Compound 89 of the present invention was prepared according to Scheme 4. The synthetic method was similar with Example 7, except that the N-(cyclopropanecarbonyl) piperazine was replaced. Firstly, 4-but-2-enoylpiperazine (corresponds to A ring with substituent R' of Formula (I) in Compound 89) was prepared, and obtained as white solid. ¹H NMR (600 MHz, CDCl₃) δ 9.59 (s, 1H), 8.44 (d, J=7.68 Hz, 1H), 8.14 (d, J=7.80 Hz, 1H), 7.94-7.91 (m, 1H), 7.89-7.87 (m, 1H), 7.33-7.31 (m, 2H), 7.19-7.16 (m, 1H), 6.96-6.90 (m, 1H), 6.26 (brs, 1H), 3.82-3.60 (m, 6H), 3.44 (brs, 2H), 1.90 (brs, 3H); ESI-MS m/z: calculated for 436.15. found 435.06 [M−H]⁺.

Example 90

Compound 90 of the present invention was prepared according to Scheme 4. The synthetic method was similar with Example 7, except that the N-(cyclopropanecarbonyl) piperazine was replaced. Firstly, 4-methylpiperazine (corresponds to A ring with substituent R' of Formula (I) in Compound 90) was prepared, and obtained as white solid. ¹H NMR (600 MHz, CDCl₃): δ 10.16 (s, 1H), 8.43 (d, 1H, J=7.74 Hz), 8.13 (d, 1H, J=7.80 Hz), 7.92-7.90 (m, 1H), 7.88-7.85 (m, 1H), 7.29-7.27 (m, 2H), 7.16-7.13 (m, 1H), 3.84 (brs, 2H), 3.45 (brs, 2H), 2.53 (brs, 2H), 2.45 (brs, 2H), 2.35 (s, 3H); ESI-MS m/z: calculated for 382.14. found 381.17 [M−H]⁺.

Example 91

Compound 91 of the present invention was prepared according to Scheme 4. The synthetic method was similar with Example 7, except that the N-(cyclopropanecarbonyl) piperazine was replaced. Firstly, 4-(oxazole-4-carbonyl)piperazine (corresponds to A ring with substituent R' of Formula (I) in Compound 91) was prepared, and obtained as white solid. ¹H NMR (600 MHz, CDCl₃): δ 9.73 (s, 1H), 8.44 (d, J=7.74 Hz, 1H), 8.26 (s, 1H), 8.14 (d, J=7.80 Hz, 1H), 7.93-7.86 (m, 3H), 7.35-7.30 (m, 2H), 7.19-7.16 (m, 1H), 4.23-4.09 (m, 2H), 3.89-3.79 (m, 4H), 3.51 (brs, 2H); ESI-MS m/z: calculated for 463.13. found 463.92 [M+H]⁺.

Example 92

Compound 92 of the present invention was prepared according to Scheme 4. The synthetic method was similar with Example 7, except that the N-(cyclopropanecarbonyl) piperazine was replaced. Firstly, 4-(2-hydroxyethyl)piperazine (corresponds to A ring with substituent R' of Formula (I) in Compound 92) was prepared, and obtained as white solid. ¹H NMR (600 MHz, CDCl₃): δ 10.14 (s, 1H), 8.43 (d, J=7.80 Hz, 1H), 8.13 (d, J=7.92 Hz, 1H), 7.93-7.92 (m, 1H), 7.89-7.86 (m, 1H), 7.29-7.26 (m, 2H), 7.16-7.14 (m, 1H), 3.82 (brs, 2H), 3.67-3.65 (m, 2H), 3.43 (brs, 2H), 2.63-2.59 (m, 4H), 2.53 (brs, 2H); ESI-MS m/z: calculated for 412.15. found 411.30 [M−H]⁺.

Example 93

Compound 93 of the present invention was prepared according to Scheme 4. The synthetic method was similar with Example 7, except that the N-(cyclopropanecarbonyl)

piperazine was replaced. Firstly, 4-(1H-1,2,4-triazole-1-carbonyl)piperazine (corresponds to A ring with substituent R' of Formula (I) in Compound 93) was prepared, and obtained as white solid. $^1$H NMR (600 MHz, DMSO-d$_6$): δ 9.25 (s, 1H), 8.46-8.42 (m, 2H), 8.14 (d, J=7.86 Hz, 1H), 7.94-7.92 (m, 1H), 7.90-7.88 (m, 1H), 7.46-7.44 (m, 1H), 7.38-7.35 (m, 2H), 7.22-7.19 (m, 1H), 4.02-3.99 (m, 4H), 3.73-3.59 (m, 4H); ESI-MS m/z: calculated for 463.1. found 486.2 [M+Na]$^+$.

Example 94

Compound 94 of the present invention was prepared according to Scheme 4. The synthetic method was similar with Example 7, except that the N-(cyclopropanecarbonyl) piperazine was replaced. Firstly, 4-(tetrahydrofuran-2-carbonyl)piperazine (corresponds to A ring with substituent R' of Formula (I) in Compound 94) was prepared, and obtained as white solid. $^1$H NMR (600 MHz, DMSO-d$_6$): δ 9.22 (s, 1H), 8.45 (d, J=7.56 Hz, 1H), 8.14 (d, J=7.44 Hz, 1H), 7.94-7.91 (m, 1H), 7.90-7.87 (m, 1H), 7.32-7.31 (m, 2H), 7.19-7.16 (m, 1H), 4.62-4.55 (m, 1H), 4.00-3.81 (m, 5H), 3.72-3.50 (m, 5H), 2.39-2.38 (m, 1H), 2.07-2.00 (m, 2H), 1.94-1.91 (m, 1H); ESI-MS m/z: calculated for 466.1. found 488.9 [M+Na]$^+$.

Example 95

Compound 95 of the present invention was prepared according to Scheme 4. The synthetic method was similar with Example 7, except that the N-(cyclopropanecarbonyl) piperazine was replaced. Firstly, 4-(tetrahydrofuran-2-carbonyl)piperazine (corresponds to A ring with substituent R' of Formula (I) in Compound 95) was prepared, and obtained as white solid. $^1$H NMR (600 MHz, CDCl$_3$): δ 10.00 (s, 1H), 8.44 (d, J=7.80 Hz, 1H), 8.13 (d, J=7.86 Hz, 1H), 7.93-7.90 (m, 1H), 7.89-7.86 (m, 1H), 7.32-7.31 (m, 2H), 7.18-7.15 (m, 1H), 4.62-4.55 (m, 1H), 3.97-3.81 (m, 5H), 3.69-3.39 (m, 5H), 2.38-2.34 (m, 1H), 2.06-1.99 (m, 2H), 1.94-1.89 (m, 1H); ESI-MS m/z: calculated for 466.17. found 465.27 [M−H]$^+$.

Example 96

Compound 96 of the present invention was prepared according to Scheme 4. The synthetic method was similar with Example 7, except that the N-(cyclopropanecarbonyl) piperazine was replaced. Firstly, N-(4,4-difluorocyclohexyl) piperazine-1-formamide (corresponds to A ring with substituent R' of Formula (I) in Compound 96) was prepared, and obtained as white solid. $^1$H NMR (600 MHz, CDCl$_3$): δ 9.96 (d, J=7.8 Hz, 1H), 8.43 (d, J=7.68 Hz, 1H), 8.14 (d, J=7.80 Hz, 1H), 7.99-7.91 (m, 1H), 7.89-7.87 (m, 1H), 7.31-7.30 (m, 2H), 7.18-7.15 (m, 1H), 4.53-4.48 (m, 1H), 3.80 (brs, 2H), 3.44 (brs, 6H), 2.44-2.34 (m, 1H), 2.23-2.19 (m, 1H), 2.11-1.72 (m, 5H), 1.50-1.42 (m, 1H); ESI-MS m/z: calculated for 529.19. found 528.09 [M−H]$^+$.

Example 97

Compound 97 of the present invention was prepared according to Scheme 4. The synthetic method was similar with Example 7, except that the N-(cyclopropanecarbonyl) piperazine was replaced. Firstly, N-cyclopropylpiperazine-1-formamide (corresponds to A ring with substituent R' of Formula (I) in Compound 97) was prepared, and obtained as white solid. $^1$H NMR (600 MHz, CDCl$_3$): δ 10.14 (s, 1H), 8.43 (d, J=7.74 Hz, 1H), 8.13 (d, J=7.68 Hz, 1H), 7.91-7.90 (m, 1H), 7.89-7.87 (m, 1H), 7.31-7.30 (m, 2H), 7.17-7.14 (m, 1H), 4.93 (brs, 1H), 3.78 (brs, 2H), 3.44-3.42 (m, 6H), 0.71-0.69 (m, 2H), 0.45 (brs, 2H); ESI-MS m/z: calculated for 451.17. found 450.00 [M−H]$^+$.

Example 98

Compound 98 of the present invention was prepared according to Scheme 4. The synthetic method was similar with Example 7, except that the N-(cyclopropanecarbonyl) piperazine was replaced. Firstly, 4-(1H-imidazole-1-carbonyl)piperazine (corresponds to A ring with substituent R' of Formula (I) in Compound 98) was prepared, and obtained as white solid. $^1$H NMR (600 MHz, CDCl$_3$): δ 9.69 (s, 1H), 8.40 (d, J=7.62 Hz, 1H), 8.34 (s, 1H), 8.12 (d, J=7.86 Hz, 1H), 7.93-7.90 (m, 1H), 7.88-7.86 (m, 1H), 7.34-7.28 (m, 3H), 7.22-7.21 (m, 1H), 7.19-7.16 (m, 1H), 3.90 (brs, 2H), 3.74 (brs, 2H), 3.68 (brs, 2H) 3.55 (brs, 2H); ESI-MS m/z: calculated for 462.43. found 461.11 [M−H]$^+$.

Example 99

Compound 99 of the present invention was prepared according to Scheme 4. The synthetic method was similar with Example 7, except that the N-(cyclopropanecarbonyl) piperazine was replaced. Firstly, 4-(cyclohexanecarbonyl) piperazine (corresponds to A ring with substituent R' of Formula (I) in Compound 99) was prepared, and obtained as white solid. $^1$H NMR (600 MHz, CDCl$_3$): δ 10.78 (s, 1H), 8.41 (d, J=7.74 Hz, 1H), 8.11 (d, J=7.80 Hz, 1H), 7.91-7.88 (m, 1H), 7.86-7.84 (m, 1H), 7.30-7.29 (m, 2H), 7.15-7.12 (m, 1H), 3.80-3.54 (m, 6H), 3.44-3.39 (m, 2H), 2.48-2.41 (m, 1H), 1.78-1.69 (m, 5H), 1.54-1.48 (m, 2H), 1.29-1.21 (m, 3H); ESI-MS m/z: calculated for 478.52. found 477.22 [M−H]$^+$.

Example 100

Compound 100 of the present invention was prepared according to Scheme 4. The synthetic method was similar with Example 7, except that the N-(cyclopropanecarbonyl) piperazine was replaced. Firstly, 4-propionylpiperazine (corresponds to A ring with substituent R' of Formula (I) in Compound 100) was prepared, and obtained as white solid. $^1$H NMR (600 MHz, CDCl$_3$): δ 10.69 (s, 1H), 8.41 (d, 1H, J=7.80 Hz), 8.11 (d, 1H, J=7.86 Hz), 7.90 (t, 1H, J=7.41 Hz), 7.86 (t, 1H, J=7.38 Hz), 7.31-7.29 (m, 2H), 7.15 (t, 1H, J=8.88 Hz), 3.79-3.65 (m, 4H), 3.56-3.40 (m, 4H), 2.40-2.37 (m, 1H), 2.32-2.31 (m, 1H), 1.16-1.11 (m, 3H); ESI-MS m/z: calculated for 424.42. found 423.13 [M−H]$^+$.

Example 101

Compound 101 of the present invention was prepared according to Scheme 4. The synthetic method was similar with Example 7, except that the N-(cyclopropanecarbonyl) piperazine was replaced. Firstly, 4-(cyclopentylcarbonyl)piperazine (corresponds to A ring with substituent R' of Formula (I) in Compound 101) was prepared, and obtained as white solid. $^1$H NMR (600 MHz, CDCl$_3$): δ 10.14 (s, 1H), 8.43 (d, J=7.80 Hz, 1H), 8.13 (d, J=7.86 Hz, 1H), 7.95-7.90 (m, 1H), 7.89-7.86 (m, 1H), 7.31-7.30 (m, 2H), 7.18-7.15 (m, 1H), 3.80-3.57 (m, 6H), 3.44-3.40 (m, 2H), 2.19 (brs, 1H), 1.83-1.74 (m, 8H); ESI-MS m/z: calculated for 464.49. found 463.21[M−H]$^+$.

Example 102

Compound 102 of the present invention was prepared according to Scheme 3. The synthetic method was similar with Example 7, except that the N-(cyclopropanecarbonyl)piperazine was replaced. Firstly, 4-(4-benzyloxycarbonyl-piperidine)carbonylpiperazine (corresponds to A ring with substituent R' of Formula (I) in Compound 102) was prepared, and obtained as white solid. $^1$H NMR (600 MHz, DMSO-$d_6$): δ 12.23 (s, 1H), 8.27 (d, J=7.56 Hz, 1H), 8.06-8.05 (m, 1H), 7.88 (t, 1H, J=7.92 Hz), 7.37-7.32 (m, 7H), 7.31-7.28 (m, 1H), 5.05 (s, 2H), 3.99-3.98 (m, 2H), 3.63-3.57 (m, 3H), 3.51-3.44 (m, 5H), 2.88-2.79 (m, 3H), 1.62 (brs, 2H), 1.44-1.37 (m, 2H); ESI-MS m/z: calculated for 647.2. found 646.3 [M−H]$^+$.

Example 103

Compound 103 of the present invention was prepared according to Scheme 4. The synthetic method was similar with Example 7, except that the N-(cyclopropanecarbonyl)piperazine was replaced. Firstly, 4-benzoylpiperazine (corresponds to A ring with substituent R' of Formula (I) in Compound 103) was prepared, and obtained as white solid. $^1$H NMR (600 MHz, DMSO-$d_6$): δ 11.98 (s, 1H), 8.28 (d, J=7.80 Hz, 1H), 8.12 (d, J=8.22 Hz, 1H), 8.03-8.00 (m, 1H), 7.98-7.95 (m, 1H), 7.51-7.49 (m, 2H), 7.47-7.40 (m, 4H), 7.28 (t, 2H, J=8.64 Hz), 3.74-3.36 (m, 8H); ESI-MS m/z: calculated for 472.15. found 471.27[M−H]$^+$.

Example 104

Compound 104 of the present invention was prepared according to Scheme 3. The synthetic method was similar with Example 7, except that the N-(cyclopropanecarbonyl)piperazine was replaced. Firstly, 4-(4-fluorophenyl)piperazine (corresponds to A ring with substituent R' of Formula (I) in Compound 104) was prepared, and obtained as white solid. $^1$H NMR (600 MHz, DMSO-$d_6$): δ 12.22 (s, 1H), 8.27-8.26 (m, 1H), 8.06 (d, J=7.74 Hz, 1H), 7.88 (t, 1H, J=7.95 Hz), 7.37-7.34 (m, 3H), 7.06-7.03 (m, 2H), 6.97-6.94 (m, 2H), 3.76-3.75 (m, 2H), 3.39-3.37 (m, 2H), 3.14-3.12 (m, 2H), 3.05-3.03 (m, 2H); ESI-MS m/z: calculated for 496.0. found 497.0 [M+H]$^+$.

Example 105

Compound 105 of the present invention was prepared according to Scheme 3. The synthetic method was similar with Example 1, except that the N-(cyclopropanecarbonyl)piperazine was replaced. Firstly, 4-(4-benzyloxycarbonyl-piperidine)carbonylpiperazine (corresponds to A ring with substituent R' of Formula (I) in Compound 105) was prepared, and obtained as white solid. $^1$H NMR (600 MHz, DMSO-$d_6$): δ 12.06 (s, 1H), 8.10-8.08 (m, 1H), 7.90-7.89 (m, 1H), 7.80-7.77 (m, 1H), 7.61 (d, J=7.50 Hz, 1H), 7.54 (s, 1H), 7.49 (t, J=7.56 Hz, 1H), 7.39 (d, J=7.62 Hz, 1H), 7.37-7.28 (m, 5H), 5.38 (s, 2H), 5.06 (s, 2H), 3.40-3.98 (m, 2H), 3.62-3.38 (m, 8H), 2.87 (brs, 3H), 1.61 (brs, 2H), 1.44-1.39 (m, 2H); ESI-MS m/z: calculated for 627.3. found 650.6 [M+Na]$^+$.

Example 106

Compound 106 of the present invention was prepared according to Scheme 3. The synthetic method was similar with Example 7, except that the N-(cyclopropanecarbonyl)piperazine was replaced. Firstly, 4-(4-nitrobenzoyl)piperazine (corresponds to A ring with substituent R' of Formula (I) in Compound 106) was prepared, and obtained as white solid. $^1$H NMR (600 MHz, DMSO-$d_6$): δ 12.24 (s, 1H), 8.27-8.26 (m, 3H), 8.05 (brs, 1H), 7.90-7.87 (m, 1H), 7.69 (brs, 2H), 7.36 (brs, 3H), 3.72-3.64 (m, 4H), 3.28-3.26 (m, 4H); ESI-MS m/z: calculated for 551.1. found 550.1[M+H]$^+$.

Example 107

Compound 107 of the present invention was prepared according to Scheme 4. The synthetic method was similar with Example 7, except that the N-(cyclopropanecarbonyl)piperazine was replaced. Firstly, 4-(4,4-difluorocyclohexanecarbonyl)piperazine (corresponds to A ring with substituent R' of Formula (I) in Compound 107) was prepared, and obtained as white solid. $^1$H NMR (600 MHz, CDCl$_3$): δ 9.71 (s, 1H), 8.44 (d, J=7.74 Hz, 1H), 8.13 (d, J=7.80 Hz, 1H), 7.94-7.91 (m, 1H), 7.90-7.87 (m, 1H), 7.33-7.31 (m, 2H), 7.19-7.16 (m, 1H), 3.82-3.66 (m, 4H), 3.61-3.42 (m, 4H), 2.61-2.54 (m, 1H), 2.23-2.19 (m, 2H), 1.95-1.89 (m, 2H), 1.83-1.72 (m, 4H); ESI-MS m/z: calculated for 514.20. found 537.06 [M+Na]$^+$.

Example 108

Compound 108 of the present invention was prepared according to Scheme 4. The synthetic method was similar with Example 7, except that the N-(cyclopropanecarbonyl)piperazine was replaced. Firstly, 4-(4-benzyloxycarbonyl-pyrrolidine)carbonylpiperazine (corresponds to A ring with substituent R' of Formula (I) in Compound 108) was prepared, and obtained as white solid. $^1$H NMR (600 MHz, CDCl$_3$): δ 9.27 (s, 1H), 8.44 (d, J=8.3 Hz, 1H), 8.13 (br, 1H), 7.90 (m, 2H), 7.33 (m, 7H), 7.18 (s, 1H), 5.15 (m, 2H), 3.84 (br, 1H), 3.50 (m, 8H), 2.19 (m, 4H), 1.91 (br, 2H); ESI-MS m/z: calculated for 599.21. found 622.26 [M+Na]$^+$.

Example 109

Compound 109 of the present invention was prepared according to Scheme 4. The synthetic method was similar with Example 7, except that the N-(cyclopropanecarbonyl)piperazine was replaced. Firstly, 4-(pyrrolidine-2-carbonyl)piperazine (corresponds to A ring with substituent R' of Formula (I) in Compound 109) was prepared, and obtained as white solid. $^1$H NMR (600 MHz, CDCl$_3$): δ 8.44 (s, 1H), 8.15 (d, J=7.7 Hz, 1H), 7.88 (m, 3H), 7.43 (m, 2H), 7.19 (s, 1H), 4.06 (m, 2H), 3.74 (m, 2H), 3.53 (m, 8H), 2.63 (brs, 1H), 2.26-2.19 (m, 2H); ESI-MS m/z: calculated for 465.18. found 465.98 [M+H]$^+$.

Example 110

Compound 110 of the present invention was prepared according to Scheme 4. The synthetic method was similar with Example 7, except that the N-(cyclopropanecarbonyl)piperazine was replaced. Firstly, 4-(4-fluorophenyl)piperazine (corresponds to A ring with substituent R' of Formula (I) in Compound 110) was prepared, and obtained as white solid. $^1$H NMR (600 MHz, CDCl$_3$) δ 10.20 (s, 1H), 8.42 (d, J=7.86 Hz, 1H), 8.14 (d, J=7.92 Hz, 1H), 7.93-7.90 (m, 1H), 7.86-7.84 (m, 1H), 7.34-7.30 (m, 2H), 7.17 (t, 1H, J=8.67 Hz), 6.97-6.94 (m, 2H), 6.90-6.88 (m, 2H), 3.96 (brs, 2H), 3.58 (brs, 2H), 3.18-3.17 (m, 2H), 3.10 (brs, 2H). ESI-MS m/z: calculated for 462.45. found 461.16 [M−H]$^+$.

Example 111

Compound III of the present invention was prepared according to Scheme 4. The synthetic method was similar with Example 7, except that the N-(cyclopropanecarbonyl) piperazine was replaced. Firstly, 4-(tetrahydrofuran-3-carbonyl)piperazine (corresponds to A ring with substituent R' of Formula (I) in Compound III) was prepared, and obtained as white solid. $^1$H NMR (600 MHz, CDCl$_3$): δ 10.16 (m, 1H), 8.43 (d, J=7.80 Hz, 1H), 8.13 (d, J=7.74 Hz, 1H), 7.93-7.90 (m, 1H), 7.89-7.86 (m, 1H), 7.33-7.31 (m, 2H), 7.19-7.16 (m, 1H), 4.03-3.96 (m, 1H), 3.90-3.56 (m, 9H), 3.46-3.42 (m, 3H), 2.25-2.20 (m, 1H), 2.13-2.02 (m, 1H); ESI-MS m/z: 466.16. found 488.78 [M+Na]$^+$.

Example 112

Compound 112 of the present invention was prepared according to Scheme 4. The synthetic method was similar with Example 7, except that the N-(cyclopropanecarbonyl) piperazine was replaced. Firstly, N-(4-chlorophenyl)piperazine-1-formamide (corresponds to A ring with substituent R' of Formula (I) in Compound 112) was prepared, and obtained as white solid. $^1$H NMR (600 MHz, CDCl$_3$): δ 9.59 (s, 1H), 8.43 (d, J=7.86 Hz, 1H), 8.14 (d, J=7.50 Hz, 1H), 7.94-7.91 (m, 1H), 7.89-7.86 (m, 1H), 7.33-7.28 (m, 4H), 7.24-7.23 (m, 2H), 7.20-7.17 (m, 1H), 6.51 (s, 1H), 3.87 (brs, 2H), 3.61-3.57 (m, 4H), 3.50 (brs, 2H); ESI-MS m/z: calculated for 521.13. found 521.91 (M+H]$^+$.

Example 113

Compound 113 of the present invention was prepared according to Scheme 4. The synthetic method was similar with Example 7, except that the N-(cyclopropanecarbonyl) piperazine was replaced. Firstly, N,N-diethylpiperazine-1-formamide (corresponds to A ring with substituent R' of Formula (I) in Compound 113) was prepared, and obtained as white solid. $^1$H NMR (600 MHz, CDCl$_3$): δ 10.09 (s, 1H), 8.43 (d, J=7.68 Hz, 1H), 8.13 (d, J=7.74 Hz, 1H), 7.92-7.90 (m, 1H), 7.88-7.85 (m, 1H), 7.30-7.28 (m, 2H), 7.16-9.13 (m, 1H), 3.80 (brs, 2H), 3.44 (brs, 2H), 3.30-3.29 (m, 2H), 3.24-3.21 (m, 6H), 1.13 (t, 6H, J=7.05 Hz); ESI-MS m/z: calculated for 467.20. found 465.93 [M-H]$^+$.

Example 114

Compound 114 of the present invention was prepared according to Scheme 4. The synthetic method was similar with Example 7, except that the N-(cyclopropanecarbonyl) piperazine was replaced. Firstly, 4-(tetrahydropyran-4-carbonyl)piperazine (corresponds to A ring with substituent R' of Formula (I) in Compound 114) was prepared, and obtained as white solid. $^1$H NMR (600 MHz, CDCl$_3$): δ 10.57 (s, 1H), 8.41 (d, J=7.68 Hz, 1H), 8.12 (d, J=7.86 Hz, 1H), 7.91-7.89 (m, 1H), 7.87-7.85 (m, 1H), 7.31-7.30 (m, 2H), 7.17-7.14 (m, 1H), 4.00 (brs, 2H), 3.87-3.56 (m, 6H), 3.45-3.41 (m, 4H), 2.76-2.69 (m, 1H), 1.94-1.87 (m, 2H), 1.61-1.59 (m, 2H); ESI-MS m/z: calculated for 480.18. found 479.14 [M-H]$^+$.

Example 115

Compound 115 of the present invention was prepared according to Scheme 4. The synthetic method was similar with Example 7, except that the N-(cyclopropanecarbonyl) piperazine was replaced. Firstly, 4-(4-(trifluoromethyl)benzoyl)piperazine (corresponds to A ring with substituent R' of Formula (I) in Compound 115) was prepared, and obtained as white solid. $^1$H NMR (600 MHz, CDCl$_3$): δ 10.12 (s, 1H), 8.43 (d, J=7.80 Hz, 1H), 8.13 (d, J=7.56 Hz, 1H), 7.93-7.90 (m, 1H), 7.89-7.86 (m, 1H), 7.71-7.70 (m, 2H), 7.54-7.53 (m, 2H), 7.32 (brs, 2H), 7.21-7.14 (m, 1H), 3.90-3.76 (m, 4H), 3.57-3.41 (m, 4H); ESI-MS m/z: calculated for 540.14. found 539.23 [M-H].

Example 116

Compound 116 of the present invention was prepared according to Scheme 4. The synthetic method was similar with Example 7, except that the N-(cyclopropanecarbonyl) piperazine was replaced. Firstly, 4-(4-fluorobenzoyl)piperazine (corresponds to A ring with substituent R' of Formula (I) in Compound 116) was prepared, and obtained as white solid. $^1$H NMR (600 MHz, CDCl$_3$): δ 10.21 (s, 1H), 8.42 (d, J=7.74 Hz, 1H), 8.13 (d, J=7.74 Hz, 1H), 7.93-7.90 (m, 1H), 7.88-7.86 (m, 1H), 7.44-7.42 (m, 2H), 7.32-7.30 (m, 2H), 7.17-7.09 (m, 3H), 3.81-3.27 (m, 8H); ESI-MS; m/z: calculated for 490.15. found 491.01 [M+H]$^+$.

Example 117

Compound 117 of the present invention was prepared according to Scheme 4. The synthetic method was similar with Example 7, except that the N-(cyclopropanecarbonyl) piperazine was replaced. Firstly, 4-(4-fluorobenzyl)piperazine (corresponds to A ring with substituent R' of Formula (I) in Compound 117) was prepared, and obtained as white solid. $^1$H NMR (600 MHz, CDCl$_3$): δ 9.33 (s, 1H), 8.44 (d, J=7.92 Hz, 1H), 8.13 (d, J=7.92 Hz, 1H), 7.93-7.91 (m, 1H), 7.89-7.87 (m, 1H), 7.28-7.27 (m, 4H), 7.16-7.13 (m, 1H), 7.01 (t, 2H, J=8.58 Hz), 3.81 (brs, 2H), 3.51 (brs, 2H), 3.45-3.38 (m, 2H), 2.52 (brs, 2H), 2.42 (brs, 2H); ESI-MS m/z: calculated for 476.17. found 475.32 [M-H]$^+$.

Example 118

Compound 118 of the present invention was prepared according to Scheme 4. The synthetic method was similar with Example 7, except that the N-(cyclopropanecarbonyl) piperazine was replaced. Firstly, piperazine (corresponds to A ring with substituent R' of Formula (I) in Compound 118) was prepared, and obtained as white solid. $^1$H NMR (600 MHz, CDCl$_3$): 9.51 (s, 1H), 8.44 (d, J=7.8 Hz, 1H), 8.13 (d, J=7.8 Hz, 1H), 7.91-7.87 (m, 2H), 7.31-7.30 (m, 2H), 7.16-7.15 (m, 1H), 3.77 (brs, 2H), 3.53 (brs, 2H), 3.00 (brs, 2H), 2.95 (brs, 2H); ESI-MS m/z calculated for: 368.13. found: 367.15 [M-H]$^+$.

Example 119

Compound 119 of the present invention was prepared according to Scheme 4. The synthetic method was similar with Example 7, except that the N-(cyclopropanecarbonyl) piperazine was replaced. Firstly, 4-pyridineformylpiperazine (corresponds to A ring with substituent R' of Formula (I) in Compound 119) was prepared, and obtained as white solid. $^1$H NMR (600 MHz, CDCl$_3$) δ 9.26 (s, 1H), 8.62-8.56 (m, 1H), 8.45-8.44 (m, 1H), 8.15-8.12 (m, 1H), 7.93-7.91 (m, 1H), 7.89-7.87 (m, 1H), 7.83-7.81 (m, 1H), 7.73 (brs, 1H), 7.39-7.28 (m, 3H), 7.21-7.13 (m, 1H), 3.93-3.72 (m, 6H), 3.55-3.49 (m, 2H); ESI-MS m/z calculated for: 437.15. found: 437.96 [M+H]$^+$.

Example 120

Compound 120 of the present invention was prepared according to Scheme 4. The synthetic method was similar with Example 7, except that the N-(cyclopropanecarbonyl)

piperazine was replaced. Firstly, 4-(tetrahydrofuran-2-carbonyl)piperazine (corresponds to A ring with substituent R' of Formula (I) in Compound 120) was prepared, and obtained as white solid. $^1$H NMR (600 MHz, CDCl$_3$): δ 9.36 (s, 1H), 8.44 (d, J=7.56 Hz, 1H), 8.14 (d, J=7.56 Hz, 1H), 7.94-7.91 (m, 1H), 7.90-7.87 (m, 1H), 7.32-7.31 (m, 2H), 7.19-7.16 (m, 1H), 4.62-4.56 (m, 1H), 4.00-3.82 (m, 5H), 3.70-3.46 (m, 5H), 2.39-2.34 (m, 1H), 2.06-2.00 (m, 2H), 1.94-1.90 (m, 1H); ESI-MS m/z: calculated for 466.17. found 467.1 [M+H]$^+$.

Example 121

Compound 121 of the present invention was prepared according to Scheme 4. The synthetic method was similar with Example 7, except that the N-(cyclopropanecarbonyl)piperazine was replaced. Firstly, 4-(2-cyclopropylacetyl)piperazine (corresponds to A ring with substituent R' of Formula (I) in Compound 121) was prepared, and obtained as white solid. $^1$H NMR (600 MHz, CDCl$_3$): δ 9.93 (s, 1H), 8.43 (d, J=7.68 Hz, 1H), 8.13 (d, J=7.86 Hz, 1H), 7.93-7.90 (m, 1H), 7.89-7.86 (m, 1H), 7.32-7.31 (m, 2H), 7.18-7.16 (m, 1H), 3.80-3.67 (m, 4H), 3.57-3.42 (m, 4H), 2.33-2.27 (m, 2H), 1.04 (brs, 1H), 0.59-0.58 (m, 2H), 0.19-0.15 (m, 2H); ESI-MS m/z: calculated for 450.17. found 473.07 [M+Na]$^+$.

Example 122

Compound 122 of the present invention was prepared according to Scheme 4. The synthetic method was similar with Example 7, except that the N-(cyclopropanecarbonyl)piperazine was replaced. Firstly, 4-(2-cyclopentylacetyl)piperazine (corresponds to A ring with substituent R' of Formula (I) in Compound 122) was prepared, and obtained as white solid. $^1$H NMR (600 MHz, CDCl$_3$): δ 9.72 (s, 1H), 8.44 (d, J=7.26 Hz, 1H), 8.13 (d, 1H, J=7.80 Hz), 7.93-7.91 (m, 1H), 7.89-7.87 (m, 1H), 7.32-7.31 (m, 2H), 7.19-7.16 (m, 1H), 3.84-3.73 (m, 3H), 3.66 (brs, 1H), 3.59 (brs, 1H), 3.52 (brs, 1H), 3.47-3.40 (m, 2H), 2.41-2.34 (m, 2H), 1.86 (brs, 2H), 1.64-1.55 (m, 7H); ESI-MS m/z: calculated for 478.20. found 501.11 [M+Na]$^+$.

Example 123

Compound 123 of the present invention was prepared according to Scheme 4. The synthetic method was similar with Example 7, except that the N-(cyclopropanecarbonyl)piperazine was replaced. Firstly, 4-(1-(methylamino)cyclopropanecarbonyl)piperazine (corresponds to A ring with substituent R' of Formula (I) in Compound 123) was prepared, and obtained as white solid. $^1$H NMR (600 MHZ, DMSO-d$_6$): δ11.97 (s, 1H), 8.26 (d, J=7.80 Hz, 1H), 8.11 (d, J=7.92 Hz, 1H), 8.01-7.99 (m, 1H), 7.96-7.94 (m, 1H), 7.46-7.41 (m, 2H), 7.38 (t, 1H, J=8.88 Hz), 3.63-3.57 (m, 6H), 3.27-3.26 (m, 2H), 2.19 (s, 3H), 0.82-0.80 (m, 2H), 0.65-0.63 (m, 2H); ESI-MS m/z: calculated for 465.1. found 488.14 [M+Na]$^+$.

Example 124

Compound 124 of the present invention was prepared according to Scheme 4. The synthetic method was similar with Example 7, except that the N-(cyclopropanecarbonyl)piperazine was replaced. Firstly, 4-(1-(dimethylamino)cyclopropanecarbonyl)piperazine (corresponds to A ring with substituent R' of Formula (I) in Compound 124) was prepared, and obtained as white solid. $^1$H NMR (600 MHZ, DMSO-d$_6$): δ11.96 (s, 1H), 8.26 (d, J=7.92 Hz, 1H), 8.10 (d, J=7.80 Hz, 1H), 8.01-7.99 (m, 1H), 7.96-7.94 (m, 1H), 7.46-7.41 (m, 2H), 7.38 (t, 1H, J=8.85 Hz), 3.62-3.55 (m, 6H), 3.28-3.25 (m, 2H), 2.14 (s, 6H), 0.84-0.83 (m, 2H), 0.72-0.70 (m, 2H); ESI-MS m/z: calculated for 479.2. found 502.12 [M+Na]$^+$.

Example 125

Compound 125 of the present invention was prepared according to Scheme 4. The synthetic method was similar with Example 7, except that the N-(cyclopropanecarbonyl)piperazine was replaced. Firstly, 4-(1-aminocyclopropanecarbonyl)piperazine (corresponds to A ring with substituent R' of Formula (I) in Compound 125) was prepared, and obtained as white solid. $^1$H NMR (600 MHZ, DMSO-d$_6$): δ11.97 (s, 1H), 8.26 (d, J=7.62 Hz, 1H), 8.11 (d, J=8.10 Hz, 1H), 8.01-7.99 (m, 1H), 7.96-7.94 (m, 1H), 7.45-7.36 (m, 3H), 3.64-3.56 (m, 6H), 3.26-3.20 (m, 2H), 0.85-0.81 (m, 2H), 0.76 (brs, 1H), 0.63-0.62 (m, 1H); ESI-MS m/z: calculated for 451.45. found 450.56 [M−H]$^+$.

Example 126

Compound 126 of the present invention was prepared according to Scheme 4. The synthetic method was similar with Example 7, except that the N-(cyclopropanecarbonyl)piperazine was replaced. Firstly, 4-(1-(dimethylamino)cyclobutanecarbonyl)piperazine (corresponds to A ring with substituent R' of Formula (I) in Compound 126) was prepared, and obtained as white solid. $^1$H NMR (600 MHz, DMSO-d$_6$): δ 11.97 (s, 1H), 8.26 (d, J=7.8 Hz, 1H), 8.11-8.09 (m, 1H), 8.01-7.98 (m, 1H), 7.96-7.93 (m, 1H), 7.45-7.40 (m, 2H), 7.37-7.35 (m, 1H), 3.62-3.55 (m, 4H), 3.52-3.47 (m, 2H), 3.27-3.19 (m, 2H), 2.36-2.21 (m, 4H), 2.15 (s, 3H), 2.11 (s, 3H), 1.62-1.57 (m, 1H), 1.53-1.48 (m, 1H); ESI-MS m/z: calculated for 493.2. found 515.98 [M+Na]$^+$.

Example 127

Compound 127 of the present invention was prepared according to Scheme 4. The synthetic method was similar with Example 7, except that the N-(cyclopropanecarbonyl)piperazine was replaced. Firstly, 4-(1-(methylamino)cyclobutanecarbonyb)piperazine (corresponds to A ring with substituent R' of Formula (I) in Compound 127) was prepared, and obtained as white solid. $^1$H NMR (600 MHz, DMSO-d$_6$): δ 8.36 (d, J=7.8 Hz, 1H), 8.20 (d, J=7.8 Hz, 1H), 8.02-8.00 (m, 1H), 7.97-7.94 (m, 1H), 7.44-7.41 (m, 1H), 7.40-7.38 (m, 2H), 3.82-3.80 (m, 2H), 3.68-3.66 (m, 2H), 3.60-3.58 (m, 2H), 3.46-2.44 (m, 2H), 3.45 (s, 3H), 2.68-2.63 (m, 2H), 2.05-2.02 (m, 3H), 1.73-1.68 (m, 1H); ESI-MS m/z: calculated for 479.20. found 480.25 [M+H]$^+$.

Example 128

Compound 128 of the present invention was prepared according to Scheme 4. The synthetic method was similar with Example 7, except that the N-(cyclopropanecarbonyl)piperazine was replaced. Firstly, 4-(1-aminocyclobutanecarbonyl)piperazine (corresponds to A ring with substituent R' of Formula (I) in Compound 128) was prepared, and obtained as white solid. $^1$H NMR (600 MHz, DMSO-d$_6$): δ 11.97 (s, 1H), 8.26 (d, J=7.8 Hz, 1H), 8.11-8.09 (m, 1H), 8.01-7.98 (m, 1H), 7.96-7.93 (m, 1H), 7.45-7.43 (m, 1H), 7.41-7.36 (m, 2H), 3.63-3.52 (m, 3H), 3.51-3.41 (m, 4H), 3.36-3.32 (m, 1H), 2.73-2.54 (m, 1H), 2.23-2.10 (m, 1H), 1.83-1.70 (m, 2H), 1.64-1.57 (m, 1H), 1.54-1.43 (m, 1H); ESI-MS m/z: calculated for 465.2. found 487.77 [M+Na]$^+$.

Example 129

Compound 129 of the present invention was prepared according to Scheme 4. The synthetic method was similar with Example 7, except that the N-(cyclopropanecarbonyl) piperazine was replaced. Firstly, 4-(1,2-dimethylpyrrolidine-2-carbonyl)piperazine (corresponds to A ring with substituent R' of Formula (I) in Compound 129) was prepared, and obtained as white solid. $^1$H NMR (600 MHz, DMSO-d$_6$): δ 8.36 (d, J=7.2 Hz, 1H), 8.20 (d, J=7.2 Hz, 1H), 8.02-7.99 (m, 1H), 7.96-7.94 (m, 1H), 7.44-7.43 (m, 1H), 7.40-7.38 (m, 1H), 7.32-7.29 (m, 1H), 3.82 (brs, 4H), 3.73 (brs, 2H), 3.47 (brs, 2H), 3.42 (brs, 1H), 3.02 (brs, 1H), 2.70 (s, 3H), 2.38-2.34 (m, 1H), 2.23 (brs, 1H), 2.10 (brs, 1H), 2.02-1.97 (m, 1H), 1.52 (s, 3H); ESI-MS m/z: calculated for 493.2. found 491.96 [M–H]$^+$.

Example 130

Compound 130 of the present invention was prepared according to Scheme 4. The synthetic method was similar with Example 7, except that the N-(cyclopropanecarbonyl) piperazine was replaced. Firstly, 4-(2-methylpyrrolidine-2-carbonyl)piperazine (corresponds to A ring with substituent R' of Formula (I) in Compound 130) was prepared, and obtained as white solid. $^1$H NMR (600 MHz, DMSO-d$_6$): δ 8.37 (d, J=7.2 Hz, 1H), 8.21 (d, J=7.2 Hz, 1H), 8.03-8.00 (m, 1H), 7.97-7.95 (m, 1H), 7.46-7.42 (m, 1H), 7.41-7.38 (m, 1H), 7.33-7.29 (m, 1H), 3.88-3.82 (m, 2H), 3.81-3.77 (m, 2H), 3.75-3.69 (m, 2H), 3.55-3.50 (m, 2H), 2.35-2.22 (m, 2H), 2.08-2.00 (m, 2H), 1.65 (s, 3H), 1.61-1.58 (m, 2H); ESI-MS m/z: calculated for 479.2. found 479.93 [M+H]$^+$.

Biological Evaluation

Test Example 1

Screening Assay for Poly (ADP-Ribose) Polymerase (PARP-1) Inhibition

The following in vitro screening assay is used to evaluate the PARP-1 inhibiting effect of the compounds of present invention.

Principle

PARP-1 can catalyze the NAD-dependent addition of poly (ADP-ribose) to adjacent nuclear proteins such as histone. The activity of PARP was determined by detecting biotin coupled ADP-ribose that attaches to histone using chemiluminescence method with HT Universal Chemiluminescent PARP Assay Kit With Histone-coated Strip Wells purchased from TREVIGEN. The positive control compound was AZD-2281 purchased from SelleckChem.

Method

The kit is based on ELISA. X µl sample/well, Y µl PARP enzyme/well and PARP cocktail 25 µl/well with a total volume of 50 µl/well were added into a 96-well plate coated with histone. Meanwhile, blank control (without enzyme and sample) and negative control (without sample) were set. The plate was incubated at room temperature for 60 min; washed with 1×PBS (+0.1% TritonX-100) for twice; Strep-HRP 50 µl/well was added and incubated at room temperature for 60 min; and then washed with 1×PBS (+0.1% TritonX-100) for twice, chemiluminescence substrate 100 µl/well was added for measurement. The inhibition rate was calculated according to the value of chemiluminescence intensity RLU (relative light unit), inhibition rate=[1−(RLU sample RLU blank)/(RLU negative RLU blank)]×100%. Each sample was gradiently diluted into eight concentrations, each concentration was set in a single well, IC$_{50}$ values were calculated using 4 Parameter Logistic Model in XLfit software according to the inhibition rate of samples. The results were shown in the following Table 1.

TABLE 1

| Compound No. | IC$_{50}$ (PARP-1)/µM |
| --- | --- |
| AZD-2281 | 0.012 |
| 61 | 0.008 |
| 85 | 0.009 |
| 88 | 0.015 |
| 99 | 0.017 |
| 100 | 0.03 |
| 107 | 0.013 |
| 124 | 0.006 |
| 126 | 0.007 |

Test Example 2

Cell Proliferation Inhibition Assay

The following in vitro assay was used to evaluate the inhibiting effect of the compounds of present invention for the proliferation of triple-negative phenotypic breast cancer cell line MDA-MB-436.

Principle

This assay was used to study the effect of PARP-1 inhibitor alone for tumor suppression. Breast cancer susceptibility genes BRCA1 and BRCA2 play an important role in homologous recombination DNA repair. BRCA-deficient cells represent homologous recombination repair defect, if PARP-mediated DNA repair is inhibited at the same time, DNA damage in cells may be increased, resulting in chromatin abnormality or even cell death.

BRCA-deficient breast cancer cell line MDA-MB-436 was selected for the assay, PARP inhibitor was used alone to evaluate its damage effect on cells. The inhibition effect of the compound was expressed by IC$_{50}$.

Method

Breast cancer cell line MDA-MB-436 in good growth condition seeded in 96-well plates (5000 cells/well or 3000 cells/well, respectively), and cultured overnight in an incubator at 37° C., 5% CO$_2$ with saturated humidity. On the next day, samples with a series of concentration gradients were added and cultured for another six days. SRB method was used to detect the samples' inhibition on cell growth and calculate their growth inhibition rate. 4 Parameter Logistic Model in Xlfit software was used to calculate IC$_{50}$, and the results were shown in Table 2 below.

TABLE 2

| Compound No. | IC$_{50}$ (MDA-MB-436)/µM |
| --- | --- |
| AZD-2281 | 4.38 |
| 49 | 4.21 |
| 61 | 1.98 |
| 85 | 3.35 |
| 88 | 3.28 |
| 99 | 2.63 |
| 100 | 4.12 |

TABLE 2-continued

| Compound No. | IC$_{50}$ (MDA-MB-436)/μM |
|---|---|
| 107 | 3.17 |
| 124 | 3.70 |
| 130 | 3.85 |

Test Example 3

Solubility Test

To absorb the compound in the intestinal after oral administration, solid or suspension dosage forms must be disintegrated, dissolved and diffused onto the surfaces of intestinal epithelial cells before entering circulatory system. Compounds with high solubility could increase its concentration on the epithelial cell surface and facilitate intestinal to absorb more molecules in unit time and surface area. Insoluble compounds could lead to incomplete absorption, resulting in lower bioavailability when administered orally (see *Drug Metabolism and Disposition*, 1998, 26, 152-163; *Journal of Medicinal Chemistry*, 2001, 44, 1313-1333).

Principle

In this test, excess amount of test sample was added into pH=7.4 phosphate buffer. Ultrasonic was performed for 30 min until the drug no longer dissolved. The solution was continuously shaked for 24 hours at a constant temperature of 25° C. to achieve a thermodynamic equilibrium of compound, and then the solution was filtrated to get filtrate. Quantitative analysis of compound in filtrate using external standard method is performed according to "Appendix VD High Performance Liquid Chromatography, Part II of Pharmacopeia 2010," and the sample thermodynamic solubility in pH=7.4 phosphate buffered solution was determined.

Method

Solubility test of AZD-2281

Chromatographic Conditions

Agilent 1200 LC, Phenomen C18 column (4.6 mm*150 mm, 0.4 μm), mobile phase: methanol:water (60:40), flow rate: 1 mL/min, column temperature: 25° C., wave length: 230 nm, injection volume: 10 μL Preparation of Test Solution About 30 mg test compound was put in a 10 mL volumetric flask, about 8 mL pH=7.4 phosphate buffer was added and ultrasonic was performed for 30 min, and the solution was shaked for 24 hours in a shaker at a constant temperature of 25° C. The solution was settled for half an hour under 25° C., filtered with 0.45 nm hydrophilic filter. The filtrate was used as test sample.

Preparation of Standard Solution

Standard compound AZD-2281 was put in a volumetric flask and dissolved in the mobile phase. Standard stock solutions with different concentrations as shown in Table 3 were prepared. The solutions were injected to measure the peak area. The retention time of AZD-2281 was about 8.5 min. The peak area was regressed against concentration to get a regression equation y=29.66x+302.82 (r=0.9997), and the linear range is 52.45~83.92 g/mL (see FIG. 1).

TABLE 3

| Concentration (μg/mL) | 52.45 | 83.92 | 104.9 | 239.75 | 239.75 |
|---|---|---|---|---|---|
| Area | 1765.2 | 2821.4 | 3586.6 | 7261.7 | 14568 |

The test solution was injected for three times according to the above chromatographic conditions. The peak area was measured to calculate the corresponding concentration.

The procedures for testing the solubility of other compounds were similar with compound AZD-2281. The solubility results are shown in the following Table 4.

TABLE 4

| Example No. | Mobile Phase (methanol:water) | Retention Time (min) | Water Solubility (PH = 7.4)/g/mL |
|---|---|---|---|
| AZD-2281 | 60:40 | 8.5 | 531 |
| 55 | 60:40 | 7.6 | 602 |
| 79 | 65:35 | 8.4 | 650 |
| 100 | 55:45 | 8.3 | 660 |
| 124 | 55:35 | 8.5 | 1440 |
| 125 | 50:50 | 8.7 | 671 |
| 127 | 55:45 | 8.2 | 630 |

The preparation, activities and dissolution characteristics of the representative compounds of the present invention were explained in details in the preparation examples and test examples above. The compounds of the present invention can be synthesized by conventional methods. Compared with the similar compound AZD-2281, which represents the optimal activity, compounds of the present invention demonstrated higher activities and solubility.

What is claimed is:

1. The compound 4-(3-(4-(1-(dimethylamino)cyclopropanecarbonyl) piperazine-1-carbonyl)-4-fluorophenoxy)2H-phthalazin-1-one, pharmaceutically acceptable salt or stereoisomer thereof.

2. A pharmaceutical composition comprising an effective amount of the compound, pharmaceutically acceptable salt or stereoisomer thereof, of claim 1, and a pharmaceutically acceptable carrier.

* * * * *